(12) United States Patent
Hegyi et al.

(10) Patent No.: US 7,817,254 B2
(45) Date of Patent: Oct. 19, 2010

(54) OBTAINING INFORMATION FROM TIME VARIATION OF SENSING RESULTS

(75) Inventors: Alex Hegyi, Ann Arbor, MI (US);
Michael Bassler, Menlo Park, CA (US);
Peter Kiesel, Palo Alto, CA (US); Noble M. Johnson, Menlo Park, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 0 days.

(21) Appl. No.: 12/022,485

(22) Filed: Jan. 30, 2008

(65) Prior Publication Data

US 2009/0190121 A1    Jul. 30, 2009

(51) Int. Cl.
*G01P 3/36* (2006.01)
(52) U.S. Cl. .................. 356/28; 356/5.01; 356/5.15; 356/28.5
(58) Field of Classification Search .............. 356/28, 356/3.01–3.15, 4.01–4.1, 5.01–5.15, 6–22, 356/28.5
See application file for complete search history.

(56) References Cited

U.S. PATENT DOCUMENTS

| | | |
|---|---|---|
| 4,455,089 A | 6/1984 | Yeung et al. |
| 4,573,796 A | 3/1986 | Martin et al. |
| 5,151,585 A | 9/1992 | Siebert |
| 5,324,401 A | 6/1994 | Yeung et al. |
| 5,370,842 A | 12/1994 | Miyazaki et al. |
| 5,674,698 A | 10/1997 | Zarling et al. |
| 5,682,038 A | 10/1997 | Hoffman |
| 5,760,900 A | 6/1998 | Ito et al. |
| 5,793,485 A | 8/1998 | Gourley |
| 5,798,222 A | 8/1998 | Goix |

(Continued)

FOREIGN PATENT DOCUMENTS

WO     WO 95/20144 A1    7/1995

(Continued)

OTHER PUBLICATIONS

Bassler, ., Schmidt, O., Kiesel, P., Johnson, N.M., "Class Identification of Bio-Molecules Based on Multi-Color Native Fluorescence Spectroscopy", International Journal of High Speed Electronics and Systems (IJHSES), vol. 17, Issue 4, 2007, pp. 671-680.

(Continued)

*Primary Examiner*—Thomas H Tarcza
*Assistant Examiner*—Luke D Ratcliffe

(57) ABSTRACT

Sensing results from moving objects, e.g. from photosensing emanating light or from impedance-based sensing, can indicate sensed time-varying waveforms with information about objects. For example, a sensed time-varying waveform can be compared with another waveform, such as a reference waveform produced by objects of a certain type, to obtain comparison results indicating motion-independent information about the object; time-scaling can adjust for displacement rate such as speed. Also, a modulation periodicity value can be obtained from a sensed time-varying waveform and used in obtaining information about an object; for example, a periodic modulation frequency can be used with a given time's chirp frequency to obtain phase information about an object's position. Or, where periodic modulation frequency indicates displacement rate, time scaling during comparison can use a scaling factor based on the frequency. Objects can move fluidically as in flow cytometry or through scanning movement, as in document scanning.

38 Claims, 26 Drawing Sheets

U.S. PATENT DOCUMENTS

| | | | |
|---|---|---|---|
| 5,880,474 | A | 3/1999 | Norton et al. |
| 5,945,676 | A | 8/1999 | Khalil et al. |
| 5,982,478 | A * | 11/1999 | Ainsworth et al. ............ 356/28 |
| 6,558,945 | B1 | 5/2003 | Kao |
| 6,580,507 | B2 | 6/2003 | Fry et al. |
| 6,628,390 | B1 | 9/2003 | Johnson |
| 6,816,257 | B2 | 11/2004 | Goix |
| 6,839,140 | B1 | 1/2005 | O'Keefe et al. |
| 6,865,198 | B2 | 3/2005 | Taubman |
| 6,906,792 | B2 | 6/2005 | Ortyn et al. |
| 7,034,933 | B2 | 4/2006 | Walker et al. |
| 7,195,797 | B2 | 3/2007 | Mearini et al. |
| 7,248,361 | B2 | 7/2007 | Kiesel et al. |
| 7,252,360 | B2 | 8/2007 | Hersch et al. |
| 7,268,868 | B2 | 9/2007 | Kiesel et al. |
| 7,277,569 | B2 | 10/2007 | Bruce et al. |
| 7,291,824 | B2 | 11/2007 | Kiesel et al. |
| 7,305,112 | B2 | 12/2007 | Curry et al. |
| 7,315,667 | B2 | 1/2008 | Schmidt et al. |
| 7,358,476 | B2 | 4/2008 | Kiesel et al. |
| 7,433,552 | B2 | 10/2008 | Kiesel et al. |
| 7,440,101 | B2 | 10/2008 | Auer et al. |
| 7,471,399 | B2 | 12/2008 | Kiesel et al. |
| 7,479,625 | B2 | 1/2009 | Kiesel et al. |
| 7,502,123 | B2 | 3/2009 | Schmidt et al. |
| 7,522,786 | B2 | 4/2009 | Kiesel et al. |
| 7,545,513 | B2 | 6/2009 | Kiesel et al. |
| 7,547,904 | B2 | 6/2009 | Schmidt et al. |
| 7,554,673 | B2 | 6/2009 | Kiesel et al. |
| 7,701,580 | B2 | 4/2010 | Bassler et al. |
| 2003/0020915 | A1 | 1/2003 | Schueller et al. |
| 2003/0235924 | A1 | 12/2003 | Adams et al. |
| 2004/0038386 | A1 | 2/2004 | Zesch et al. |
| 2004/0067167 | A1 | 4/2004 | Zhang et al. |
| 2004/0223135 | A1 * | 11/2004 | Ortyn et al. .................. 356/28 |
| 2005/0128479 | A1 | 6/2005 | Gilbert et al. |
| 2005/0162648 | A1 | 7/2005 | Auer et al. |
| 2005/0213082 | A1 * | 9/2005 | DiBernardo et al. ... 356/139.03 |
| 2006/0203224 | A1 * | 9/2006 | Sebastian et al. ........... 356/4.09 |
| 2006/0268260 | A1 | 11/2006 | Liu et al. |
| 2006/0274313 | A1 | 12/2006 | Gilbert et al. |
| 2007/0070347 | A1 | 3/2007 | Scherer et al. |
| 2007/0076210 | A1 | 4/2007 | Kiesel et al. |
| 2007/0145249 | A1 | 6/2007 | Kiesel et al. |
| 2007/0146704 | A1 | 6/2007 | Schmidt et al. |
| 2007/0147189 | A1 | 6/2007 | Schmidt et al. |
| 2007/0147728 | A1 | 6/2007 | Schmidt et al. |
| 2007/0172969 | A1 | 7/2007 | Wong et al. |
| 2008/0013092 | A1 | 1/2008 | Maltezos et al. |
| 2008/0013877 | A1 | 1/2008 | Schmidt et al. |
| 2008/0181827 | A1 | 7/2008 | Bassler et al. |
| 2008/0183418 | A1 | 7/2008 | Bassler et al. |
| 2008/0186488 | A1 | 8/2008 | Kiesel et al. |
| 2008/0186492 | A1 | 8/2008 | Kiesel et al. |
| 2008/0186500 | A1 | 8/2008 | Schmidt et al. |
| 2008/0186504 | A1 | 8/2008 | Kiesel et al. |
| 2008/0197272 | A1 | 8/2008 | Kiesel et al. |
| 2008/0299327 | A1 | 12/2008 | Salleo et al. |
| 2009/0194705 | A1 | 8/2009 | Kiesel et al. |
| 2009/0195773 | A1 | 8/2009 | Bassler et al. |
| 2009/0195852 | A1 | 8/2009 | Bassler et al. |
| 2009/0220189 | A1 | 9/2009 | Kiesel et al. |

FOREIGN PATENT DOCUMENTS

| | | |
|---|---|---|
| WO | WO 99/54730 | 4/1999 |
| WO | WO 99/54730 A1 | 10/1999 |
| WO | WO 00/62050 A1 | 10/2000 |
| WO | WO 02/25269 A2 | 3/2002 |

OTHER PUBLICATIONS

Cheung, K., Gawad, S., and Renaud, P., "Impedance Spectroscopy Flow Cytometry: On-Chip Label-Free Cell Differentiation", Cytometry Part A, vol. 65A, 2005, pp. 124-132.

"Flow Cytometry", printed from www.wellscenter.iupui.edu/MMIA on Jan. 29, 2008, 4 pages.

Seamer, L.C., Kuckuck, F., and Sklar, L.A., "Sheath Fluid Control to Permit Stable Flow in Rapid Mix Flow Cytometry", Cytometry, vol. 35, 1999, pp. 75-79.

Bhatta, H., Goldys, E.M., and Learmonth, R., "Rapid Identification of Microorganisms by Intrinsic Fluorescence", Proc. of SPIE, vol. 5699, 2005, pp. 9-18.

Singh, K., Liu, C., Capjack, C., Rozmus, W., and Backhouse, C.J., "Analysis of cellular structure by light scattering measurements in a new cytometer design based on a liquid-core waveguide", IEE Proc.-Nanobiotechnol., vol. 151, No. 1, Feb. 2004, pp. 10-16.

Liang, X.J., Liu, A.Q., Zhang, X.M., Yap, P.H., Ayi, T.C., and Yoon, H.S., "Refractive Index Measurement of Single Living Cell Using a Biophotonic Chip for Cancer Diagnosis Applications", 9th International Conference on Miniaturized Systems for Chemistry and Life Sciences, Oct. 9-13, 2005, pp. 464-466.

Adams, M.L., Enzelberger, M., Quake, S., and Scherer, A., "Microfluidic Integration on detector arrays for absorption and fluorescence micro-spectrometers", Sensors and Actuators, 2003, pp. 25-31.

Office communication in U.S. Appl. No. 12/023,436, mailed Dec. 23, 2008, 15 pages.

Office communication in U.S. Appl. No. 12/024,490, mailed Dec. 24, 2008, 12 pages.

Bracewell, R. N., The Fourier Transform and its Applications, Second Edition, McGraw-Hill, 1978, Table of Contents and pp. 24-50, 98-126, and 177-188.

Shapiro, H. M., Practical Flow Cytometry, Fourth Edition, Wiley-Liss, 2003, Table of Contents and pp. 49-59, 124-183, 191-197, 345, and 364-366.

Hoffman, R. A., "Flow Cytometry: Instrumentation, Applications, Future Trends and Limitations", Springer Series on Fluorescence, vol. 6, 2008, pp. 307-342.

Office communication in U.S. Appl. No. 11/315,386, mailed Sep. 26, 2008, 37 pages, published in PAIR.

Amendment with Information Disclosure in U.S. Appl. No. 11/315,386, submitted Dec. 23, 2008, 27 pages, published in PAIR.

Notice of Allowance and Fee(s) Due in U.S. Appl. No. 11/315,386, mailed Mar. 20, 2009, 8 pages, published in PAIR.

Office communication in U.S. Appl. No. 11/702,470, mailed Apr. 25, 2008, 22 pages, published in PAIR.

Amendment in U.S. Appl. No. 11/702,470, submitted Jul. 25, 2008, 21 pages, published in PAIR.

Office communication in U.S. Appl. No. 11/702,470, mailed Oct. 31, 2008, 22 pages, published in PAIR.

Amendment in U.S. Appl. No. 11/702,470, submitted Jan. 30, 2009, 22 pages, published in PAIR.

Notice of Allowance and Fee(s) Due in U.S. Appl. No. 11/702,470, mailed Apr. 24, 2009, 15 pages, published in PAIR.

Amendment in U.S. Appl. No. 12/024,490, submitted Mar. 24, 2009, 32 pages.

Amendment in U.S. Appl. No. 12/023,436, submitted Mar. 23, 2009, 22 pages.

Office communication in U.S. Appl. No. 12/024,490, mailed Nov. 2, 2009, 14 pages, published in PAIR.

Office communication in U.S. Appl. No. 11/698,409, mailed Nov. 17, 2009, 18 pages, published in PAIR.

Office communication in U.S. Appl. No. 12/025,394, mailed Jan. 22, 2010, 7 pages, published in PAIR.

Office communication in U.S. Appl. No. 12/023,436, mailed Feb. 5, 2010, 16 pages, published in PAIR.

Amendment in U.S. Appl. No. 12/023,436, submitted Mar. 23, 2010, 24 pages, published in PAIR.

Office communication in U.S. Appl. No. 12/023,436, mailed Apr. 16, 2010, 8 pages, published in PAIR.

Amendment in U.S. Appl. No. 12/025,394, submitted Apr. 22, 2010, 17 pages, published in PAIR.

Amendment in U.S. Appl. No. 11/698,409, submitted May 17, 2010, 16 pages, published in PAIR.

Office communication in U.S. Appl. No. 12/023,436, mailed Jun. 12, 2009, 20 pages, published in PAIR.

Amendment in U.S. Appl. No. 12/023,436, submitted Sep. 3, 2009, 29 pages, published in PAIR.

Office communication in U.S. Appl. No. 12/024,490, mailed Jul. 22, 2009, 16 pages, published in PAIR.

Amendment After Final Rejection in U.S. Appl. No. 12/024,490, submitted Sep. 22, 2009, 28 pages, published in PAIR.

Office communication in U.S. Appl. No. 11/702,328, mailed May 27, 2009, 28 pages, published in PAIR.

Amendment in U.S. Appl. No. 11/702,328, submitted Aug. 14, 2009, 33 pages, published in PAIR.

Office communication in U.S. Appl. No. 11/702,328, mailed Sep. 11, 2009, 4 pages, published in PAIR.

Response to Interview Summary n U.S. Appl. No. 11/702,328, submitted Sep. 18, 2009, 6 pages, published in PAIR.

Office communication in U.S. Appl. No. 11/702,328, mailed Oct. 5, 2009, 23 pages, published in PAIR.

Amendment After Final Rejection in U.S. Appl. No. 11/702,328, submitted Nov. 12, 2009, 22 pages, published in PAIR.

Office communication in U.S. Appl. No. 11/702,328, mailed Dec. 2, 2009, 3 pages, published in PAIR.

Amendment with Request for Continued Examination in U.S. Appl. No. 11/702,328, submitted Dec. 29, 2009, 24 pages, published in PAIR.

Notice of Allowance and Fee(s) Due in U.S. Appl. No. 12/024,490, mailed Nov. 2, 2009, 14 pages, published in PAIR.

Office communication in U.S. Appl. No. 11/698,409, mailed Jun. 11, 2010, 21 pages, published in PAIR.

* cited by examiner

FIG. 9
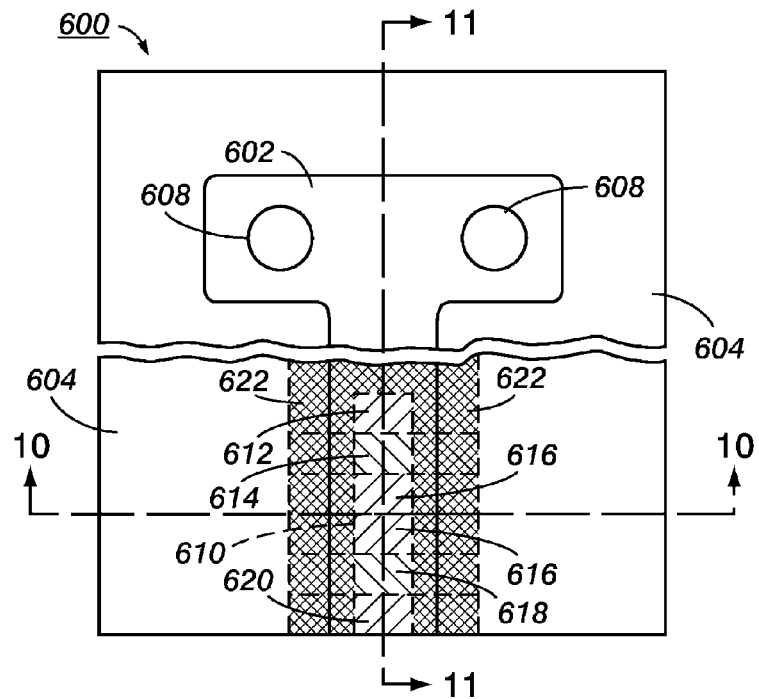
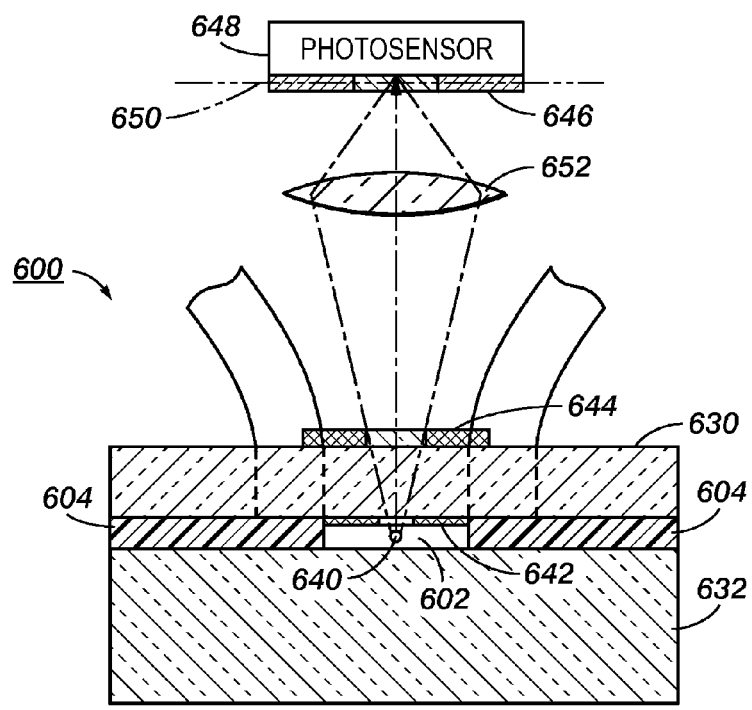
FIG. 10

FIG. 13
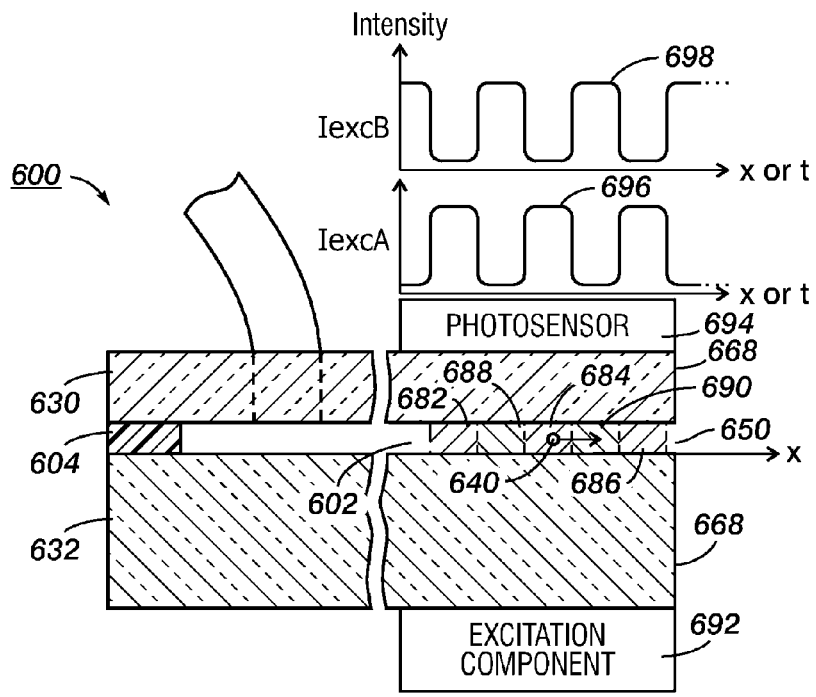
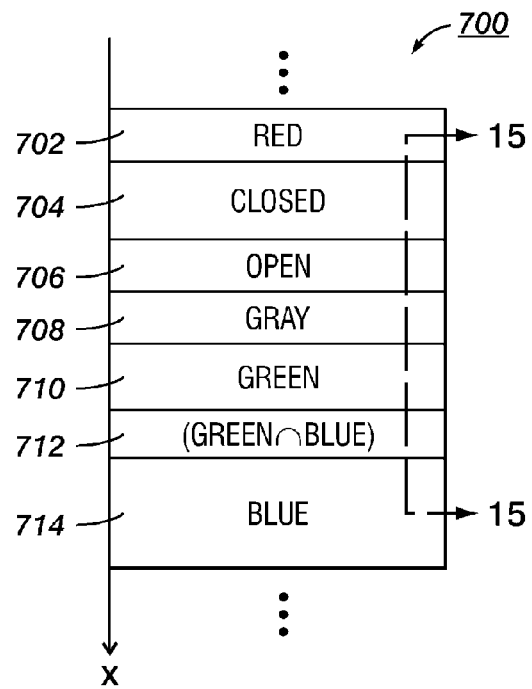
FIG. 14

OBTAINING INFORMATION FROM TIME VARIATION OF SENSING RESULTS

The following applications, each of which is hereby incorporated by reference in its entirety, might be regarded as related to this application: "Sensing Photon Energies Emanating from Channels or Moving Objects", U.S. patent application Ser. No. 11/315,386, now published as U.S. Patent Publication No. 2007/0146704; "Sensing Photon Energies of Optical Signals", U.S. patent application Ser. No. 11/315,926, now published as U.S. Patent Publication No. 2007/0147189; "Sensing Photons from Objects in Channels", U.S. patent application Ser. No. 11/315,992, now published as U.S. Patent Publication No. 2007/0145249; "Obtaining Analyte Information", U.S. patent application Ser. No. 11/316,303, now published as U.S. Patent Publication No. 2007/0148760; "Providing Light to Channels or Portions", U.S. patent application Ser. No. 11/316,660, now published as U.S. Patent Publication No. 2007/0147728; "Method and System for Evaluation of Signals Received from Spatially Modulated Excitation and Emission to Accurately Determine Particle Positions and Distances", U.S. patent application Ser. No. 11/698,338; "Method and System Implementing Spatially Modulated Excitation or Emission for Particle Characterization with Enhanced Sensitivity", U.S. patent application Ser. No. 11/698,409; "Obtaining Information From Optical Cavity Output Light", U.S. patent application Ser. No. 11/702,249; "Photosensing Optical Cavity Output Light", U.S. patent application Ser. No. 11/702,250; "Distinguishing Objects", U.S. patent application Ser. No. 11/702,328; "Encoding Optical Cavity Output Light", U.S. patent application Ser. No. 11/702,363; "Moving Analytes and Photosensors", U.S. patent application Ser. No. 11/702,470; "Surface Energy Control Methods for Color Filter Printing", U.S. patent application Ser. No. 11/755,717; "Producing Sandwich Waveguides", U.S. patent application Ser. No. 11/777,661; and "Producing Fluidic Waveguides", U.S. patent application Ser. No. 11/777,712.

BACKGROUND OF THE INVENTION

The present invention relates generally to techniques involving sensing to obtain information about objects. More specifically, techniques can obtain sensing results with time variation that includes information about objects.

Various techniques have been proposed for obtaining information about objects. For example, U.S. Patent Application Publication No. 2007/0145249 describes a fluidic structure with a channel along which is a series of sensing components to obtain information about objects traveling within the channel, such as droplets or other objects carried by fluid. A sensing component includes a set of cells that photosense a range of photon energies that emanate from objects. A processor can receive information about objects from the sensing components and use it to obtain spectral information. Similar techniques are described, for example, in U.S. Patent Application Publication Nos. 2007/016704, 2007/0147189, and 2007/0147728.

It would be advantageous to have improved techniques for obtaining information about objects, including improved techniques for obtaining information from sensing results.

SUMMARY OF THE INVENTION

The invention provides various exemplary embodiments, including methods and apparatus. In general, the embodiments involve using sensing results that indicate time-varying waveforms to obtain information about objects.

These and other features and advantages of exemplary embodiments of the invention are described below with reference to the accompanying drawings.

BRIEF DESCRIPTION OF THE DRAWINGS

FIG. 9 is a top view of an article that can include a filter arrangement and that can be included in an encoding component as in FIG. 2.

FIG. 10 is a cross-sectional view of an implementation of an article similar to that in FIG. 9, taken along the line 10-10.

FIG. 13 is a cross-sectional view of an implementation of an article similar to that in FIG. 12, taken along the line 13-13, together with graphs of sensed intensities.

FIG. 14 is a schematic top view of another filter arrangement that can be included in an encoding component as in FIG. 2.

DETAILED DESCRIPTION

Figure 1:
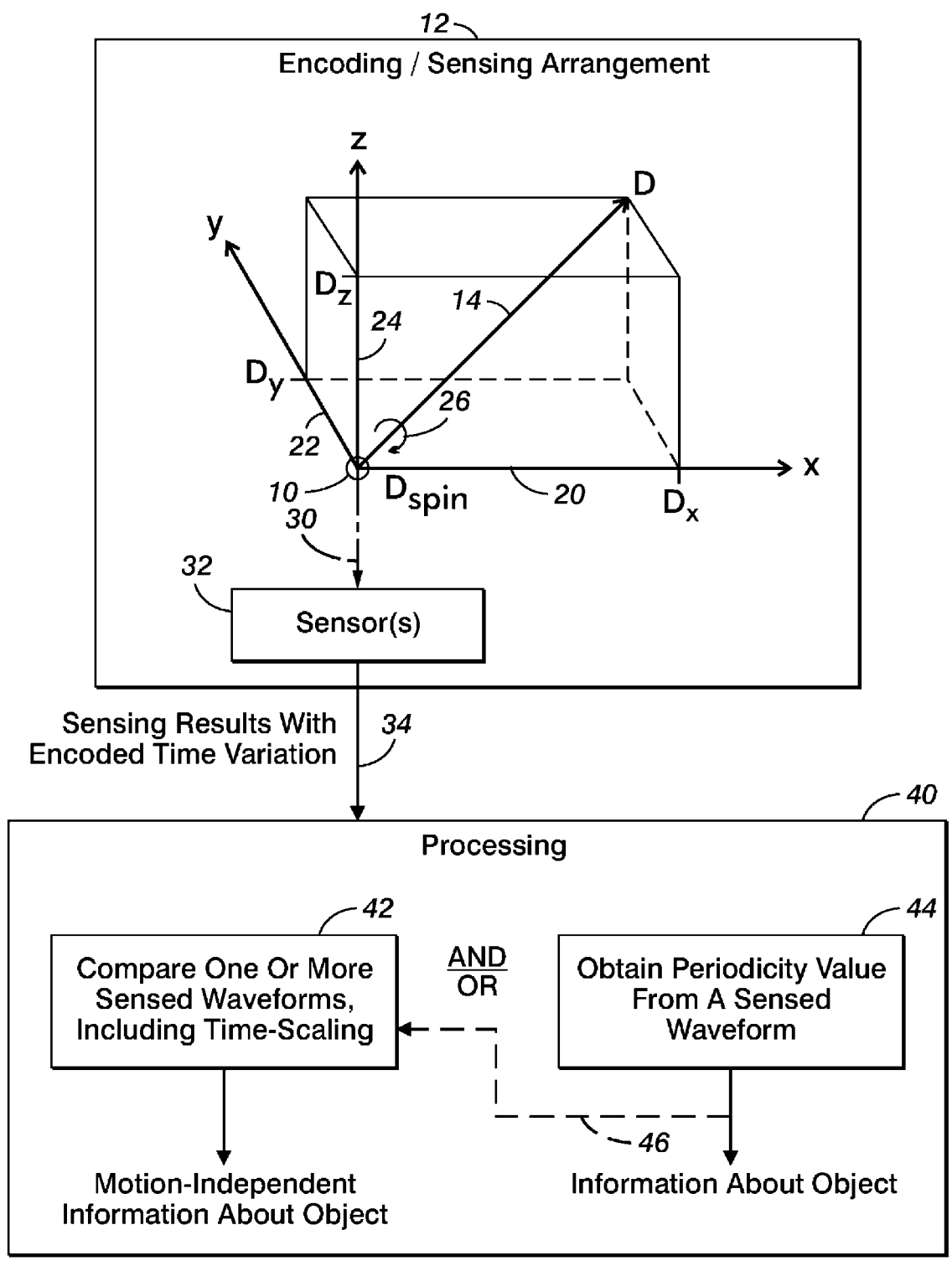
FIG. 1 is a schematic diagram showing features of techniques that use sensing results to obtain information about an object.

In the following detailed description, numeric values and ranges are provided for various aspects of the implementations described. These values and ranges are to be treated as examples only, and are not intended to limit the scope of the claims. In addition, a number of materials are identified as suitable for various facets of the implementations. These materials are to be treated as exemplary, and are not intended to limit the scope of the claims.

"Light" refers herein to electromagnetic radiation of any wavelength or frequency; unless otherwise indicated, a specific value for light wavelength or frequency is that of light propagating through vacuum. Light that can include information is sometimes referred to herein as an "optical signal".

The term "sensing" is used herein in the most generic sense of obtaining information from a physical stimulus; sensing therefore includes actions such as detecting, measuring, and so forth. A "sensor" is a device that performs sensing. Data or other signals that indicate or include results of sensing are sometimes referred to herein as "sensing results".

"Photosensing" is sensing of light. A "photosensor" is accordingly an electronic device that performs photosensing. More specifically, if optical signals include information, a photosensor that receives the optical signals may be able to sense the information and provide sensing results that indicate or include the information. A surface at which photosensing occurs is referred to herein as a "photosensitive surface".

Another type of sensing relevant to some exemplary implementations described below is "impedance-based sensing", meaning sensing that obtains information from variation in resistance (or inversely, conductivity), capacitance, inductance, or another form of electrical impedance that varies in response to a physical stimulus.

The various exemplary implementations described below address problems that arise in using sensing results to obtain information about an object such as a biological cell, a molecule, or a submolecular complex. Many sensing techniques provide sensing results with information about objects, but available techniques for extracting information have limitations.

One type of limitation results from motion of an object relative to sensors or other components. Such motion can interfere with information extraction, and, in particular, can prevent effective comparison between time-varying wave forms. For example, a correlation operation on two signals, one sensed and one expected or desired (sometimes referred to as a "template"), can improve signal to noise (S/N) ratio, but a correlation operation on time-varying signals is highly sensitive to differences in time domain scales of signals being compared—if the time scales are sufficiently different, correlation results may not indicate a correlation or anti-correlation that actually exists. This is problematic for moving objects, because, as explained in greater detail below, an object's motion can modify time scale of sensing results.

Another limitation relates to computational difficulties that arise in obtaining an object's position, in some contexts referred to herein as "phase information". Some precise techniques for obtaining position are computationally intensive, making it difficult to implement them for real-time information extraction.

In addressing such problems, some exemplary implementations described below, in comparing sensed time-varying waveforms, perform time scaling on at least one of the waveforms being compared. Other exemplary implementations obtain a periodicity value from periodic modulation of sensed time-varying waveforms and use it to obtain information about an object. In some exemplary implementations, the periodicity value is a scaling value that is used to perform time scaling on a waveform being compared.

The term "photon" refers herein to a quantum of light, and the term "photon energy" refers herein to the energy of a photon. Light can be described as having a "photon energy distribution" or, more commonly, a "spectrum", meaning the combination of photon energies that are included in the light; highly monochromatic light, for example, has a photon energy distribution or spectrum with one peak energy value.

Light can also be described as provided by a "light source," which, unless otherwise specified, refers herein to any device, component, or structure that can provide light of the type described; examples of light sources relevant to the below-described implementations include various kinds of pulsed and unpulsed lasers and laser structures, laser diodes (LDs), light emitting diodes (LEDs), superluminescent LEDs (SLEDs), resonant cavity LEDs, sources of broadband light that is spectrally filtered such as with a monochromator, and so forth.

To "propagate" light through a region or structure is to transmit or otherwise cause the light to propagate through the region or structure. The light may be referred to as "propagated light" or "propagating light".

Propagating light can often be usefully characterized by direction and speed of propagation, with direction typically illustrated by one or more rays and with speed typically being described relative to the constant c, also referred to as the speed of light in vacuum. Where the speed of light in a medium M is a constant $c_M$ less than c, then M has an index of refraction $n_M = c/c_M$.

Where light changes direction in a way that can be illustrated or approximated as a vertex between an incoming ray and an outgoing ray that are both on one side of a surface, the change may be referred to as a "reflection"; similarly, to "reflect" light is to cause the light to change its direction of propagation approximately at such a surface, referred to herein as a "reflection surface". Similarly, where light changes direction in a way that can be illustrated or approximated as a vertex between an incoming ray and an outgoing ray that are on opposite sides of a surface between two media with different indices of refraction, the change may be referred to as a "refraction"; similarly, to "refract" light is to cause the light to change its direction of propagation approximately at such a surface, referred to herein as a "refraction surface". In many practical applications, both reflection and refraction occur at a surface, which may be referred to herein as a "partially reflecting surface".

Where light propagates at less than c, it may be useful to obtain an "optical distance" of propagation; for any segment of length d in which speed of propagation is constant $\epsilon^*C$, where $\epsilon = 1/n_{EFF} \leq 1$ and $n_{EFF}$ is an effective index of refraction for the segment, optical distance $D(\epsilon) = d/\epsilon$. An optical distance may be referred to herein as an "optical thickness", such as where light is propagating through a thickness of material.

A "range of photon energies" or an "energy range" is a range of energy values that photons can have. An energy range can be described, for example, as a range of wavelengths or a range of frequencies or, in appropriate cases, by the range's central wavelength or frequency and possibly also the range's width.

A "subrange" of a range of photon energies is a part of the range, and can be similarly described. In general, the upper and lower boundaries and widths of ranges and subranges are approximate. To provide output photons or to photosense quantity of photons "throughout", "within", or "in" a range or subrange means to provide photons or to obtain information about quantity of photons that are predominantly within the range or subrange. In typical cases, between 60-90% of the provided photons or sensed quantity of photons have energies within the range or subrange, but the percentage could be lower or higher. In some applications, 90% or even 95% or more of the provided photons or sensed quantity of photons have energies within the range or subrange.

The term "electrical signal" is used herein to encompass any signal that transfers information from one position or region to another in an electrical, electronic, electromagnetic, or magnetic form. Similarly to thermal signals, electrical signals may be conducted from one position or region to another by electrical or magnetic conductors, but the broad scope of electrical signals also includes light and other electromagnetic forms of signals and other signals transferred through non-conductive regions due to electrical, electronic, electromagnetic, or magnetic effects. In general, the broad category of electrical signals includes both "analog" and "digital" signals: An "analog" electrical signal includes information in the form of a continuously variable physical quantity, such as voltage; a "digital" electrical signal, in contrast, includes information in the form of discrete values of a physical characteristic, which could also be, for example, voltage.

Unless the context indicates otherwise, the terms "circuitry" and "circuit" are used herein to refer to structures in which one or more electronic components have sufficient electrical connections to operate together or in a related manner. In some instances, an item of circuitry can include more than one circuit. An item of circuitry that includes a "processor" may sometimes be analyzed into "hardware" and "software" components; in this context, "software" refers to stored or transmitted data that controls operation of the processor or that is accessed by the processor while operating, and "hardware" refers to components that store, transmit, and operate on the data. The distinction between "software" and "hardware" is not always clear-cut, however, because some components share characteristics of both; also, a given software component can often be replaced by an equivalent hardware component without significantly changing operation of circuitry, and a given hardware component can similarly be replaced by equivalent processor operations controlled by software.

Circuitry can be described based on its operation or other characteristics. For example, circuitry that performs control operations is sometimes referred to herein as "control circuitry" and circuitry that performs processing operations is sometimes referred to herein as "processing circuitry".

In general, sensors, processors, and other such items may be included in a system in which they are operated automatically or partially automatically. As used herein, the term "system" refers to a combination of two or more parts or components that can perform an operation together. A system may be characterized by its operation; for example, an "object distinguishing system" is a system that operates somehow to distinguish objects.

Within a system, device, or other article, components and parts may be referred to in a similar manner. One component of an object distinguishing system, for example, can be described as an "encoding/sensing component", in some cases referred to as an "encoding/sensing arrangement", in either case meaning that the component or arrangement operates to encode and sense information, providing sensing results that indicate the encoded information; various other components are described below. In addition, a component or part may be identified by characteristics other than its operation.

In FIG. 1, object 10 is a moving object traveling along a respective path, illustratively within encoding/sensing arrangement 12. Object 10 could, for example, be one of a series of objects traveling through a fluidic channel or one of an array of objects traveling in a scanning movement. The term "path" is used herein in the general sense of a series of positions and/or configurations that a moving and/or varying object can have during its motion and/or variation. For generality, a part of a path is sometimes referred to herein as a "segment", which could encompass any continuous series of one or more positions and/or configurations within a path.

Arrow 14, labeled "D", represents displacement of object 10 during one increment of time. Displacement D can be analyzed into several component displacements, with examples shown in FIG. 1 including x-direction component 20, labeled "$D_x$"; y-direction component 22, labeled "$D_y$"; z-direction component 24, labeled "$D_z$"; and spin component 26, labeled "$D_{spin}$". In general, however, an object's displacement can be analyzed into any suitable combination of components, and the combination in FIG. 1 is merely exemplary. In general, values of displacement D or of any of a set of components into which it is analyzed are referred to herein collectively as "displacement values". A "displacement rate" can then be understood as a rate of any combination of one or more such displacement values per unit of time; in particular, the general term "speed" includes any displacement rate obtained in units of distance per unit time, such as μm/sec.

As object 10 travels, it interacts, as represented by arrow 30, with one or more sensors 32. For example, light could emanate from it, such as by emission, reflection or other scattering, and/or transmission, and sensors 32 could include one or more photosensors that sense the emanating light. In addition or alternatively, an electrical or magnetic interaction could occur with sensors 32, which could include electrodes, coils, or other components that can perform resistive, capacitive, inductive, or other impedance-based sensing of electrical or magnetic characteristics of object 10 as it travels relative to arrangement 12. The term "interact" is used herein in the broad sense that includes any type of interaction as a result of which sensors 32 can provide sensing results that include information about object 10; this would include, for example, interactions in which object 10 emanates light or otherwise provides or affects signals that are sensed by sensors 32 and also interactions in which presence and/or motion of object 10 near sensors 32 affects sensing results without any measurable signal being transferred to sensors 32, such as through resistive, capacitive, inductive, or other impedance-based sensing.

As a result of displacement of object 10 relative to arrangement 12, sensing results, represented by arrow 34, include encoded time variation. In the case of emanating light, time variations in light intensity within an application's range of photon energies could include information, and the information could therefore be encoded in time-varying signals from photosensors that indicate intensity variation over time. For other types of sensing, information could be included in time variations that similarly occur, for example, in a resistance, capacitance, inductance, or other impedance value within a circuit that includes one or more sensors, and the information could therefore be encoded in time-varying signals from the sensors that indicate intensity variation over time.

More specifically, information about object 10 can be encoded in time variation, such as by operations of encoding/sensing arrangement 12. In general, part of the encoded information corresponds only with values of displacement D or its components, and is therefore referred to herein as "motion-dependent information". Another part, however, can be encoded independently of displacement values, and is therefore referred to herein as "motion-independent information"; in other words, motion-independent information does not indicate displacement values or rates of displacement during encoding, but indicates position, spectrum, mass, or another characteristic of object 10. In the case of photosensing results, such characteristics of an object could include, for example, its emission spectrum, scattering spectrum, and/or transmission/absorption spectrum, all of which are referred to collectively herein as its "emanation spectra". Various other characteristics of an object might be sensed in other ways, such as through impedance-based sensing; possibly including, for example, volume, density, cross-section or other shape, chemical composition, net charge, charge polarity, magnetic axis orientation, magnetic permeability or other property, and so forth.

In general, an application that employs encoding/sensing arrangement 12 will include constraints on sensing results. For example, photosensors must sense emanating light within an application's range of photon energies; in other words techniques as in FIG. 1 can be successfully used in a given application, e.g. flow cytometry, bio-chip readout, any suitable kind of analyte detection, or scanning of documents or other arrays of objects, provided photosensors are used that can sense energies within an application's range, even though emanating light might also include photon energies that are outside the application's range and that might not interact with other components in the same way as light in the application's range. Similarly, sensors that provide sensing results based on variations in impedance or other effects must sense within relevant constraints of a given application, but need not be able to sense outside those constraints.

The term "object" is used herein in the general sense of any distinguishable thing about which information can be obtained by a sensor and included in its sensing results. In some implementations, sensors can obtain information about objects by receiving signals from them; for example, signals in the form of light can emanate from an object, whether through emission (e.g. radiation, fluorescence, incandescence, chemoluminescence, bioluminescence, other forms of luminescence, etc.), scattering (e.g. reflection, deflection, diffraction, refraction, etc.), or transmission, and can be sensed by a photosensor. The light "emanates from" or is simply "from" the object, and may be referred to herein as "emanating light". An object from which light is emanating may be referred to herein as a "light-emanating object". In other implementations, sensors can obtain information about objects in other ways, some of which are mentioned herein.

Examples of objects that could occur in implementations as described below include droplets, small volumes of fluid, single molecules, agglomerated molecules, molecule clusters, cells, viruses, bacteria, lengthy polymers such as DNA or protein chains, submolecular complexes such as tags on DNA or protein chains, microparticles, nanoparticles, beads or other small particles that can bind and carry specific chemicals or other analytes, emulsions, any such type of object in an array such as an array of sample wells, and a distinguishable region of a surface such as a small area of a sheet of paper or other image-bearing medium; a distinguishable region, could, for example, be a colored spot. A droplet or small volume of fluid may, for example, include atoms, molecules, or other particles that emit light spontaneously or in response to excitation; a particle could be a "fluorescent component" of a droplet, fluorescing in response to excitation. Or a droplet may include particles that absorb light incident on the droplet, so that the droplet does not reflect or otherwise scatter the absorbed light; in this case, a particle could be an "absorbent component" of a droplet. Or a droplet may include particles that scatter light incident on the droplet in a way that depends on photon energy, so that the droplet scatters the incident light correspondingly; in this case, a particle could be a "scattering component" of a droplet. An analyte (i.e. a chemical species being investigated) in a droplet or other object can act as a fluorescent, absorbent, or scattering component. Analyte that is otherwise homogeneously distributed, for example, can be localized by binding to carrier beads, resulting in a moving object that emanates light or provides other signals in a way that depends on the analyte.

With respect to a light-emanating object, the expressions "characteristic of an object" and "emanating light including information" have related meanings: The term "characteristic" refers to a trait, quality, or property of an object that can be measured and that persists with a given value or within a given range or other subset of possible values while light that "includes information about the characteristic" is emanating from the object. In appropriate implementations, characteristics of an object could include mass, volume, density, cross-section or other shape, chemical composition, position, speed, acceleration, direction of movement, spin axis, directional or angular velocity or momentum, net charge, charge polarity, absorption spectrum, emission spectrum, scattering spectrum, and so forth. Therefore, emanating light "includes" information about a characteristic of an object if information included in the emanating light indicates a value, range, or other measure of the characteristic. Similar terminology can apply in implementations in which sensors obtain information in ways other than by sensing emanating light; for example, information about speed, polarizability, and so forth could be included in impedance-based sensing results.

Emanating light or other types of signals can "include information" in many ways, some of which are described below in relation to specific implementations. Various criteria could be used to determine whether emanating light or another type of signal includes specified information, and such criteria can be referred to as "encoding criteria". Some encoding criteria, for example, involve comparison of magnitude of a signal with noise magnitude, e.g. signal-to-noise (S/N) ratios, because S/N ratio can affect whether specified information can be recovered from sensing results obtained by photosensing emanating light. Other types of encoding criteria could be used as appropriate. Where emanating light or another type of signal satisfies an appropriate encoding criterion for specified information, the light or signal may be said to "encode" the information.

Similarly, sensing results, whether from photosensing emanating light, from impedance-based sensing, or from another type of sensing, can "include information" in many ways, and similar encoding criteria could be applied as with signals. Where sensing results indicate one or more time-varying waveforms, the sensing results can be referred to as having "encoded time variation".

The term "waveform" is used herein in the general sense of any set of values that varies over one or more dimensions, whether continuous or discrete, whether analog or digital, and whether measured or obtained in any other way; a "time-varying waveform" is a waveform that varies over a time dimension. Some of the time-varying waveforms described below in relation to exemplary implementations include intensity values, but the expression "time-varying waveforms" also encompasses other values that vary over time, including purely numerical values with no specified units or other physical significance. A "sensed time-varying waveform" is a time-varying waveform that is indicated by sensing results obtained over time. For example, if a photosensor provides sensed quantities that indicate intensity of received light, its sensing results could indicate a time-varying waveform indicating intensity sensed over time.

In a system in which sensing results can include information about characteristics of objects, an object "travels" or is caused "to travel" if the object has a succession of positions over time with respect to one or more parts or components of the system or one or more patterns or other features of the system's environment such that information about the object's traveling, e.g. about speed or other rate of displacement, can be included in the emanating light or other signals. An object that travels is sometimes also referred to herein as "moving" or as having "motion" or "movement", but an object's traveling may result from any appropriate motion of the object and/or motion of parts or components of the system or patterns or other features of its environment. In other words, motion of an object includes any relative movement between the object and parts or components of a system or patterns or features of the system's environment, such as an encoding and/or sensing component of the system or a pattern of excitation or of filtering or another environmental pattern or feature.

A moving object's path is treated herein as providing a directional orientation as follows: A direction parallel or approximately parallel to the path is sometimes referred to as a "longitudinal" or "lengthwise" direction, while a direction perpendicular or approximately perpendicular to the path is sometimes referred to as a "radial", "lateral", or "transverse" direction. The lengthwise direction in which the object is moving is sometimes referred to as "forward" or "downstream", while the opposite direction is sometimes referred to as "backward" or "upstream". A radial direction away from the path is "out" or "outward", while a radial direction toward the path is "in" or "inward". Light propagating toward the path may be referred to as "incoming" or "incident", while light propagating away from the path may be referred to as "outgoing". A component or arrangement of components is "along" the path if it is disposed near the path and has some extent in a longitudinal direction. A component or arrangement of components is "around" the path if, in a plane transverse to the path, it intersects multiple radial directions, at least two of which are separated by approximately 180 degrees of arc. A direction that similarly goes around the path is sometimes referred to herein as a "rotation" direction. In general, it should be understood that the above directional orientation is arbitrary and only for ease of description, and that a moving object's path may have any appropriate orientation.

Sensing results or signals that include information about an object's traveling are sometimes referred to herein as "motion-affected", as including "motion-dependent information", or as having "motion-dependent encoding". If the motion-dependent information depends on a moving object's speed, it may be referred to more specifically as "speed-dependent information". For example, an object could travel by being conveyed in fluid, such as liquid, gas, or aerosol, through a region of a sensing component; in such a case the object may be referred to as being "carried" by fluid; sensing results or signals could include speed-dependent information indicating the object's speed as it is carried through the region by fluid. In another example, an object contained in or otherwise supported by a support structure could travel due to relative scanning movement between the support structure and an encoding and/or sensing component such as an array, and sensing results or signals could include speed-dependent information indicating speed of the object relative to the encoding and/or sensing component.

Encoding/sensing arrangement 12 can be implemented in any appropriate way, and some exemplary implementations are described below. In general, its sensing results initially take the form of analog or digital electrical signals, depending on the structure and circuitry included in encoding/sensing arrangement 12, but could be converted to other forms, such as optical or other electromagnetic signals, such as for subsequent storage, transmission, and processing.

Processing in box 40 uses sensing results from encoding/sensing arrangement 12 to obtain information about object 10. As shown within box 40, the processing could include either or both of two more specific operations, illustrated respectively in boxes 42 and 44. Processing in box 40 could be performed after any appropriate transmission, storage, conversion, or other operations on the sensing results, provided the operations preserve encoded information from arrangement 12. In particular, processing in box 40 requires sufficient sensing results to indicate one or more sensed time-varying waveforms.

The operation represented in box 42 uses sensing results from encoding/sensing arrangement 12 to perform waveform comparison. More particularly, the comparing operation in box 42 is performed on a set of time-varying waveforms to obtain comparison results. The set of waveforms that are compared in box 42 includes at least one sensed time-varying waveform indicated by the sensing results from encoding/sensing arrangement 12; for example, it could compare two or more sensed time-varying waveforms with each other or it could compare a sensed time-varying waveform with a reference time-varying waveform or another waveform that has been previously obtained and stored or that is obtained from some other source. As used herein, a "reference waveform" is a waveform that can be compared with another waveform to obtain comparison results that provide information about the other waveform; reference waveforms are often obtained in advance of a comparing operation, but could possibly be concurrently generated from some sort of reference event. The comparing operation in box 42 includes time-scaling, which can be performed on one or more of the set of waveforms, and which makes it possible to extract motion-independent information about object 10 from the sensing results.

As explained in greater detail below, the operation in box 42 can be implemented with a comparing operation such as correlation on two waveforms, and one or both of the waveforms can be time-scaled before they are compared. For example, in a brute-force approach, a variety of different time-scalings can be performed to find the time scale at which correlation or anti-correlation is maximized, if at all. In a more elegant approach, it may be possible to discover an appropriate time-scaling from other information, in which case time-scaling may only need to be performed once to obtain near-maximal correlation or anti-correlation results. The operation in box 42 uses sensing results to obtain at least part of the encoded motion-independent information, and can therefore also be referred to as a "decoding" operation. The results of decoding can be used in a wide variety of ways, some of which are described below in relation to specific implementations.

The operation represented in box 44 obtains a periodicity value such as frequency or wavelength from at least one of the sensed time-varying waveforms, and uses the periodicity value in obtaining at least part of the encoded information about object 10, so that it is also a decoding operation. The operation in box 44 could, for example, include a "transforming operation", used herein to refer to an operation that converts between a time-varying signal and a frequency spectrum, also referred to as a "transform"; the Fourier transform is an example of a transforming operation, but the expression broadly encompasses a variety of operations that obtain transforms, including various digital approximations such as a fast Fourier transform (FFT) operation.

Decoded information about an object, as obtained by the operations in boxes 42 and 44, can be used for a wide variety of purposes. In exemplary implementations described below, such information can indicate types of objects, and therefore can be used to distinguish objects. As indicated by the words "AND/OR" within box 40, the operations in boxes 42 and 44 can be performed separately or together, and some of the exemplary implementations described below provide examples of these possibilities; as indicated by dashed arrow 46, for example, the operation in box 44 can be performed to obtain a scaling factor that is then used by the operation in box 42 to perform time-scaling, obtaining information about position or spectrum of objects and thus about types of objects.

Encoding/sensing arrangement in FIG. 1 could be implemented in many different ways, some of which are described below. In particular, excitation arrangements and filter arrangements can be used to encode information in time variation of emanating light, which can then be sensed by photosensors.

In some exemplary implementations below, for example, an excitation pattern includes a longitudinal sequence of excitation regions of different colors. As a result, emanating light from different regions will have different intensities, depending on the spectrum of light emanating from an object in response to each region's color, so that time variation of the output light encodes information about the excitation spectrum, i.e., about the type of the object.

Similarly, in some exemplary implementations below, a filter assembly can have a longitudinal sequence of band pass filter elements with bands of different colors. As a result, output light from filter elements of different colors will have different intensities, depending on the spectrum of light emanating from an object, so that time variation of the output light encodes information about the object's position and the emanating light's spectrum, i.e. about the type of the object.

Longitudinal sequences of excitation regions of different colors or of filter elements of different colors can also be used to encode motion-dependent information about objects. For example, information about speed or other displacement rate can be encoded by such longitudinal sequences. In particular, a periodic longitudinal sequence can be used to encode speed-dependent information.

In some exemplary implementations below, for example, a stack or stack-equivalent filter assembly combines a periodic or chirp transmission function that can encode information about an object's position, speed, or other displacement rate with a random transmission function that can encode information about an object's spectrum or type. Emanating light passing through the filter assembly is concurrently encoded with both types of information.

In other implementations that do not employ emanating light, an encoding/sensing arrangement can include a patterned sensing arrangement, meaning an arrangement of two or more sensors that, in combination, provide sensing results in which information about an object is encoded. For example, a patterned photosensing arrangement can include photosensors in an appropriate pattern to provide such sensing results when receiving light emanating from an object, while a patterned impedance-based sensing arrangement can include electrodes, inductors, or other components in an appropriate pattern to provide such sensing results when interacting with an object.

Figure 2:
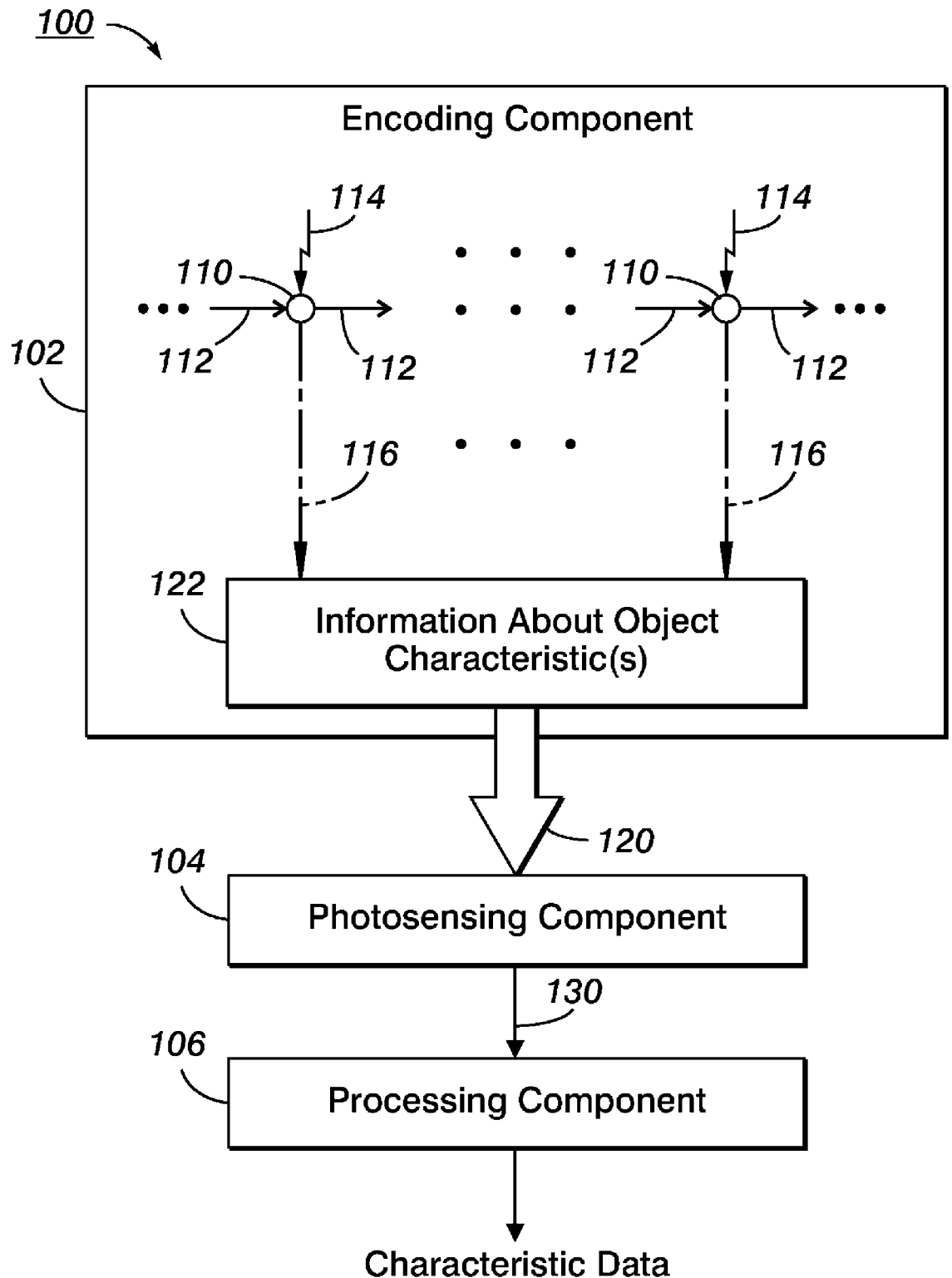
FIG. 2 is a schematic diagram showing components of a system in which light emanating from an object can include information about characteristics of the object.

FIG. 2 schematically illustrates general features of system 100, a system in which light emanating from a moving object can include information about characteristics of the object and in which features described above in relation to FIG. 1 can be implemented. As with other exemplary implementations described below, system 100 involves a combination of parts or components. Encoding component 102 illustratively provides output light that includes information about one or more object characteristics. Photosensing component 104 responds to the output light, providing sensing results such as electrical output signals with information in a form that can be communicated to processing component 106, possibly after conversion to other forms, e.g. for storage, transmission, and processing, such as optical or other electromagnetic signal forms. Processing component 106 can use the sensing results from photosensing component 104 to obtain and/or provide characteristic data indicating information about one or more object characteristics.

Object 110 illustratively travels in a direction indicated by arrows 112, passing through a succession of positions, two of which are illustrated. In some positions, object 110 can receive excitation, illustrated by arrows 114, and, in response, light as illustrated by arrows 116 can emanate, such as from fluorescence of a dye or other "tag" attached to object 110 or from native fluorescence or autofluorescence of object 110 itself, e.g. due to ultraviolet light or other excitation of intrinsic cell material or other material in object 110; except as otherwise noted, however, implementations described herein can additionally or alternatively employ chemofluorescence, biofluorescence, absorption, scattering, or other phenomena that do not require concurrent excitation. More generally, excitation could take any appropriate form and is not limited to illumination, and excitation and emanation need not be concurrent or otherwise coincident, but could have any appropriate relationship in space and time. Some examples of excitation are described below in relation to exemplary implementations.

Arrow 120 represents output light from encoding component 102. Box 122 between arrows 116 and arrow 120 illustrates that information about one or more characteristics of object 110 is included in the output light. As described below in relation to exemplary implementations, this information can be encoded in a variety of ways, including, for example, patterning excitation and/or patterning emanating light to obtain encoded output light represented by arrow 120.

Arrow 120 points to photosensing component 104, indicating that at least part of the encoded output light is illustratively sensed by component 104 to obtain sensing results. Based on the sensing results, component 104 provides electrical output signals represented by arrow 130. The electrical output signals can also include at least some of the information about object characteristics from box 120. As a result, processing component 106 can, in response to the electrical output signals, obtain and/or provide characteristic data indicating information about object characteristics.

Figure 3:
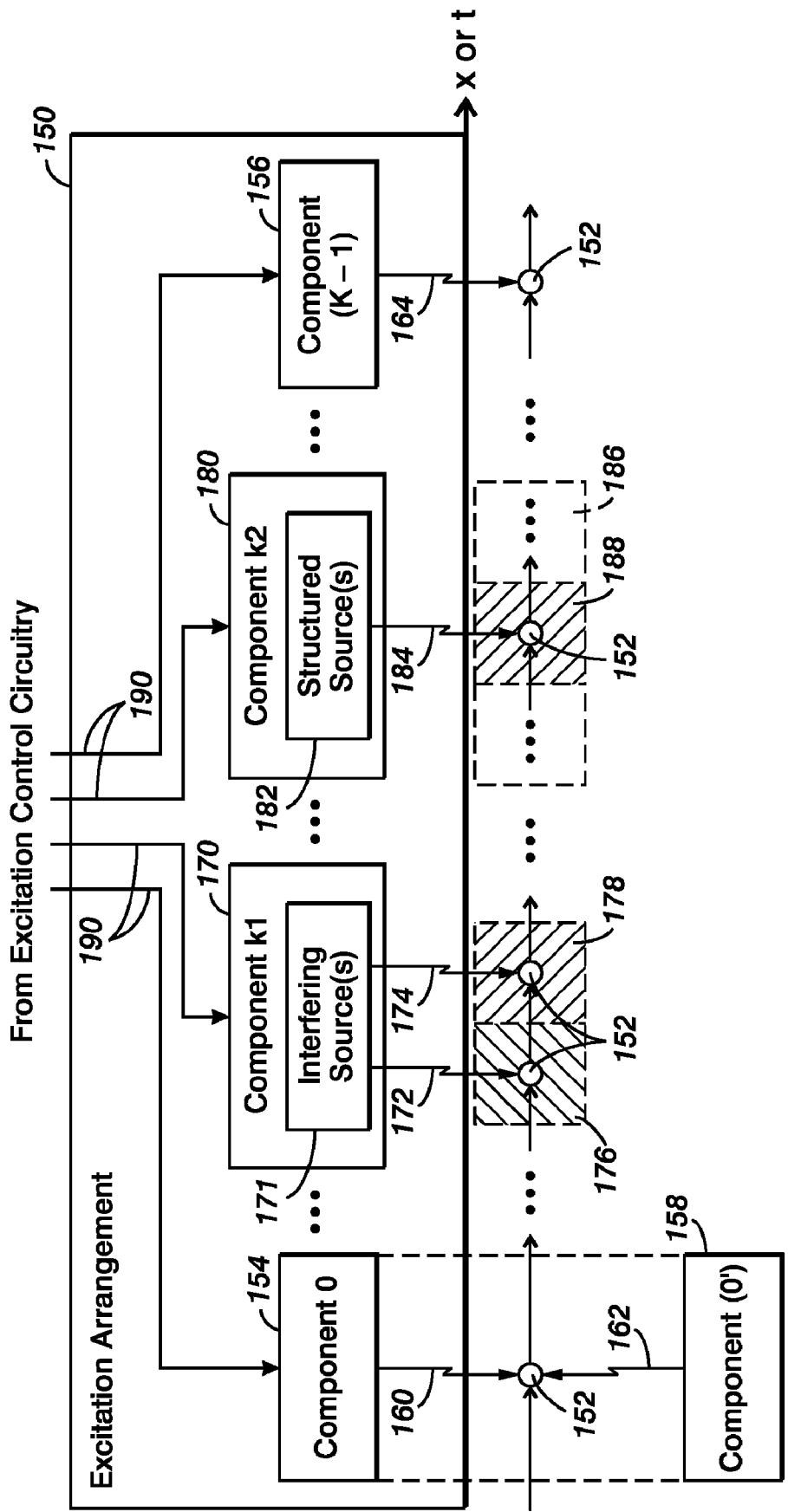
FIG. 3 is a schematic diagram of an excitation arrangement in an encoding component as in FIG. 2.
Figure 4:
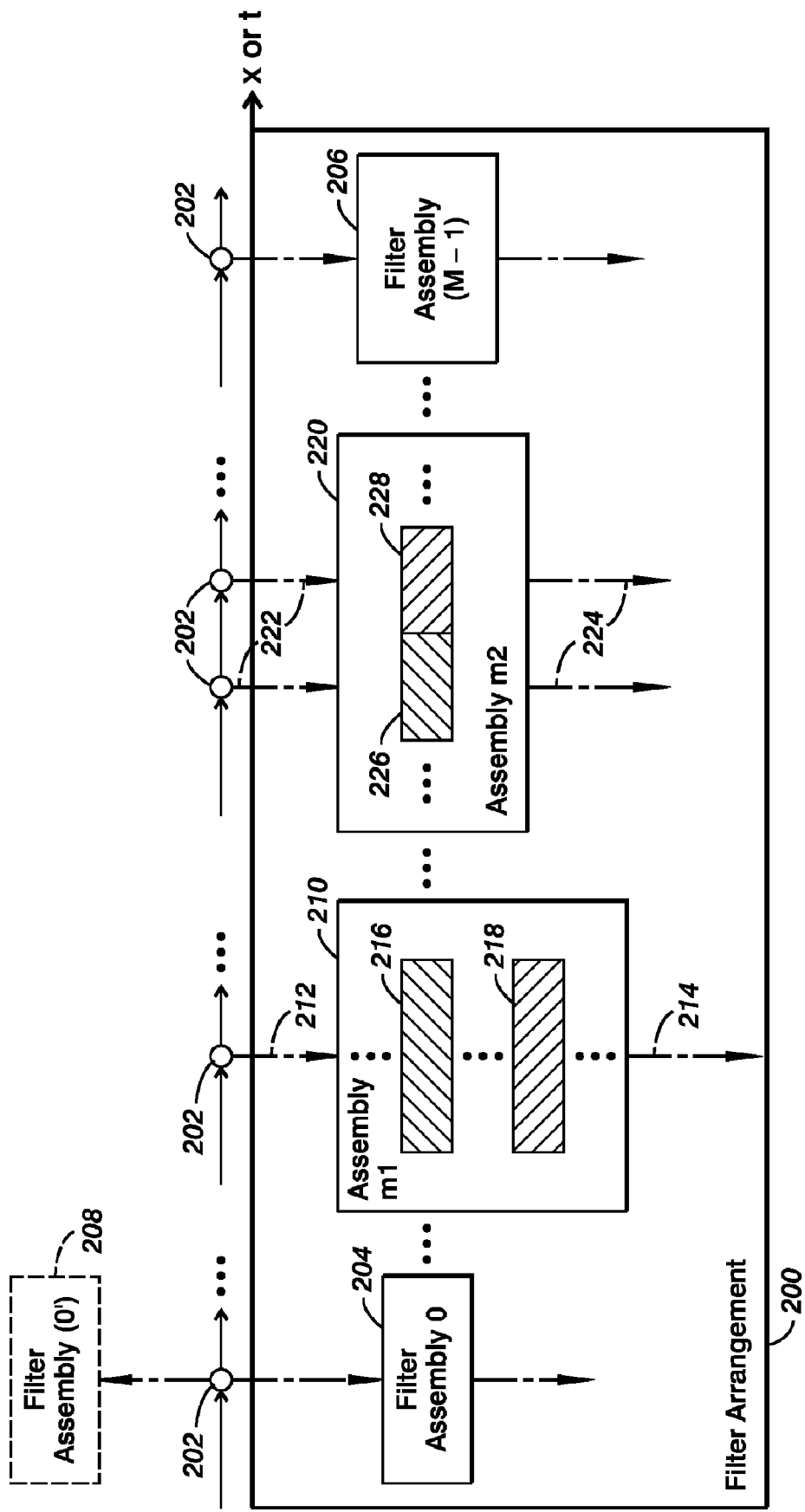
FIG. 4 is a schematic diagram of a filter arrangement in an encoding component as in FIG. 2.
Figure 5:
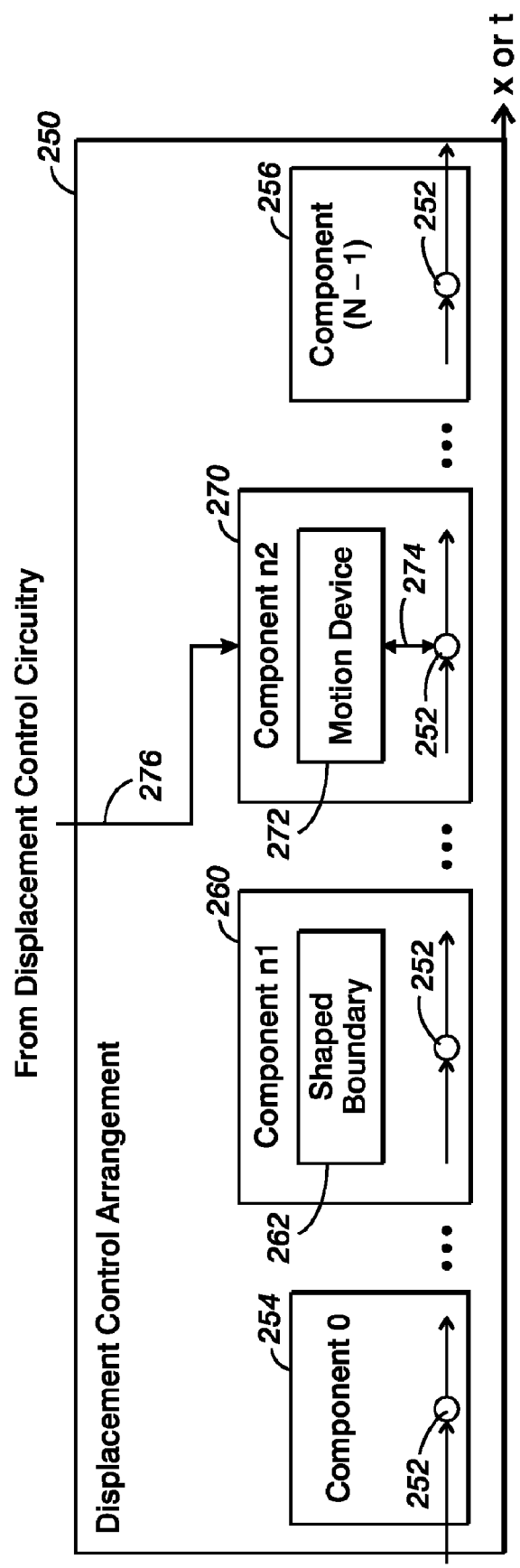
FIG. 5 is a schematic diagram of a displacement control arrangement in an encoding component as in FIG. 2.

Each of components 102, 104, and 106 in FIG. 2 could be implemented in a wide variety of different ways. FIGS. 3-5 illustrate several general features of implementations of encoding component 102, each of which involves an arrangement along a path traveled by a moving object.

In FIG. 3, excitation arrangement 150 is along a path traveled by moving object 152 as it emanates light within an encoding component such as component 102 in FIG. 2. As suggested by the one-dimensional coordinate axis labeled "x OR t", the path can be treated either as extending in space, such as along an x-direction, or as occurring over time, t; unless otherwise indicated hereafter in relation to a specific exemplary implementation, the x-direction refers to an object's path and therefore might not in some cases follow a straight line relative to the environment. Although the speed or other rate of displacement of object 152 may vary as it travels along the path, information about its speed or other rate of displacement can be sufficient to allow an approximate mapping between its x-direction positions and times t; more generally, mapping between an object's x-direction positions and times t can be based on any suitable system, such as with trigger detection techniques as described in U.S. Patent Application Publication No. 2007/0145249, entitled "Sensing Photons from Objects in Channels", incorporated herein by reference in its entirety, or from other techniques, including obtaining information such as a trigger signal from an object's encoded signal.

The term "excitation component" refers herein to a part or component that provides excitation of any appropriate type, in response to which objects emanate light. For example, illumination of various kinds can cause objects to emanate light, so that many excitation components are light sources. Other types of excitation can also be provided, within the scope of the techniques described herein.

Excitation components can be combined and configured in many different ways, and all such combinations and configurations are encompassed herein by the general term "excitation arrangement". Some specific examples included herein employ interference in light from one or more light sources, and are therefore referred to as "interfering sources", while others involve structures that include one or more light sources and that provide a pattern of illumination, referred to herein as "structured sources". Within a given configuration of excitation components, relationships can be described in several ways. Of particular relevance is the pattern of illumination that can be produced, such as interfering sources or structured sources; such a pattern can include "excitation regions" and/or "excitation patterns"; the terms "excitation pattern" and "excitation region" are related, in that an excitation pattern includes one or more excitation regions, while an excitation region generally does not include other excitation regions within it. If a path travels through a "longitudinal sequence" of excitation regions, it passes through each of the regions on a respective segment of its path.

Several categories of longitudinal sequences of excitation region are described below in relation to exemplary implementations, including periodic patterns, chirp patterns, random patterns, and so forth, and various other categories could be identified. As used herein, the term "random" refers to a pattern that is non-periodic over the entire length of a longitudinal sequence of excitation regions; in contrast, a "periodic" sequence has at least one pattern that repeats more than once across the sequence's longitudinal length; and "chirp" sequences meet the above definition of random but can, with linearly varying time-scaling, meet the above definition of periodic, in effect being a sequence of periods of linearly changing frequency or wavelength. Any of these types of excitation sequences can be used to obtain "spatially modulated" emanating light, meaning emanating light that varies in time depending on position of an object from which it is emanating.

Although excitation components could be positioned in any appropriate way along a path, the exemplary implementations described below generally involve arrangements of one or more excitation components along the x OR t axis, and FIG. 3 shows several exemplary components within a sequence of K excitation components 154 through 156, with component 154 labeled "0" and component 156 labeled "(K−1)". Excitation components need not, however, be arranged on only one side of the path, but rather could be positioned at any suitable positions around the path, depending on how excitations from different components interact. Also, two or more excitation components could be at the same position or in overlapping position ranges along the x OR t axis, but displaced in a rotation direction; a configuration of excitation components that are sufficiently displaced in a rotation direction so that they are around the path is illustrated by component 158, representing a possible position of another excitation component labeled "(0')" in arrangement 150, on the opposite side of the path traveled by object 152 from component 154.

Arrow 160 schematically represents excitation from component 154, while arrow 162 represents excitation from component 158. Similarly, arrow 164 represents excitation from component 156. Although excitation from components 154 and 158 can be provided concurrently to object 152, as suggested by arrows 160 and 162, excitation from component 156, represented by arrow 164, is provided at a subsequent position and time of object 152.

Excitation component 170, labeled "k1", illustratively includes one or more interfering light sources 171, resulting in two or more different types of excitation, with two types represented by arrows 172 and 174. The excitation represented by arrow 172 occurs while object 152 travels along a segment of the path through region 176, while the type of excitation represented by arrow 174 occurs while object 152 travels along a subsequent segment of the path through region 178. Regions 176 and 178 therefore form a pattern in space, an example of "spatially patterned excitation" used herein to refer to excitation that occurs in a pattern in space, i.e. a "spatial pattern"; spatially patterned excitation could, for example, include multiple periods of a spatial pattern. In particular, the excitation in region 176 has a different photon energy spectrum than the excitation in region 178, so that regions 176 and 178 could be described as having "different colors" of excitation. Several specific examples in which spatially patterned excitation includes regions of different colors are described below in relation to exemplary implementations; as will be understood from some of the examples, the x-direction of a path as shown in FIG. 3 may not follow a straight line, so that regions 176 and 178 may not in fact be oriented along a straight line through components 154 through 156—in some implementations, regions 176 and 178 could each extend parallel to such a line and the path could go back and forth between regions 176 and 178.

Excitation component 180, labeled "k2", illustratively includes one or more structured light sources 182. In other words, light sources 182 are structured to provide spatially patterned excitation, represented by spatial pattern 186. In the illustrated example, arrow 184 represents excitation provided in region 188, one of a pattern of regions through which object 152 passes while receiving excitation from component 180. The complete pattern of regions is represented in FIG. 3 by pattern 186.

FIG. 3 also illustrates lines 190 through which each of components 154 through 156 can receive control signals from excitation control circuitry (not shown). For example, one or more of the components in excitation arrangement 150 could include trigger detecting circuitry (not shown) as described above, and the excitation control circuitry could, in response to the trigger detecting circuitry, provide control signals causing the component to provide excitation, either in a steady state or time-varying manner. As described below in relation to exemplary implementations, time-varying excitation can encode information in a way similar to spatially patterned excitation.

In FIG. 4, filter arrangement 200 is similarly along a path traveled by moving object 202 as it emanates light within an encoding component such as component 102 in FIG. 2. Filter arrangement 200 includes a combination of one or more filter assemblies along the path traveled by object 202.

The term "optical filter" or simply "filter" refers herein to a light-transmissive part or component that transmits light in accordance with a respective criterion, sometimes referred to herein as a filter's "type". For example, one general category of filters is "band pass filters", referring to types of filters that, across some application's range of photon energies, e.g. a range of wavelengths or frequencies such as the visible range, preferentially transmit light within a subrange, sometimes referred to as a "band"; a band pass filter's type can therefore be specified by specifying the band or subrange of photon energies in which it transmits. A "blocking filter", which does not transmit any light in an application's range, can be viewed as a band pass filter with a band of zero bandwidth, while a "transparent filter", which transmits all light in an application's range, can be viewed as a band pass filter with a band that includes the entire range.

Filters can be combined and configured in many different ways, and all such combinations and configurations of one or more filters are encompassed herein by the general term "filter arrangement". A filter arrangement can include, for example, one or more "filter components", one or more "filter assemblies", and/or one or more "filter elements"; while the term "filter component" is generic, referring to any component that operates as a filter, the terms "filter assembly" and "filter element" are related and therefore a bit more specific, in that a filter assembly is a filter component that includes one or more filter elements, while a filter element is a filter component that generally does not include other filter elements within it. In general, filter elements and filter assemblies are sometimes also referred to as "masks".

Filter elements of various kinds could be included in filter assemblies, filter components, filter arrangements, and other combinations and configurations of filters, in a wide variety of ways. Within a given configuration of filters, relationships between filters can be described in a number of ways. For example, light can pass through a "sequence" of filters, meaning that specified light passes through the filters in a sequence: If a "radial sequence" of filters is along a path, for example, emanating light can pass through each of the filters in the sequence, beginning with the first and, after passing through each preceding filter, passing through the following filter; of course, light that is blocked by a preceding filter in a radial sequence would not reach its following filter. If a "longitudinal sequence" of filters is along a path, on the other hand, light emanating at each of a sequence of segments of the path passes through a respective filter in the longitudinal sequence.

Several other categories of filters are described below in relation to exemplary implementations, including shadow masks, periodic masks, chirp masks, random masks, and so forth, and various other categories could be identified. As used herein, the term "random" refers to a pattern that is non-periodic over the entire length of a longitudinal sequence of filters; in contrast, a "periodic" filter assembly has at least one pattern that repeats more than once across the assembly's longitudinal length; and "chirp" patterns meet the above definition of random but can, with linearly varying time scaling, meet the above definition of periodic, in effect being a sequence of periods of linearly changing frequency or wavelength. A "shadow mask" is not a band pass filter, but rather an intensity-based filter assembly that, within a photon energy range of interest, transmits light of all energies, but with different parts of the filter transmitting the light at different intensities, such as black and white and/or different gray scales. Any of these types of filter assemblies can be used to obtain "spatially modulated" emanating light, meaning emanating light that varies in time depending on position of an object from which it is emanating.

Although filter assemblies could be positioned in any appropriate way along a path, the exemplary implementations described below generally involve arrangements of filter assemblies along the x OR t axis, and FIG. 4 shows several exemplary cross sections of filters within a sequence of M filter assemblies 204 through 206, with each cross section being taken parallel to the x OR t axis and with assembly 204 labeled "0" and assembly 206 labeled "(M−1)". Filter assemblies need not, however, be arranged on only one side of the path as shown, but rather could be positioned at any suitable positions around the path, depending on directional intensity variations of emanating light. Also, two or more filter assemblies could be at the same position or in overlapping position ranges along the x OR t axis, but displaced in a rotation direction; a configuration of filter assemblies that are sufficiently displaced in a rotation direction so that they are around the path is suggested by box dashed-line box 208 in FIG. 4, representing a possible position of another filter assembly labeled "(0')" in arrangement 200, on the opposite side of the path traveled by object 202 from filter assembly 204.

Filter assembly 210, labeled "m1", illustratively includes a radial sequence of filters through which light emanating from object 202, represented by arrow 212, can pass, with the output light from filter assembly 210 being represented by arrow 214. Filter assembly 210 could include any appropriate number of filters, with filters 216 and 218 being shown in FIG. 4.

The overall sequence of filter assemblies 204 through 206 illustrates a longitudinal sequence. Further, filter assembly 220 includes a longitudinal sequence of filters through which light emanating from object 202, represented by arrows 222, can pass, with the output light from filter assembly 220 being represented by arrows 224. Filter assembly 220 could include any appropriate number of filters in any appropriate longitudinal sequence, with adjacent filters 226 and 228 being shown in FIG. 4. Each of filters 226 and 228 could, for example, be a band pass filter, with the bands of filters 226 and 228 being sufficiently different to provide useful information about an emanation spectrum of object 202. Such a filter assembly is sometimes referred to herein as a "spatially patterned filter", because the filters it includes can be treated collectively as a single filter that has a pattern that varies as a function of position. Several examples of spatially patterned filters are described below in relation to exemplary implementations, and one or both of filters 216 and 218 in assembly 210 could also be implemented as a spatially patterned filter.

In the specific example of filter assembly 220, output light per arrows 224 can include encoded information from filters 226 and 228, and the encoded information can be recovered by photosensing the output light and performing appropriate operations on the sensing results. In general, filters 226 and 228 and other filters in filter assembly 220 can have any suitable lengths in the x OR t direction that allow recovery of the encoded information by photosensing and signal processing, including lengths smaller than the apparent extent of object 202 in the x OR t direction that may result in some loss of resolution analogous to blurriness or smearing. As described in relation to some exemplary implementations below, however, each of filters 226 and 228 can have length in the x OR t direction greater than or equal to an apparent extent of object 202 in the x OR t direction, while the lengths of filters 226 and 228 (and other filters in assembly 220) can be sufficiently small that characteristics of object 202 indicated by emanating light do not change while object 202 is traveling past assembly 220. In some specific implementations, filters 226 and 228 have parallel sides extending in a direction transverse to the path, and an assembly of such filters is sometimes referred to herein as a "striped filter" in which each stripe can be specified by filter type and its length (or width) in the lengthwise direction.

Filter arrangements similar to those shown in FIG. 4 may find application not only in fluidic implementations as described below but also in implementations in which objects in an array move relative to other components due, for example, to scanning movement. One such area of application is in image scanning, such as with scanning sheets of paper or other media that can bear images. In particular, object 202 could be a colored spot on a sheet of paper or other medium, and a filter arrangement could be used to obtain information about small differences in color of light emanating from object 202, e.g. color of reflected light in response to broadband illumination. Such information could be used to obtain position and/or color of object 202; for example, if object 202 is a registration mark with a color unique to registration marks, its color could be accurately distinguished from spots of other colors using techniques as described herein and its position could be obtained with sufficient accuracy to allow registration of the sheet, whether for image sensing or for printing or another operation on the sheet. Very high accuracy sensing of color is sometimes referred to as "hyperspectral color sensing".

In FIG. 5, displacement control arrangement 250 is similarly along a path traveled by moving object 252 as it emanates light within an encoding component such as component 102 in FIG. 2. Displacement control arrangement 250 includes a combination of one or more displacement control components, each of which is illustratively shown enclosing a respective segment of the path traveled by object 252. It would, of course, be possible to implement display control components in other ways, such as where an object travels along a path that is not enclosed within a channel or fluidic structure.

Although displacement control components could be positioned in any appropriate way along a path, the exemplary implementations described below generally involve arrangements of displacement control components along the x OR t axis, and FIG. 5 shows several exemplary components within a sequence of control components 254 through 256, with component 254 labeled "0" and component 256 labeled "(N−1)". Although each displacement control component in the sequence illustratively contains a respective segment of the path, it may be possible to implement displacement control components that affect displacement in overlapping segments of a path or that interact in other ways.

Control component 260, labeled "n1", illustratively includes shaped boundary 262, meaning that a boundary that extends partially or completely around the path, such as the boundary of a fluidic channel, has a shape that affects or controls displacement of object 252 as it travels along the path, such as by affecting its speed or other rate of displacement. Several examples of boundary shapes are described below in relation to exemplary implementations.

Control component 270, labeled "n2", illustratively includes motion device 272. Device 272 can illustratively cause lateral motion of a boundary in its segment of the path, as suggested by bidirectional arrows 274. Line 276 shows that device 272 can receive control signals from displacement control circuitry (not shown). Component 270 could also include trigger detecting circuitry (not shown), and the displacement control circuitry could respond to the trigger detecting circuitry by initiating operation of device 272, either in a steady state or time-varying manner. Examples of how device 272 could be implemented are described below in relation to specific implementations.

Figure 6:
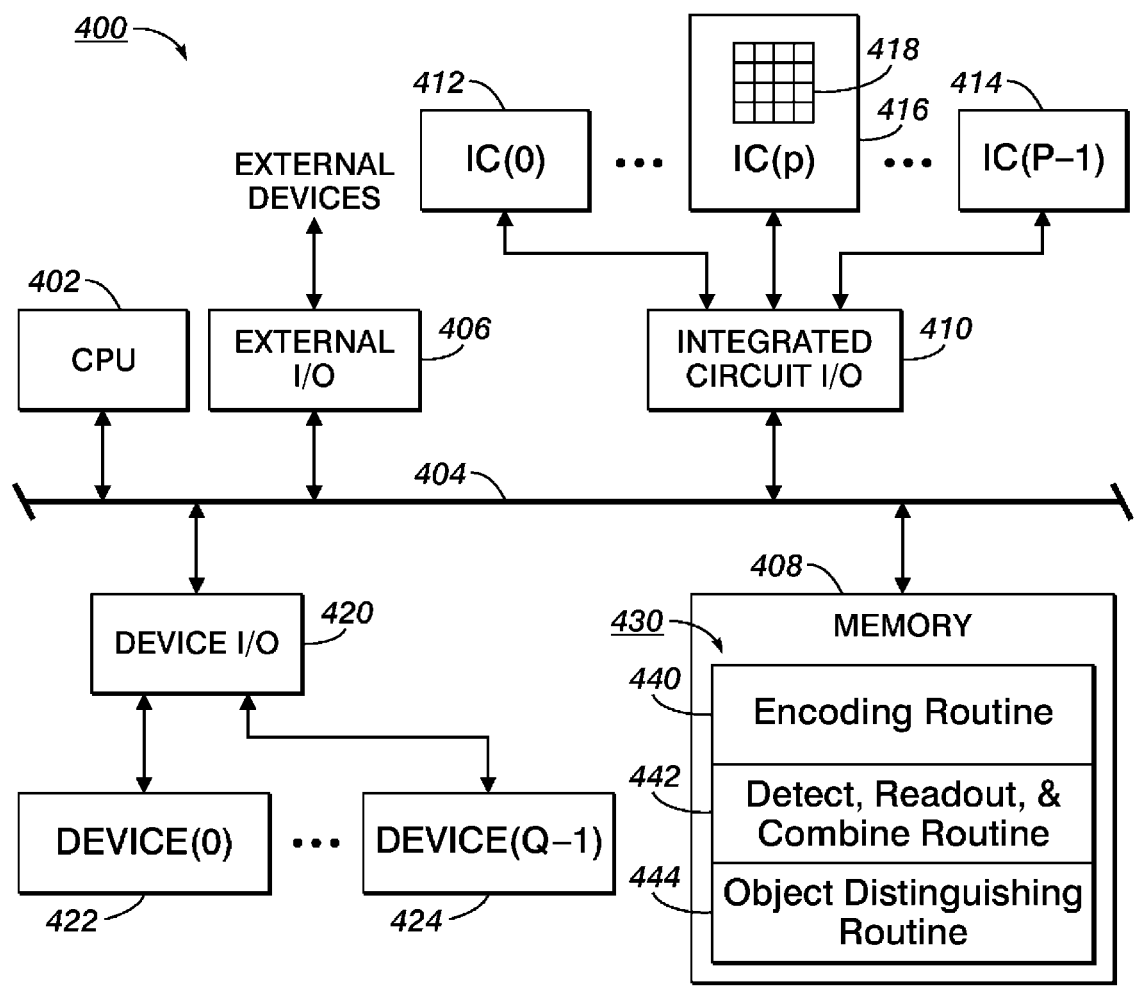
FIG. 6 is a schematic block diagram of a system in which components as in FIG. 2 can be implemented.

FIG. 6 illustrates system 400, an exemplary system that could implement components as in system 100 in FIG. 2. Although system 400 illustratively includes central processing unit (CPU) 402 connected to various components through bus 404, a wide variety of other architectures could be employed, including any appropriate combination of hardware and software, as well as specialized hardware components such as application specific integrated circuits (ASICs) for one or more of the illustrated components or in place of a software component executed by CPU 402. Furthermore, CPU 402 could be the CPU component of any suitable machine such as a laptop or desktop computer, a specialized computer for system 400, and CPU 402 and other digital components as shown could be replaced by other specialized circuitry, such as an analog signal processor; in a relatively simple application, CPU 402 could be implemented with a single digital signal processor or a CPU of a laptop or other personal computer receiving time-varying signals. On the other hand, in some applications, it may prove advantageous to implement all signal processing with analog circuitry, including operations that compare time-varying waveforms and that obtain their derivatives or other related waveforms, making it possible to replace substantially all the digital components as shown if appropriate.

System 400 also includes external input/output (I/O) component 406 and memory 408, both connected to bus 404. External I/O 406 permits CPU 402 to communicate with devices outside of system 400.

Additional components connected to bus 404 are within or connected to system 400. In the illustrated implementation of system 400, IC I/O 410 is a component that permits CPU 402 to communicate with ICs such as photosensing ICs; M ICs are illustrated in FIG. 6 by a series extending from IC(0) 412 to IC (P−1) 414. ICs 412 through 414 illustratively include IC(p) 416 with a photosensor array 418, which includes photosensing cells. Similarly, device I/O 420 is a component permitting CPU 402 to communicate with various devices in system 400, such as sensing and control devices; Q devices in system 400 are represented in FIG. 6 by device (0) 422 through device (Q−1) 424. In addition to excitation components as described above in relation to FIG. 3 and displacement control components as described above in relation to FIG. 5, devices 422 through 424 can include fluidic devices such as pumps, metering electrodes, smart gates, and other devices for gating and bifurcating, valves, flow or pressure sensors, and so forth. Such fluidic devices could be implemented in various ways; smart gates, for example, could be implemented with MEMS style microgates or by using electromagnetic forces, which are effective because most particles are charged such that an electric field can be used to direct them as desired in a channel.

Memory 408 illustratively includes program memory 430 although instructions for execution by CPU 402 could be provided in various other forms of software or hardware, on or off of CPU 402. The routines stored in program memory 430 illustratively include encoding routine 440; detect, readout, and combine routine 442; and object distinguishing routine 444. In addition, program memory 430 can also store a number of subroutines (not shown) that CPU 402 can call in executing routines 440, 442, and 444.

CPU 402 executes encoding routine 440 to encode information in light emanating from a moving object as it travels a path, i.e. information about characteristics of the object. In doing so, routine 440 can provide receive input signals from and provide output signals to devices 422 through 424. For example, to obtain appropriate motion of the object, CPU 402 can receive signals from sensors, perform computations to determine what fluidic operations are necessary, and then provide signals to activate pumps, metering electrodes, gates, and valves to produce appropriate relative movement between an object and other components of system 400 along its path. CPU 402 can also receive signals from trigger detecting devices and perform computations to determine what control signals to provide to excitation components, motion devices, or other components or devices in order to perform appropriate encoding in emanating light. Several examples of techniques that can be performed by encoding routine 400 are described below in relation to exemplary implementations.

In executing routine 442, CPU 402 can, for example, perform pre-sensing readout, obtain object information and sensing periods, perform sensing readout with sensing periods and analog adjustment, digitally adjust sensing results and store quantities for an object, and combine the quantities for an object to produce its characteristic data. Routine 442 could, for example, call a subroutine implemented as described in U.S. Patent Application Publication Nos. 2007/0145249, entitled "Sensing Photons from Objects in Channels", and 2007/0146704, entitled "Sensing Photons Energies Emanating from Channels or Moving Objects", each of which is incorporated herein by reference in its entirety. Such a subroutine can be implemented for single objects moving past arrays or for spaced multiple objects moving past arrays, provided spacings between objects are sufficient to avoid interference. Also, such a subroutine can follow a general strategy of performing a series of readout operations, after which information for an object is combined and its characteristic data is provided, although it would also be possible to provide the information from each readout operation immediately.

Figure 7:
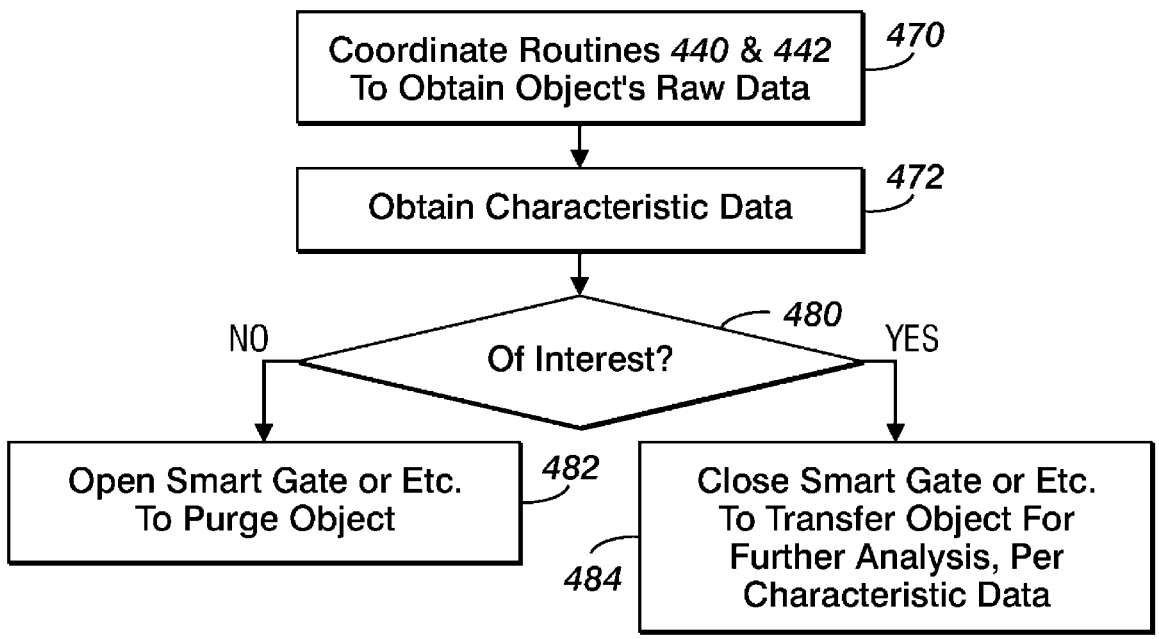
FIG. 7 is a flow chart showing general operations in an implementation of an object distinguishing routine as in FIG. 6.

FIG. 7 illustrates an example of how object distinguishing routine 444 in FIG. 6 could be implemented, using each object's raw data from routine 442 before it is used to obtain characteristic data for the object. Routine 444 can begin with the operation in box 470, which coordinates routines 440 and 442 as described above, obtaining an object's raw data, such as a data structure with photosensed quantities obtained from ICs 412 through 414.

The operation in box 472 receives the raw data from box 470, such as in the form of a handle or other item of data necessary to access a data structure. The operation in box 472 then uses the raw data to obtain the object's characteristic data, such as in one of the ways described below in relation to exemplary implementations. For example, an appropriate comparison technique could be used to obtain a comparison result indicating an object's type or other characteristic. The characteristic data from box 472 can indicate whether the object is of interest for further analysis, such as because it may be suspicious or harmful or, on the other hand, because it may be of interest for more refined analysis.

The operation in box 480 branches based on whether the object is of interest. If not, the operation in box 482 opens a smart gate or provides appropriate control signals to perform another operation to purge the object from the system. But if the object is of interest, the operation in box 484 ensures that the smart gate is closed or provides control signals for other suitable operations to transfer the object downstream so that a more refined or detailed analysis or other further analysis can be performed, possibly after concentration of the object with other similar objects by appropriate fluidic devices.

Figure 8:
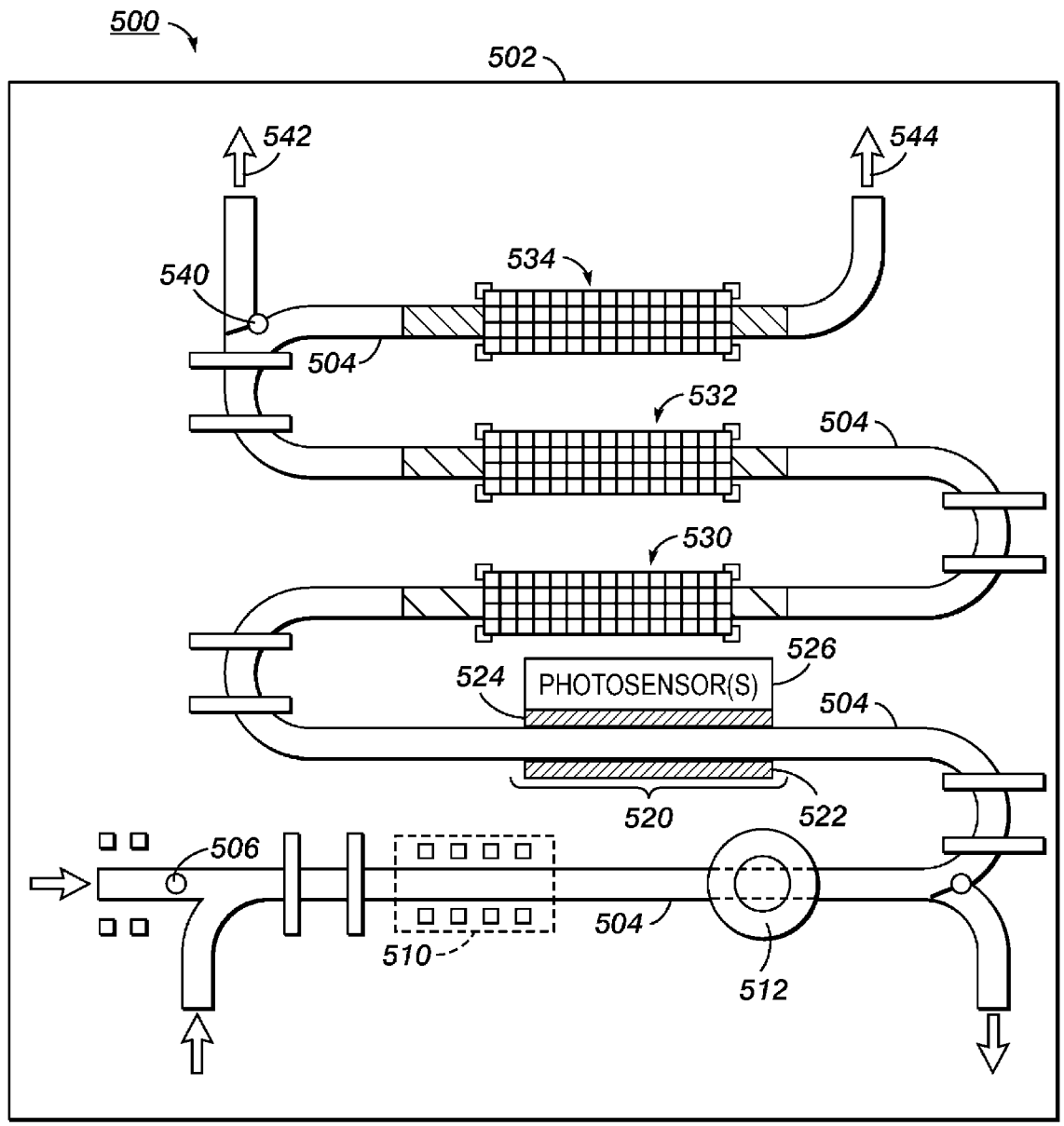
FIG. 8 is a schematic diagram of an analyzer in a fluidic structure, where the analyzer includes a system that can be implemented as in FIGS. 6 and 7.

FIG. 8 illustrates an application of a system as in FIGS. 6 and 7 in analyzer 500 on support structure 502, a fluidic structure. Defined in support structure 502 is serpentine channel 504 through which object 506 can travel, carried by fluid such as liquid, gas, or aerosol or moved in some other appropriate way. Object 506 can, for example, be a biological cell or another object of any of the types mentioned above.

The manner in which object 506 enters channel 504 and is carried by fluid can be the same as described in U.S. Patent Application Publication Nos. 2007/0145249, entitled "Sensing Photons from Objects in Channels", and 2007/0146704, entitled "Sensing Photons Energies Emanating from Channels or Moving Objects", each of which is incorporated herein by reference in its entirety. As explained there, object 506 can be carried through channel 504 by operation of propulsion components and can be purged or otherwise caused to exit, together with fluid that is carrying it, from one of several outlets, such as through toggling of valves. While in channel 504, object 506 can travel through a series of sensing components, each of which can obtain information about object 506.

The first two sensing components after object 506 enters channel 504 are illustratively Coulter counter 510, an electrically based particle size detector, and Mie scatter sensor 512, also a particle size detector. Information about size of object 506 from Coulter counter 510 and Mie scatter sensor 512 can be used in obtaining information about its other characteristics.

The next sensing component along channel 504 is emanating light encoder/photosensor 520, shown schematically in a cross-sectional view along an axis similar to the x OR t axis in FIGS. 3-5, although it would typically be implemented instead with components above and below channel 504, similarly to other sensing components described below. The schematic illustration of encoder/photosensor 520 includes excitation/displacement component 522, filter component 524, and photosensing component 526, all of which might be implemented in a variety of ways, including some of those described above and below.

After passing through encoder/photosensor 520, object 506 could be characterized without obtaining further information, or, as in the illustrated implementation, object 506 can continue through subsequent sensing components, illustratively including components 530, 532, and 534. These could, for example, include first and second fluorescence sensing components and a Raman scatter sensing component. Information obtained from any combination of the sensing components can be used to distinguish between types of objects, such as different types of biological cells, or to distinguish objects from environment or background. Based on such a distinction, valve 540 at a bifurcation junction can be toggled between two positions, with object 506 exiting as indicating by arrow 542 if valve 540 is in one position and exiting as indicated by arrow 544 if valve 540 is in another position.

The fluidic implementation in FIG. 8 is merely illustrative of a wide variety of implementations of the techniques described herein. For example, any appropriate fluidic or nonfluidic techniques could be used with a wide variety of different types of objects and various types of relative motion to gather various types of information about object characteristics.

FIG. 9 illustrates an example of article 600 with components that could be operated similarly to encoder/photosensor 520 in FIG. 8. Some features of article 600 can be understood from description in co-pending U.S. patent application Ser. No. 11/777,712, entitled "Producing Fluidic Waveguides", incorporated herein by reference in its entirety. For example, article 600 includes a "fluidic structure", used herein to refer to a structure that depends for its operation on fluid positioning or fluid flow, such as, for liquids or gases, in response to pressure or, for liquids, as a result of surface tension effects; in general, the term "fluid" is used herein to encompass all media that can flow, including liquids, gases, aerosols, and so forth. The related term "channel" refers herein to any tube or other enclosed passage within a fluidic structure through which fluid flows during operation. A channel is therefore an example of a "fluidic region", used herein to refer to a region that can contain fluid. An operation "positions" fluid in a channel if it changes the fluid's position in any way that leaves the fluid in the channel.

A channel or portion of a channel through which objects can travel along paths are treated herein as having the directional orientation described above in relation to a path. In addition, a "cross section" lies in a plane perpendicular to a direction in which a local net flow of fluid through the channel or portion can occur; a direction in which a cross section extends can be referred to as a "transverse direction" or a "lateral direction." A channel or portion with approximately uniform cross section and substantially linear longitudinal direction can be referred to as "straight", and the channels and portions described herein are generally straight unless otherwise indicated.

In order to contain fluid, a channel or other fluidic region is typically "bounded", meaning that surfaces or surface areas bound it on at least some sides. A "boundary" of a channel or portion is the surface or combination of surfaces within which fluid contained in the channel is confined. A "port" is an opening that extends through the boundary of a channel or portion such that fluid can enter or exit through the port; in general, a port is relatively small compared to the length of the channel or portion, and the boundary is treated as extending across the port as if the port did not exist.

As described below, article 600 can include two light-transmissive components, and FIG. 9 shows article 600 in a top view through one light-transmissive component. In this view, the inner region between the light-transmissive components includes two main portions, channel portion 602 that can contain fluid and non-channel portion 604 that surrounds channel portion 602; channel portion 602 is illustratively shaped like a "T", but could instead have an L-shape or any other suitable shape, including a serpentine shape as in FIG. 8. Ports 608 are openings through one of the light-transmissive components, allowing entry and exit of fluid into and out of channel portion 602.

FIG. 9 also shows filter assembly 610 in dashed outline. Filter assembly 610 is illustratively a spatially patterned filter with a longitudinal sequence of band pass filters that includes filters 612, 614, 616, 618, and 620. Filters 612, 616, and 620 are illustratively cross-hatched similarly to each other to indicate that they have the same or approximately the same band, while filters 614 and 618 are also cross-hatched similarly to each other, illustrating that they also have the same or approximately the same band, a band that is different than that of filters 612, 616, and 620. In other words, filter assembly 610 is a striped filter in which each of filters 612 through 620 can be specified by the band that it passes and its length in the x-direction in FIG. 9.

Surrounding filter assembly 610, blocking material 622 is structured and positioned to provide an aperture. Blocking material 622 can, for example, be a material with approximately zero light transmission that prevents scattering and reflection of light, also preventing light entering filter assembly 610 from nearby fluorescing objects. Blocking material 622 can be produced during the same operation that produces filters 612 through 620 and can in effect be part of filter assembly 610.

The cross section in FIG. 10 shows how light-transmissive components 630 and 632 are separated by material in non-channel portion 604. For example, components 630 and 632 can each include quartz or another suitable material such as glass or acrylic with an appropriate thickness; in a successful implementation, for example, component 630 has a thickness of approximately 0.3 mm, while component 632 has a thickness of approximately 1.0 mm. The distance between them can be approximately 50 μm, maintained by material in non-channel portion 604, which could, for example, be a suitable photoresist material such as SU-8 or another polymer material. Alternatively, a wall (not shown) could be formed around channel portion 602, and non-channel portion 604 could then be filled with epoxy material that seals a lateral boundary around channel portion 602. Various other techniques could be used to produce a similar fluidic structure, including hot embossing, nano-imprinting, or injection molding, and channel portion 602 can have appropriate dimensions, such as for waveguiding as described in co-pending U.S. patent application Ser. No. 11/777,712, entitled "Producing Fluidic Waveguides", incorporated herein by reference in its entirety.

FIG. 10 also shows object 640 from which light is illustratively emanating upward, as illustrated by an emission cone. Although the emission cone is illustratively shown as a single cone, the actual emission cone would depend on angles of total internal reflection at surfaces through which emanating light is transmitted in article 600. FIG. 10 illustrates three alternative filter assembly positions, with filter assembly 642 facing channel portion 602, on the lower surface of component 630; with filter assembly 644 being outside of channel 602 on the upper surface of component 630; and with filter assembly 646 being spaced apart from the upper surface of component 630, adjacent photosensor 648, which could, as in other implementations, be a single, large area photosensor (such as a photo-diode, an avalanche photo-diode (APD), or a photo-multiplier tube (PMT)), or an appropriate array of photosensing cells whose sensed quantities can be combined to obtain a single photosensed quantity, such as an intensity value for a sensing period. As suggested in FIG. 10, the emission cone from object 640 is imaged onto image plane 650 extending through filter assembly 646 by optical component 652, illustratively shown as a single lens, but which could be any suitable lens, lens system, or other optical component, some examples of which are described in co-pending U.S. patent application Ser. No. 11/698,409, entitled "Method and System Implementing Spatially Modulated Excitation or Emission for Particle Characterization with Enhanced Sensitivity", incorporated herein by reference in its entirety.

The emission cone for filter assembly 642 includes the range of angles of incident light that are not totally reflected by the surface of assembly 64. Similarly, the emission cone of filter assembly 644 is determined by the range of angles within which emanating light is not subject to total internal reflection at the surface between component 630 and assembly 644. The emission cone for filter assembly 646 is similar to that for filter assembly 644, but can occupy a smaller area on filter assembly 646 due to the effect of optical element 652.

In one illustrative example, channel portion 602 contains water with an index of refraction n=1.33, and object 640 has a diameter d=7 μm, which would be typical for certain biological cells, e.g. T-lymphocytes. Channel portion 602 has a height between components 630 and 632 of 30 μm and its distance from the lower surface of filter assembly 642 is approximately h=15 μm. Component 630 is acrylic with an index of refraction n=1.48, surrounded by air with an index of refraction n=1. If filter assembly 642 were absent, the escape angle from channel portion 602 to component 630 would be α(escape) =48.75°, which would determine the size of the emission cone in which light from object 640 can leave channel portion 602. The angle of total internal reflection at the upper surface of component 630, on the other hand, can be obtained as α(TIR)=42.51°, which determines the size of the emission cone for light that leaves component 630. The diameter of a disk illuminated by object 640 at the water-acrylic interface can be obtained from D=d+2*h*tan(α(escape))= (7+(2*17.1)) μm=41.2 μm, where 17.1 μm is the radius of the maximum emission cone that can pass through component 630 without total internal reflection. The "minimum feature size" ("MFS") for a pattern suitable to detect object 640 at the water-acrylic interface would be equal to D or approximately 40 μm; in general, MFS can be defined for a mask along the path of an emanating particle as the extent in the path's longitudinal direction of the mask's smallest uniform feature (i.e. the smallest transmitting filter element or the smallest blocking filter element, whichever is smaller).

Where photosensor 648 is implemented with a numerical aperture that makes the emission cone smaller, filter assembly 642 can accordingly have a slightly smaller MFS than calculated as above; similarly, in some acrylic implementations of component 630, some light typically leaves component 630 at an angle slightly higher than α(TIR), which could also allow a slightly smaller MFS. In general, however, the MFS of filter assembly 642, if too small, results in passage of light from an object's emission cone around both sides of a feature in assembly 642, so that the time-varying signal of a photosensor, while containing some information, may not accurately indicate information about displacement of the object as it travels along a path past filter assembly 642. Similar considerations apply to filter assemblies 644 and 646, with the MFS of filter assembly 644 necessarily being significantly larger than that of filter assembly 642, but with the MFS of filter assembly 646 possibly being intermediate between those of assemblies 642 and 644, depending on the precision of optical component 652. In implementations without optical components, photosensor 648 could be slightly larger due to spreading of emanating light. For a biological cell on the order of 10 μm, a typical MFS would be in the range of 10-20 μm. The channel width might be an order of magnitude larger, while the channel length might be two orders of magnitude larger, and the width of the filter assembly would depend on the channel width. For example, assembly 642 might be 100 μm wide and approximately 1.0 mm long. At the time of manufacture, a calibration operation could be performed using objects that are, for example, tiny beads with known fluorescence spectra; light emanating from such beads could be measured and used to obtain calibration values necessary to adjust measured values to obtain known intensities for such objects.

Figure 11:
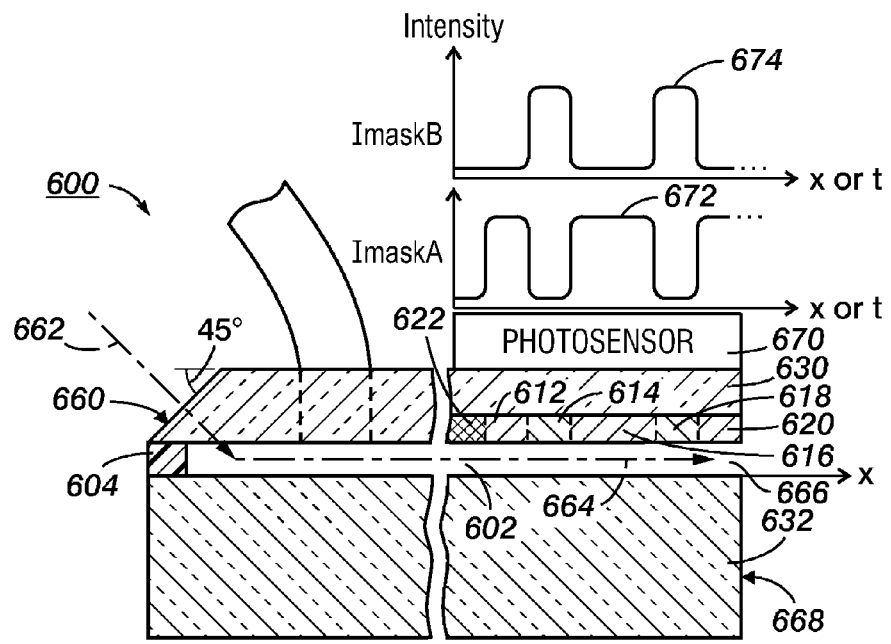
FIG. 11 is a cross-sectional view of another implementation of an article similar to that in FIG. 9, taken along the line 11-11, together with graphs of sensed intensities.

The cross section in FIG. 11 further illustrates how component 630 has oblique surface 660, a light interface surface that is illustratively at an angle of approximately 45° to the inward-facing surfaces of components 630 and 632. As a result, incident excitation light at a direction approximately perpendicular to surface 660, as illustrated by arrow 662, can cause and couple with light propagating through channel portion 602, as illustrated by arrow 664, as described, for example, in co-pending U.S. application Ser. No. 11/777,712, entitled "Producing Fluidic Waveguides", incorporated herein by reference in its entirety. Excitation light could have any appropriate wavelength, such as 266 nm, for example. The distance from surface 660 to obtain appropriate homogeneity can be determined, as described, for example, in U.S. Patent Application Publication No. 2008/0013877, incorporated herein by reference; the distance can also be sufficient to allow integration of blocking material 622.

In the illustrated implementation, the end of channel portion 602 at right in FIG. 11 is open, providing an additional port 666 through which fluid can enter into or exit out of channel portion 602. Alternatively, article 600, instead of ending at transverse end-surface 668, could extend to another area with ports similar to ports 608, such as with a part symmetrical about the position of surface 668; in this case, fluid could flow through channel portion 602 between ports 608 and similar ports at the opposite end of channel portion 602.

In the implementation in FIG. 11, the filters within filter assembly 610 are shown in cross section, and, in this implementation, the filters do not overlap, but rather are adjacent to each other. They could, for example, be integrated into a recess in the lower surface of component 630 such that they are even with the surrounding surface of component 630 or they could be surrounded on all sides by a layer of shadow (light blocking) or transparent material of the same thickness; in either of these approaches, the filters could be implemented so that there is no step at the edges of assembly 610. The size of the gap, if any, between adjacent filters depends, for example, on the resolution of the technique used to produce the filters. If the filters are produced by printing two different light-absorbing materials that have different absorption spectra (in which case a surrounding layer of shadow or transparent material could also be printed around them), the registration and gaps between filters depend on the resolution of the printing technique used; examples of such techniques are described in U.S. Patent Application Publication No. 2007/0172969, entitled "Additive Printed Mask Process and Structures Produced Thereby", and in co-pending U.S. patent application Ser. No. 11/755,717, entitled "Surface Energy Control Methods for Color Filter Printing", each of which is incorporated herein by reference in its entirety. In general, however, the techniques described herein do not require highly precise positioning of filters—a small gap between filters should not significantly affect time-varying signals that result from an object traveling past such filters while it emanates light.

The upper part of FIG. 11 includes two graphs illustrating intensities detected by photosensor 670 in response to two types of objects, one emanating light of color "A", the other emanating light of color "B". Filters 612, 616, and 620 have bands that allow light of color "A" to pass, while filters 614 and 618 have bands that allow light of color "B" to pass.

Curve 672 illustrates intensities indicated by sensing results from photosensor 670 if object 640 emanates light of color "A" as it travels along the path through channel portion 602. In other words, the emanating light's photon energy distribution matches the band for filters 612, 616, and 620 so that curve 672 is high along those filters but low along filters 614 and 618; its high value is indicated on the vertical axis as "ImaskA".

Curve 674, on the other hand, illustrates intensity indicated by sensing results from photosensor 670 when object 640 emanates light of color "B" as it travels along the path. In this case, the emanating light has a photon energy distribution that matches the band for filters 614 and 618 but not for filters 612, 616, and 620, so that curve 674 is at a high intensity along filters 614 and 618, "ImaskB", and at a low intensity elsewhere.

Curves 672 and 674 illustrate an example in which two different types of objects provide signals that are approximately complementary, except at the far left along blocking material 622 where both curves are at approximately zero intensity. In a simple implementation, for example, filters 612, 616, and 620 could be red band pass filters, filters 614 and 618 could be green band pass filters, each object could either be a red fluorescing particle or tag, i.e., emanating light of color "A", or a green fluorescing particle or tag, i.e., emanating light of color "B". As suggested, curves 672 and 674 could be plotted based on the x-direction position of object 640 or based on the t-position within the time varying output signal from photosensor 670, which could be provided continuously or by any suitable form of sampling, such as by periodic readout at an appropriate frequency. The high intensities of curves 672 and 674 would be reduced to the extent that blocking material 622 prevents light from reaching photosensor 670.

As a result, output signals from photosensor 670 can be used to distinguish types of objects, in this case to distinguish objects that emanate light of color "A" from objects that emanate light of color "B", and examples of techniques that distinguish types of objects in various ways are mentioned below in relation to exemplary implementations. In some examples, emanating light encoded by a filter assembly with stripes of random lengths can be analyzed by comparing a resulting time-varying signal with one or more templates or other signals to determine an object's type, displacement, and position to a high level of precision.

Figure 12:
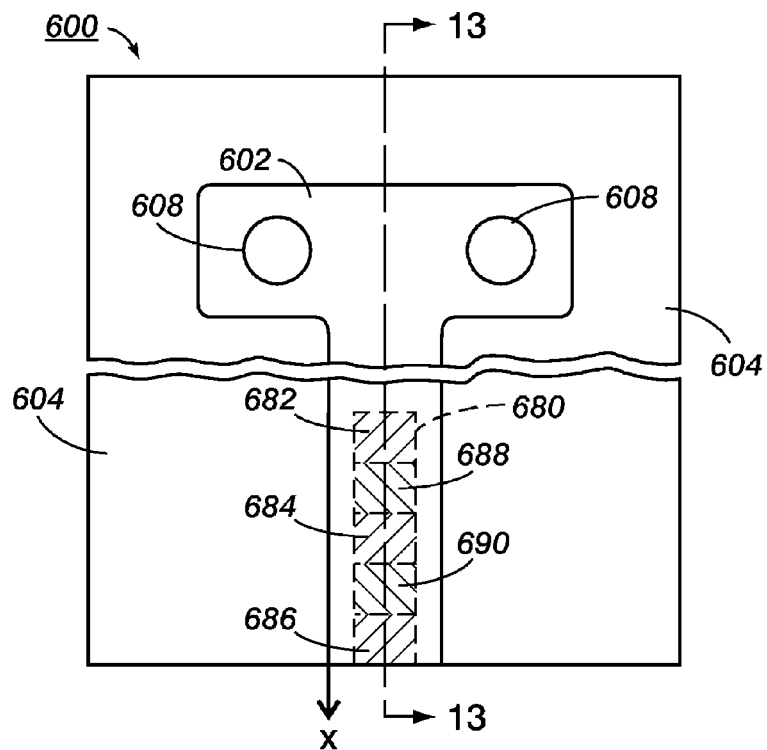
FIG. 12 is a top view of an article that can include an excitation arrangement and that can be included in an encoding component as in FIG. 2.

FIG. 12 illustrates another example of article 600, similar to FIG. 9, but with excitation pattern 680 in dashed outline rather than a filter assembly. Excitation pattern 680 illustratively includes a periodic two-color pattern, with regions 682, 684, and 686 having approximately the same photon energy spectrum in a range of possible excitation energies and with regions 688 and 690 also having approximately the same photon energy spectrum in the range, but different from that of regions 682, 684, and 686, as indicated by the cross-hatching. Each of the regions has approximately the same length in the x-direction in FIG. 12, so that each of the excitation regions 682 through 690 can be characterized by its photon energy spectrum of excitation.

The cross section in FIG. 13 shows how light-transmissive components 630 and 632 can have an appropriate thickness such as approximately 0.3 mm or less; in some implementations, such as if excitation component 692 is a structured light source, component 632 should be as thin as possible in order to reduce distance between the spatially modulated light source and object 640 in the channel. Other dimensions could be similar to FIGS. 9-11 described above, except waveguiding need not be supported.

FIG. 13 also shows excitation component 692, illustratively on the lower surface of component 632 and operating to produce excitation pattern 680. As object 640 travels along a path through channel portion 602, light illustratively emanates from it in response to excitation pattern 680 (FIG. 12). A portion of the emanating light propagates through component 630, reaching photosensor 694; photosensor 694 is illustratively shown on the upper surface of component 630, but could be in any other suitable position, including supported on spacers above the upper surface of component 630 or, component 630 could itself be implemented to be or include a photosensor with a photosensitive surface facing channel portion 602. Photosensor 694 could, for example, be a single, large area photosensor (such as a photo-diode, an avalanche photo-diode (APD), or a photo-multiplier tube (PMT)), or an appropriate array of photosensing cells whose sensed intensities or other quantities could be combined to obtain a single photosensed intensity or other quantity.

The emanating light varies over time as object 640 travels through excitation pattern 680, depending on characteristics of object 640, such as its excitation, fluorescence, absorption, or scattering spectrum. The upper part of FIG. 13 includes two graphs illustrating intensity detected by photosensor 694 as two possible types of object 640 that emanate in response to different excitation colors, referred to as "A" and "B", travel along a path through excitation pattern 680. Curve 696 in the lower graph illustrates the intensity as an object responsive to color "A" travels along the path, responding strongly to the photon energy spectra in excitation regions 682, 684, and 686, but responding weakly if at all to the photon energy spectra in excitation regions 688 and 690. Similarly, curve 698 in the upper graph illustrates the intensity as an object responsive to color "B" travels along the path responding strongly to the photon energy spectra in excitation regions 688 and 690 but responding weakly if at all to the photon energy spectra in excitation regions 682, 684, and 686.

As can be seen, the shapes of curves 696 and 698 are approximately complementary, except at the far left before the path reaches excitation pattern 680, where neither object is emanating light. The maximum intensities of emanation in response to excitations of color A and color B are illustratively labeled as IexcA and IexcB, respectively, and are illustratively approximately equal, but could be different in magnitude. In a simple implementation, excitation regions 682, 684, and 686 could be red colored, having spectra with photon energies predominantly in the red wavelengths, while excitation regions 688 and 690 could be green colored, having spectra with photon energies predominantly in the green excitation wavelengths, and the two types of objects could respond respectively to red and green wavelengths. As suggested, curves 696 and 698 could be plotted based on the x-direction position of object 640, or based on the t-position within the time-varying output signal from photosensor 694, which could be provided continuously or by any suitable form of sampling, such as by periodic readout at an appropriate frequency.

As can be seen from curves 696 and 698, the output signal from photosensor 694 can be used to distinguish types of objects, and computational techniques for doing so are described below in relation to exemplary implementations. Appropriate computational techniques may be used that depend on features of excitation pattern 680. For example, since pattern 680 is periodic, it can provide periodic modulation from which a moving object's speed can be determined, as described below.

As mentioned above, the configurations in FIGS. 9-13 are merely exemplary, and components could be positioned in any suitable way along a fluidic channel. A photosensor could be positioned, for example, as in FIG. 10, spaced from an outer channel surface by spacers or other structures, or operating as one side of a channel, in which case it must be structured so that its photosensitive surface is not damaged or prevented from operating properly by materials in the channel and also so that it provides an appropriate boundary for fluids or other contents of the channel. Similarly, a filter assembly or other filter arrangement could be on a photosensor's photosensitive surface in any of photosensor positions mentioned above, could be positioned in any of the ways shown in FIGS. 10-11, or could be positioned in any other appropriate way. Furthermore, an excitation component could be positioned as in FIG. 13 or similarly to any of the photosensor positions in FIG. 10, or could operate as one side of a channel, in which case it must have a structure that would not be damaged by exposure to materials in the channel and that would confine fluid or other contents of the channel as necessary for operation.

Absorption filters as described above in relation to FIGS. 9-11 can be implemented in a multitude of ways. For example, rather than only two types of band pass filters that have bands for respective colors, three or more types of filters with three or more respective colors could be used. Similarly, a filter assembly can include band pass filters and other types of absorption filters as would be found in a shadow mask. Furthermore, with printed filters as described above or with other filters produced with layers of material, overlapping band pass filters could be produced, providing additional information. In addition, absorption filters could be combined with reflection filters, as described below in relation to some exemplary implementations.

Filter assembly 700 in FIG. 14 illustrates some of these variations. In the illustrated assembly, each stripe is labeled with a description of its filter criterion. Stripe 702 is a red band pass filter; stripe 704 is a closed filter, meaning that it allows no transmission; stripe 706 is an open filter, meaning that it allows full transmission; stripe 708 is a gray filter, meaning that it passes all photon energies across a range of interest, but at an intensity in between an open filter and a closed filter; stripe 710 is a green band pass filter; stripe 712 is a combined band pass filter that passes only the intersection of blue and green; and stripe 714 is a blue band pass filter. In addition, as can be seen, the widths of the stripes are random rather than periodic.

Figure 15:
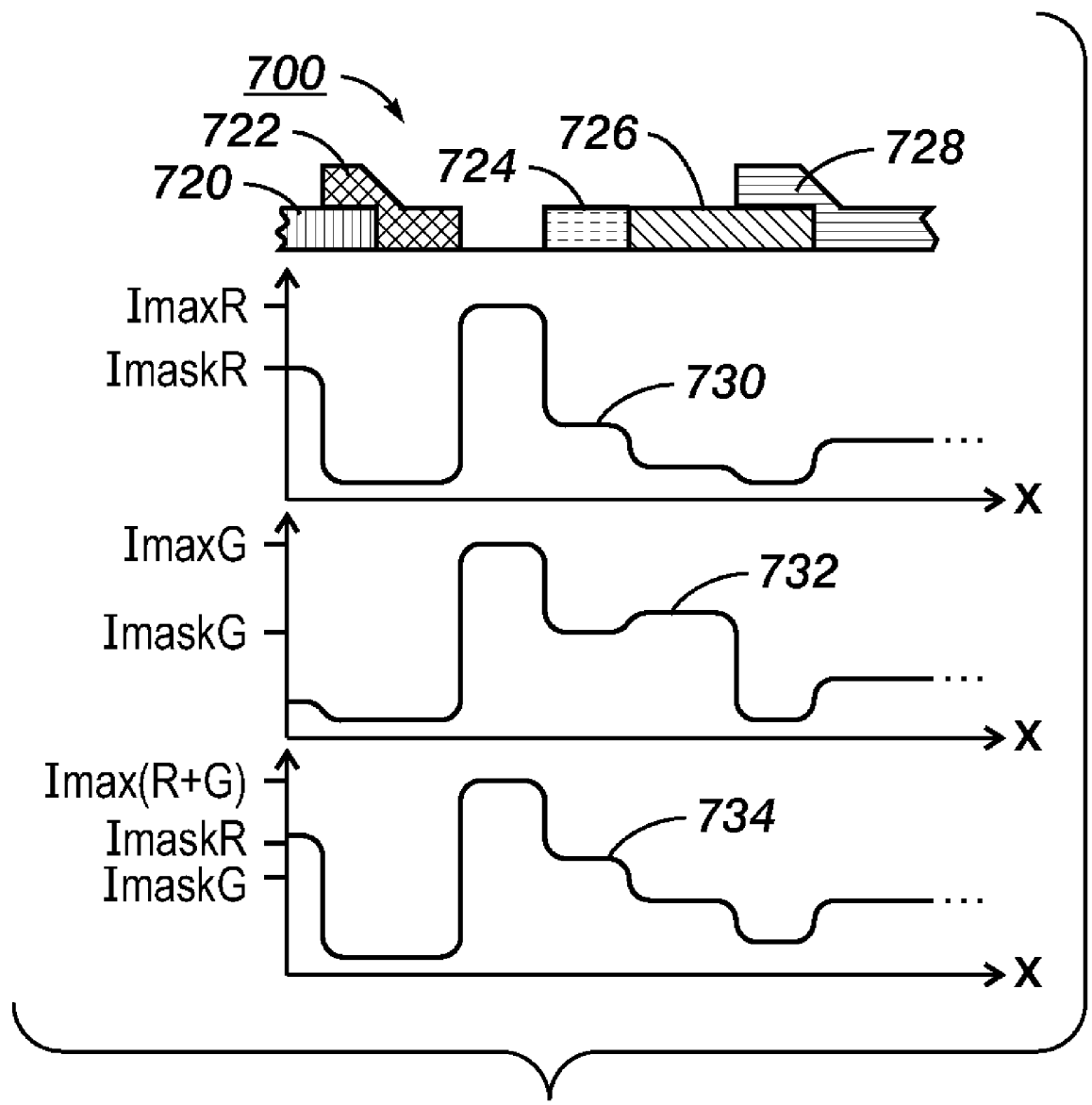
FIG. 15 is a cross-sectional view of an implementation of a filter arrangement similar to that in FIG. 14, taken along the line 14-14, together with graphs of transmitted intensities.

The cross section in FIG. 15 illustrates one way of implementing filter assembly 700 in FIG. 14, illustratively using patterned layers of light absorbing material to produce different types of filters. The implementation in FIG. 15 could, for example, be implemented by printing or otherwise depositing and patterning layers of material as described above.

In the cross section at the top of FIG. 15 filter assembly 700 includes red layer part 720, black layer part 722 overlapping layer part 720, gray layer part 724, green layer part 726, and blue layer part 728 overlapping layer part 726. Where overlaps occur, the result is the intersection of two absorption filters: the intersection of layer parts 720 and 722 is a closed filter, while the intersection of layer parts 726 and 728 is a filter with a band that is the intersection of the bands of the green and blue filters.

The three graphs below the cross section show expected intensity signals similar to those in the graphs in FIG. 11. Curve 730 would be for a red fluorescing particle or tag; curve 732 would be for a green fluorescing particle or tag; and curve 734 would be for an example where object 640 is tagged both with a red and a green fluorescing particle so that curve 734 is a scaled sum of curves 730 and 732. More generally, the technique of FIGS. 14 and 15 would make it possible to distinguish not only red, green, and blue particles and tags, but also objects tagged with combinations such as red and green, green and blue, red and blue, and red and green and blue. Each combination results in a distinguishable time varying signal that can be analyzed to obtain information about the color or colors that are emanating.

Although the intensity signals described above in relation to FIGS. 11, 13, and 15 could be obtained from sensing results of a single, large area photosensor, it would also be possible to use an IC with an array of photosensing cells or an array of discrete photosensors, in either case appropriately positioned along a path traveled by objects past one or more filter assemblies. If an array is used, and each element of the array is covered with a different filter assembly, it may be possible to distinguish many different types of particles concurrently. The number of particles to be distinguished can be much larger than the number of elements in the array, since each measurable distinguishing feature can provide one axis in a principal component analysis, and multiple particles can be distinguished along each such axis. Additional techniques that can be used to track and distinguish objects are described in co-pending U.S. patent application Ser. No. 11/702,328, entitled "Distinguishing Objects", incorporated herein by reference in its entirety. Objects can be distinguished, for example, from their environment or background or from objects of other types; an operation "distinguishes" objects if the operation locates, selects, sorts, counts, or otherwise identifies an object or controls or directs an object according to type or separates objects or otherwise treats objects differently in some way.

Band pass filters of other types can also be used to implement filter assemblies as described in some of the exemplary implementations herein. For example, interference based filters can have different bands similar to the bands described above in relation to FIGS. 9-11 and 14-15.

Figure 16:
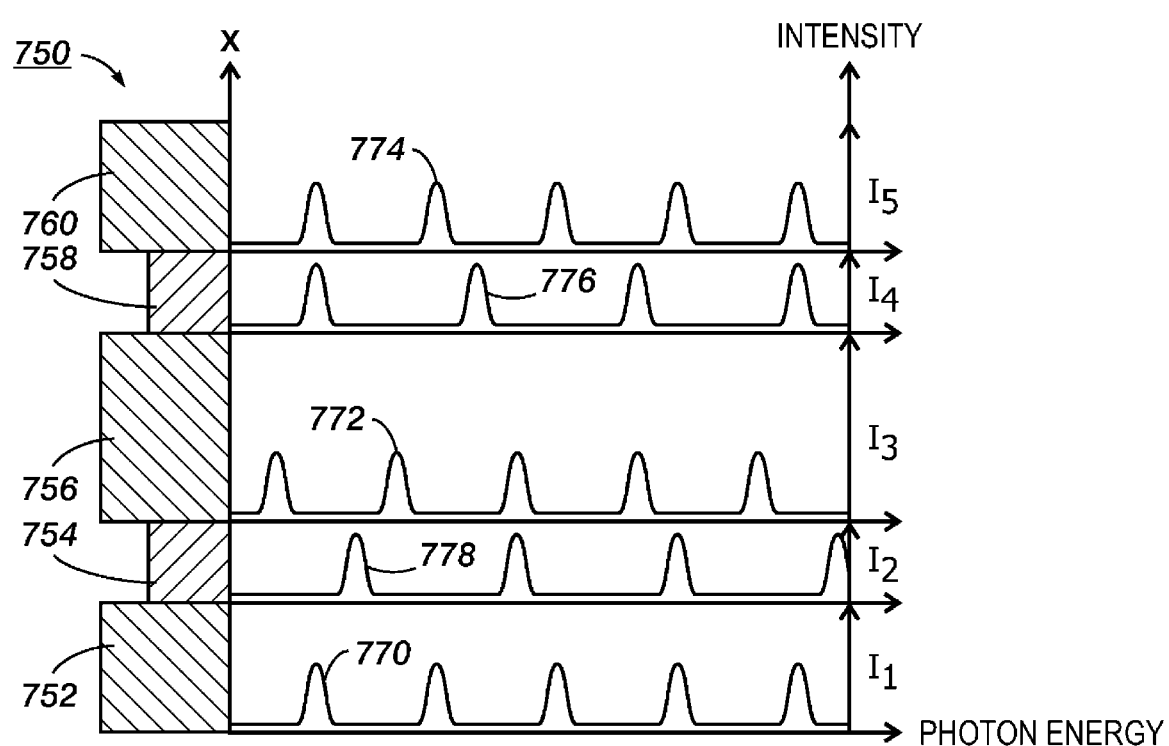
FIG. 16 is a cross-sectional view of another implementation of a filter arrangement that can be included in an encoding component as in FIG. 2, together with graphs showing spectra of transmitted intensities.

Filter assembly 750 in FIG. 16 illustrates an implementation in which a thin layer of transparent material creates Fabry-Perot oscillations, and can be structured to obtain high thickness-dependent index contrast. Assembly 750 includes filters 752, 754, 756, 758, and 760, each of which has substantially constant thickness, but with the thicknesses of filters 752, 756, and 760 being approximately equal to each other while the thicknesses of filters 754 and 758 are approximately equal to each other but smaller. Assembly 750 could be produced, for example, by etching a deposited layer of transparent material or by imprinting a non-solid layer of such material before it solidifies.

To the right of the cross section of assembly 750 is a graph showing an intensity-energy function of its transmitted light. In other words, curves 770, 772, and 774 are approximately the same because filters 752, 756, and 760 have approximately the same thickness. On the other hand, curves 774 and 776 are also similar to each other but different than the others, because the thicknesses of filters 754 and 758 are the same as each other but different than the others. As a result, an object traveling along a path past assembly 750 results in a time-varying signal with changing intensity-energy function. The total transmission at each position will relate to the overlap of the cavity's transmission lines and the particle spectrum. The other part of the emanating light would be reflected from assembly 750, and could also be detected to obtain confirming information. For example, assembly 750 could be on one cover slide of a channel, and two photosensors (not shown) could be positioned, one on the side of assembly 750 away from the channel and the other on the opposite side of the channel to obtain sensing results for the reflected emanating light.

Fabry-Perot interference-based filters could also be structured to obtain band pass filters more nearly similar to those of FIGS. 9-11. Optical thickness of a filter's cavity could vary in the x-direction, and the variation in optical thickness could be produced in any appropriate way. The general strategy would be to provide regions that operate as band pass Fabry-Perot filters, with different sets of filters having transmission peaks at different photon energies. For example, one set of filters could have a transmission peak at approximately 822 nm, while another could have a transmission peak at approximately 833 nm. Such a filter assembly, with upper and lower distributed Bragg mirrors (DBRs) and a cavity between them, could be produced by using techniques described in U.S. Pat. No. 7,315,667, entitled "Propagating Light to be Sensed", incorporated herein by reference in its entirety. The optical thickness of the cavity could be modified by changing between two thicknesses, for example, by etching the layer in which the cavity is formed after it is deposited or by using a half-tone mask during growth of the cavity. Alternatively, the cavity could have optical thickness that varies in the x-direction due to differences in refractive index, which could be produced in a wide variety of ways; implantation or ion diffusion (as in ion exchange) could be performed as is done in fabricating waveguides for integrated optics; another approach would be implantation-induced intermixing of multiple quantum well (MQW) structures as in laser diode fabrication; further, ultraviolet light-induced changes in refractive index could be used as with germanium-doped glass used in fabricating fiber Bragg gratings (FBG) in glass fibers; in principle, any technique that can modify refractive index by implantation, heat, light, or other operation could be used.

Also, a wedge-shaped layer of transparent material or of a Fabry-Perot filter could have filter assemblies formed at its upper surface such as by techniques described above. In other words, in addition to having filters of the types described above, there could also be a continuously varying thickness across a filter component so that, in addition to the time-varying effects of each filter assembly, additional spectral information is contained in the encoded emanating light, and can be obtained by appropriate processing. With techniques such as this, it may be possible to measure the entire spectrum with a loss of not more than 50% (assuming full modulation) of the light, which would be advantageous in comparison with conventional linear variable filter approaches.

In implementations as in FIGS. 9-11, laminar flow can be used to provide substantially uniform object speed past a filter arrangement. In contrast, techniques could instead be used in which laminar flow can produce non-uniform displacement or can be modified in other ways. Techniques like those described below for excitation arrangements could be used, for example.

Figure 17:
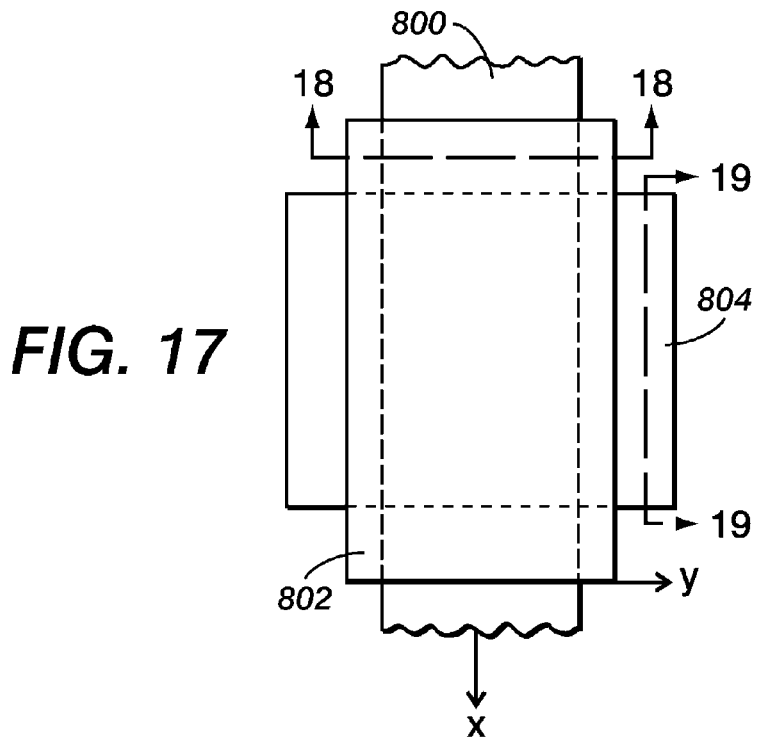
FIG. 17 is a top view of an implementation of a fluidic channel with an encoding/sensing arrangement that can be included in an implementation with features as in FIG. 1.
Figure 18:
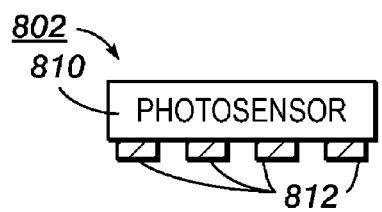
FIG. 18 is a cross-sectional view of a component in FIG. 17, taken along the line 18-18.
Figure 19:
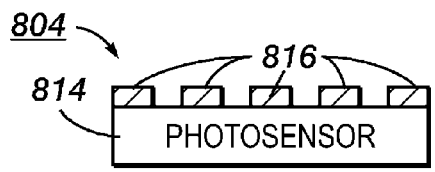
FIG. 19 is a cross-sectional view of another component in FIG. 17, taken along the line 19-19.

FIGS. 17-19 illustrate implementations of filter arrangements in which filter assemblies are on opposite sides of channel 800. In the illustrated implementation, detector 802, shown on the near side of channel 800, includes one filter assembly, while detector 804, on the far side of channel 800, includes another filter assembly. Although each detector could be implemented in a wide variety of different ways, to obtain information about emanating light and objects from which light emanates, FIGS. 18 and 19 illustrate an example in which detectors 802 and 804 each include periodic filter assemblies, one with periodicity in the x-direction, and the other with periodicity in a different direction transverse to channel 802, labeled the y-direction in FIG. 17 and illustratively perpendicular to the x-direction, though other angles between the x- and y-directions might also be useful including, in some cases, implementations in which they are parallel. In the illustrated case, sensing results from detector 802 include signals modulated in the y-direction, while sensing results from detector 804 indicate signals modulated in the x-direction. The two modulations can be used to obtain information about an object from which light is emanating.

As shown in FIG. 18, detector 802 can be implemented with photosensor 810 on a photosensitive surface of which are filters 812, periodic in the y-direction; each of filters 812 is illustratively a red band pass filter, but they could instead be any other color or closed filters or intermediate intensity gray scale filters, and could be implemented with absorption, reflection, or interference-based filtering techniques as described above. Similarly, FIG. 19 shows an implementation of detector 804 in which photosensor 814 has filters 816 on its photosensitive surface; filters 816 are green band pass filters arranged periodically.

A wide variety of other arrangements similar to FIGS. 17-19 would be possible, including, for example, another type of template layer on one side of channel 920 to provide a desired signal and a periodic mask layer to provide a periodic signal on the other side of channel 800; in this implementation, the periodic signal could be constantly analyzed to obtain values indicating displacement of an object currently flowing through channel 800, which could be used to determine an appropriate time scale for correlation with the template signal similar to techniques described herein. In another possible variation, emanating light from fluorescence could be photosensed on one side of channel 800 and emanating light due to scattering, for example, could be photosensed on the other side. If appropriate, time-varying signals from two photosensors on opposite sides of a channel could be compared, such as by correlation techniques as described herein.

Some of the exemplary implementations described below involve filter assemblies that combine periodic signals additively with template signals from filter sequences similar to some of those described above. The resulting time-varying signal emerges from the filter assembly with two different spatially varying patterns imposed on it. To produce such a signal, for example, a radial sequence or "stack" of filters similar to that shown in FIG. 4 could be used. Within a stack of filters, for example, one layer could be a template layer with an appropriate pattern to produce the template signal, while another layer could be a periodic layer with an appropriate pattern to produce the periodic signal; each of the template layer and periodic layer could have rectangles or other closed polygons of zero opacity surrounded by regions with opacity 0.5.

Figure 20:
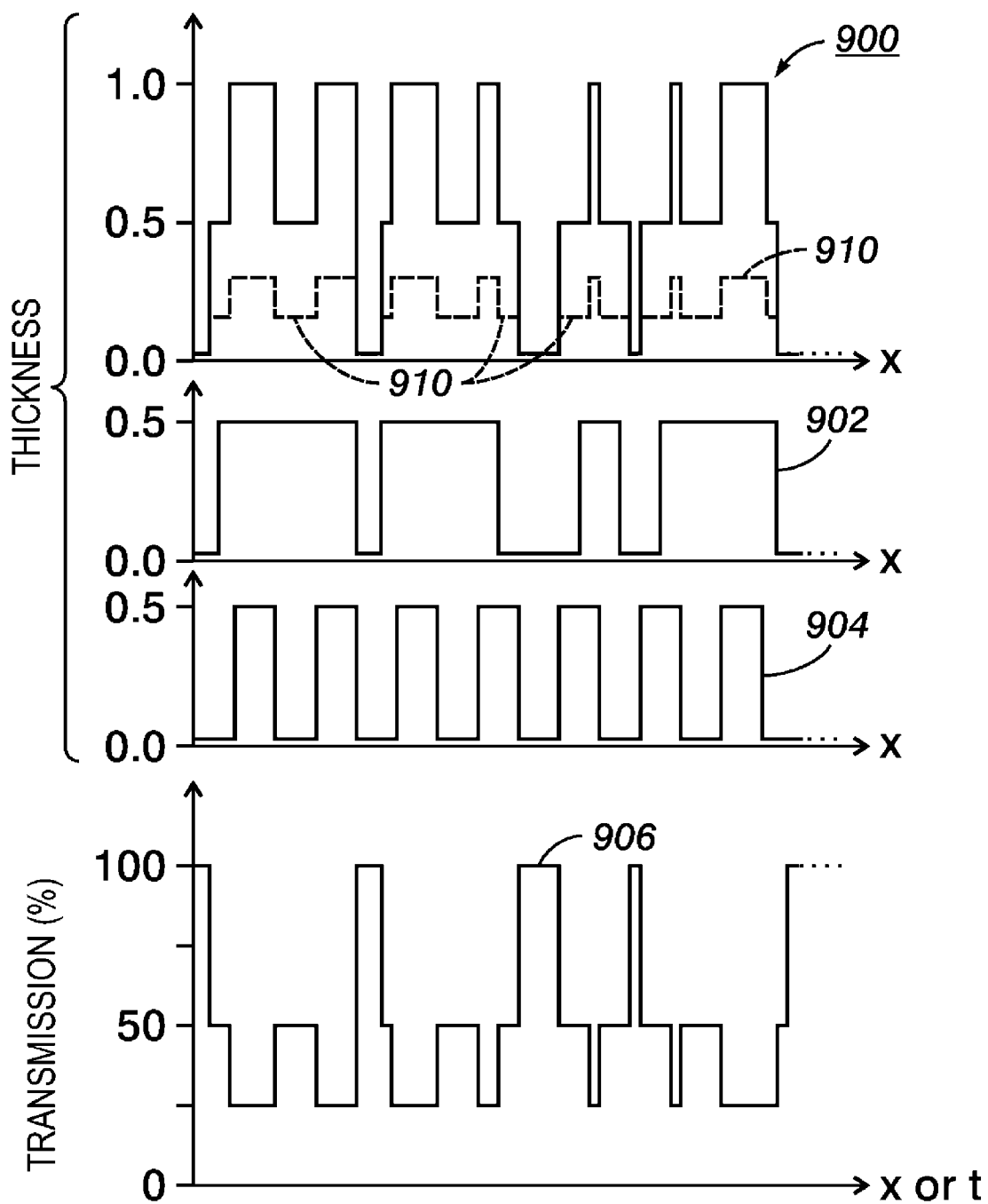
FIG. 20 includes a set of graphs showing cross-sectional thickness as a function of position in an x-direction for filters and showing transmission as a function of position in the x-direction or as a function of time t for one of the filters.
Figure 21:
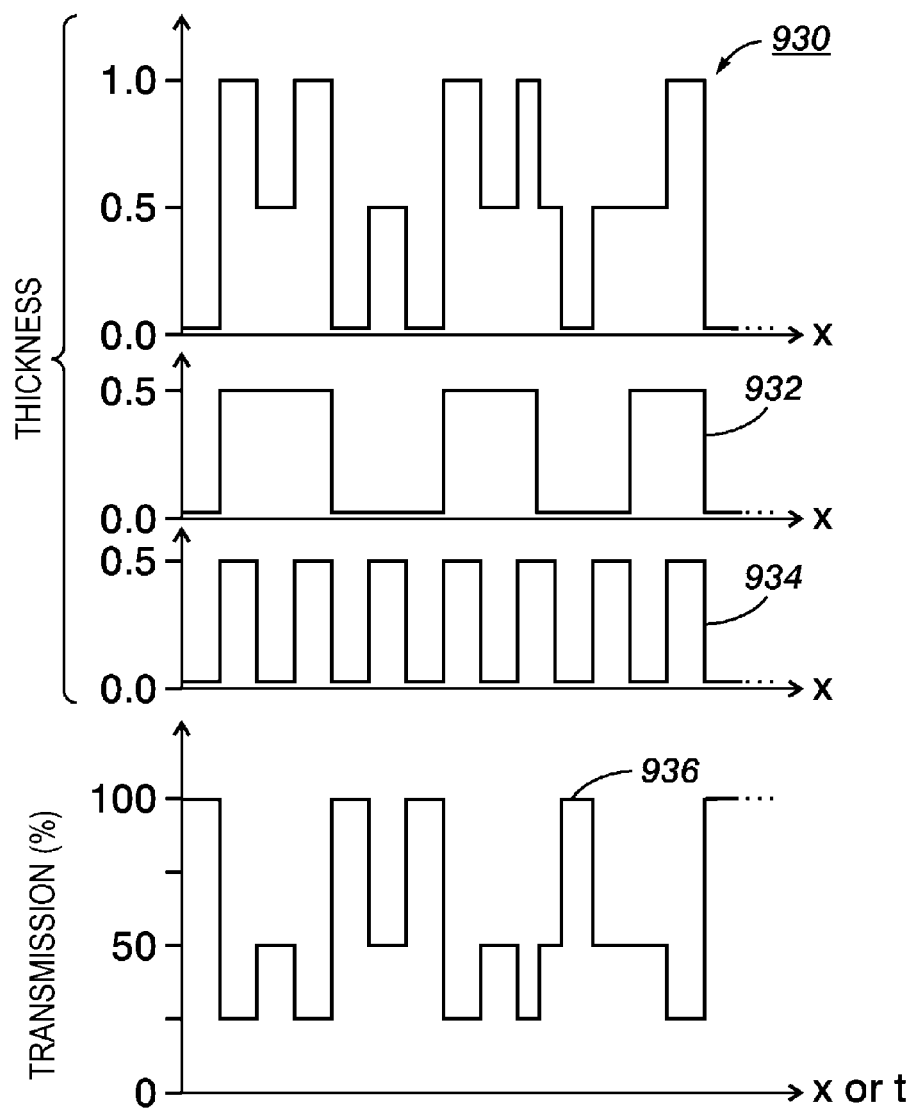
FIG. 21 includes a set of graphs showing cross-sectional thickness as a function of position in an x-direction for other filters and showing transmission as a function of position in the x-direction or as a function of time t for one of the filters.

FIGS. 20 and 21 illustrate an alternative approach that can be used with reflective gray scale filters, producing a single filter assembly equivalent to a desired radial sequence or stack of filters. To obtain filters as in FIGS. 20 and 21, thickness definitions of two filter layers can be overlaid using software tools and the thicknesses of overlapping regions can be added, resulting in regions with thicknesses of 0, 0.5, and 1 in the example given above; the two filter layers could both be oriented with variation in the same direction as in FIGS. 20 and 21, similar to the techniques of FIGS. 9 and 13, or could be oriented with variation in different directions, e.g. orthogonal to each other. For implementations in which layer thickness does not appropriately define or determine the desired equivalent filter's structure or its optical variation, the techniques in FIGS. 20 and 21 could be modified to first overlay optical feature definitions of the filters in which regions have defined optical feature values that determine the desired variation, thus obtaining an optical feature definition of the desired equivalent filter; the optical feature definition could then be converted to a layout-type description of the equivalent filter in which each region has a defined optical thickness or other characteristic that can be produced to provide the region's value for the optical feature.

If the equivalent filter definition is a thickness definition to produce a purely transmissive/reflective filter with no color variation, and if partial etching can be performed, an equivalent filter that approximates the equivalent filter definition can be constructed by first depositing a highly reflective material, such as chromium, over the entire filter assembly, and by then partially etching the reflective material away in regions with thickness 0 or 0.5 to an appropriate extent, leaving a thin, partially transmitting layer, after which the remaining reflective material can be etched away in regions with thickness of 0. Sharpness of edges in the resulting etch pattern is proportional to contrast in transmitted and reflected light patterns. The actual effect of a pattern on light emanating from an object can be calibrated based on sensing results obtained with a calibrated object such as a known particle.

Where partial etching is unreliable, other techniques may be used, such as by techniques that deposit a first patterned layer of thickness 0.5 with any suitable patterning technique, then depositing over it a second patterned layer of thickness 0.5 that is patterned without etching, such as with liftoff or other patterning techniques that do not require etching. Furthermore, similar techniques might be applied to produce layered filter structures that include DBRs of varying transmission/reflectivity and/or cavities of varying optical thickness, such as those described above in relation to FIGS. 16-18; variation in cavity thickness could result from any appropriate combination of thickness variation and refractive index variation, produced with any appropriate techniques.

Filter 900 in FIG. 20 is equivalent to the combination of a random filter and a periodic filter, superimposed one on the other. Curve 902 shows the shape of the random filter, while curve 904 shows the shape of the periodic filter; as can be seen, the random and periodic filters both have only two thickness levels, either 0 or 0.5, but filter assembly 900 has three thickness levels, corresponding to 0, 0.5, and 1. Curve 906 shows a resulting transmission function. Emanating light passing through filter assembly 900 includes both displacement and position information about an object from which it emanates, and allows time-scaling techniques to extract that information, as described below.

The technique illustrated in FIG. 20 can be adjusted as suggested by dashed lines 910 within filter 900. In other words, total light output can be changed by scaling the amplitude of the thickness levels: rather than 0, 0.5, and 1, for example, thickness levels of 0, 0.2, and 0.4 could be used, allowing greater light transmission. It may be necessary, however, to make a tradeoff between greater light output, and therefore total signal intensity, on the one hand, and greater light modulation on the other-greater light modulation may facilitate calculation of displacement and position within a given observation region. The mask suggested by dashed lines 910 emphasizes total light output because it has reduced thickness and, conversely, increased transmission, with a thickness of 0 being equivalent to transmission of 1 and vice versa. The scaling suggested by dashed lines 910 may require great precision: the x-direction scale of features in assembly 900 may be as great as 10 μm, while a useful thickness may be as thin as 10 nm of chromium.

Similarly, filter assembly 930 in FIG. 21 is equivalent to the combination of a chirp filter represented by curve 932 and a periodic filter represented by curve 934. A combination of chirp and periodic filters can make it possible to more efficiently extract displacement and position information about objects that may have different speeds. Curve 936 shows a resulting transmission function, which allows information extraction.

A stack-equivalent filter assembly as in FIGS. 20 and 21 can in some cases have a smaller MFS than either of the simpler non-uniform filters. As mentioned above, loss of resolution can occur for light emanating from objects approximately as large as the MFS.

Figure 22:
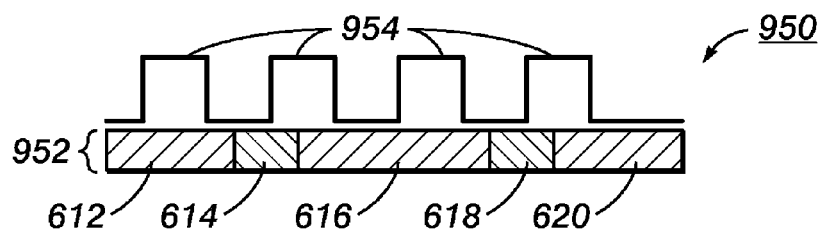
FIG. 22 is a schematic cross-sectional view of a filter assembly that includes two simpler filters.

FIG. 22 illustrates one way in which a longitudinal sequence of filters, such as a random band pass filter arrangement as described above in relation to FIGS. 9-11 can be combined with a reflective gray scale filter arrangement, illustratively a periodic gray scale filter. Filter arrangement 950 in FIG. 22 includes filter subassembly 952 with a longitudinal sequence similar to that described above in relation to FIGS. 9-11. On the upper surface of subassembly 952 is a periodic filter subassembly with regions 954, each having an intermediate transmission level such as 0.5. As a result, filter assembly 950 combines the technique of FIG. 20 with that of FIGS. 9-11, providing distinguishable time-varying signals for emanating light of different colors, and also modulating the emanating light to allow time-scaling techniques as described below. In effect, the time-scaling operations can be performed in the same way for each emanating color's signal, and the different color signals can be used to distinguish types of objects after time scaling.

Figure 23:
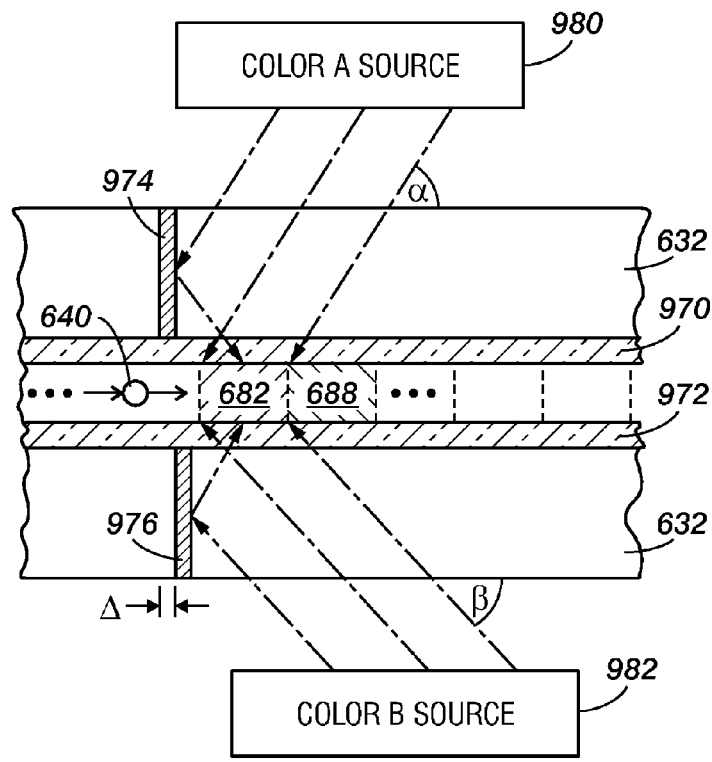
FIG. 23 is a partially schematic cross-sectional view showing an excitation arrangement that can be included in an encoding component as in FIG. 2.

FIG. 23 illustrates a cross section of a channel bounded by wall-like parts, similar to channel 504 in FIG. 8, and with reference numerals as in FIGS. 9-13 for similar items. The implementation in FIG. 23 could be included in a fluidic analyzer system as in FIG. 8 or in another appropriate system that can be used to obtain information about objects. For example, object 640 could be a biological cell, and the channel between wall-like parts 970 and 972 in FIG. 23 could receive object 640 in a fast flowing stream of fluid that surrounds object 640 and maintains laminar flow, providing ample flow at the center of the channel.

An excitation pattern with regions 682 and 688 is produced in the implementation of FIG. 23 by superimposing two interference patterns in collimated narrow band light from two offset sources, such as lasers. The light from the sources is reflected into the channel by mirrors 974 and 976, which could be air gaps, metal layers, distributed Bragg mirror structures, or any other appropriate light reflective structures. Light from source 980 illustratively has a photon energy spectrum described as color "A", and enters at angle α, while light from source 982, with a photon energy spectrum described as color "B", is reflected by mirror 976 after entering at angle β. Mirrors 974 and 976 are offset slightly in the longitudinal direction, with the offset being illustrated in FIG. 23 as the distance Δ. Because of the difference in wavelength and the slight offset, sources 980 and 982 produce a combined interference pattern including regions 682, 688, and so forth, similar to that in FIGS. 12-13. Periodicity and absolute position of each interference pattern can be independently adjusted by changing positions and tilt angles of mirrors 974 and 976.

Various other interference techniques could be used in an implementation similar to that in FIG. 23. Some examples are described in co-pending U.S. patent application Ser. No. 11/698,409, entitled "Method and System Implementing Spatially Modulated Excitation or Emission for Particle Characterization with Enhanced Sensitivity", incorporated herein by reference in its entirety. Although the technique of FIG. 23 provides a two-color excitation pattern with interdigitated colors due to interference, similar techniques could be used to produce more complex excitation patterns with additional colors, with different arrangements or sizes of regions, and so forth.

Excitation patterns could also be produced in various other ways, including, for example, structured light sources, holography, and so forth. FIGS. 24-28 illustrate several additional ways of obtaining a spatially modulated signal from an object such as a biological cell or virus by a sequence of colored excitations. In general, the illustrated objects pass through a fluidic or microfluidic channel in which they encounter a sequence of differently colored excitation regions; depending on the excitation/absorption/scattering spectrum of the object, a time-varying spatially modulated signal is produced, including features that indicate characteristics of the object. For example, if the object is excited by only one of two excitation colors, its signal will have different features than if it is excited only by the other or by both of two different excitation colors. If the excitation colors change in a periodic manner, as in FIGS. 12-13, the resulting signal will also have periodic modulation.

Figure 24:
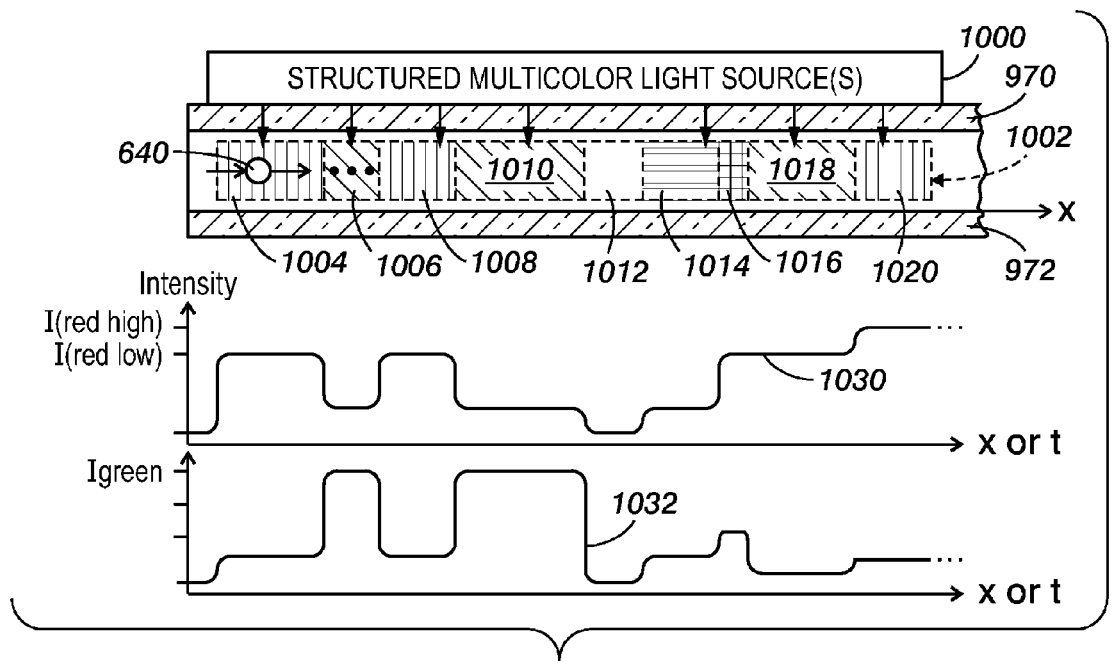
FIG. 24 is a partially schematic cross-sectional view of another excitation arrangement that can be included in an encoding component as in FIG. 2, together with graphs showing emanating intensity for exemplary objects.

FIG. 24 illustrates an example in which object 640, again in a channel between wall-like parts 970 and 972 as in FIG. 23, travels past excitation component 1000. Component 1000 includes one or more structured multicolored light sources, and produces excitation pattern 1002 in the channel. A structured light source could, for example, be active or passive, and could, for example, be implemented with photolithographically structured light emitting diodes (LEDs) or laser diodes (LDs) or even different photolithographically structured phosphors that are excited by a single laser, in which case a large variety of excitation patterns including random patterns could be implemented even with a simple uniform fluidic channel as shown. The minimum feature size (MFS) of the resulting excitation pattern, such as pattern 1002, should be of the order of the size of object 640, thereby maintaining a large modulation depth or amplitude of the time-varying signal because each excitation region is relatively short in the longitudinal direction.

Excitation pattern 1002 includes a number of types of excitation regions which, taken together, can produce a wide variety of features in a time-varying signal. Excitation regions 1004, 1006, 1008, and 1010, for example, illustrate a random two-color pattern of excitation regions, in which the lengths of the regions are not uniform and also are not periodic. After this sequence is region 1012, a gap in pattern 1002 in which excitation component 1000 provides no illumination; alternatively, component 1000 could provide broadband or white light of any appropriate intensity in region 1012—in either case, the response of objects would be similar to other implementations in which non-colored excitation occurs. While regions 1004 and 1008 are illustratively red and regions 1006 and 1010 are illustratively green, region 1014 is shown as blue, followed by region 1016 in which blue and red excitation overlap. After overlapping region 1016, region 1018 provides red excitation at approximately the same level as regions 1004 and 1008, while region 1020 then provides a higher intensity of red excitation.

Curves 1030 and 1032 illustrate possible time-varying signals emanating from object 640 as it travels along a path through excitation pattern 1002. In the illustrated example, it is assumed that object 640 has a uniform speed or that its actual speed as a function of position has been calibrated with a test pattern, so that the illustrated time-varying signal can also be treated as a position-dependent signal, as indicated by the axis, labeled x OR t. Curve 1030 illustrates the signal emanating from an object that responds strongly to red excitation, and much less strongly to blue or green excitation, while curve 1032 illustrates an example of an object that responds strongly to green excitation, but only weakly to red or blue excitation. As a result, the parts of curves 1030 and 1032 from regions 1004, 1006, 1008, and 1010 are approximately complementary, with curve 1030 being high when curve 1032 is low and vice versa. In the illustrated example, curve 1030 has an intensity value I(redlow) during regions 1004 and 1008, while curve 1032 has intensity I(green) during regions 1006 and 1010. Then, in region 1012, both curves are approximately at 0, after which each of them rises slightly during region 1014 due to blue illumination. In region 1016, curve 1030 rises slightly above I(redlow), while curve 1032 similarly rises due to overlapping excitation. Then, in region 1018, curve 1030 falls back to I(redlow) while curve 1032 returns to the low level it had during regions 1004 and 1008. Finally, during region 1020, curve 1030 rises to I(redhigh), and curve 1032 rises slightly from its level during region 1018.

In general, the time-varying signals from different types of objects will have different features that make it possible to distinguish the objects, while objects of the same type or the same object on different occasions should produce very similar time-varying signals. More particularly, the modulation depth, sometimes referred to herein as amplitude, of a signal directly indicates its emanation spectrum, as suggested by the difference between curves 1030 and 1032 across regions 1004, 1006, 1008, and 1010.

In the implementations in FIGS. 23 and 24, laminar flow can provide substantially uniform speed. In contrast, FIGS. 25-27 illustrate examples in which laminar flow can produce non-uniform displacement or other variations.

Figure 25:
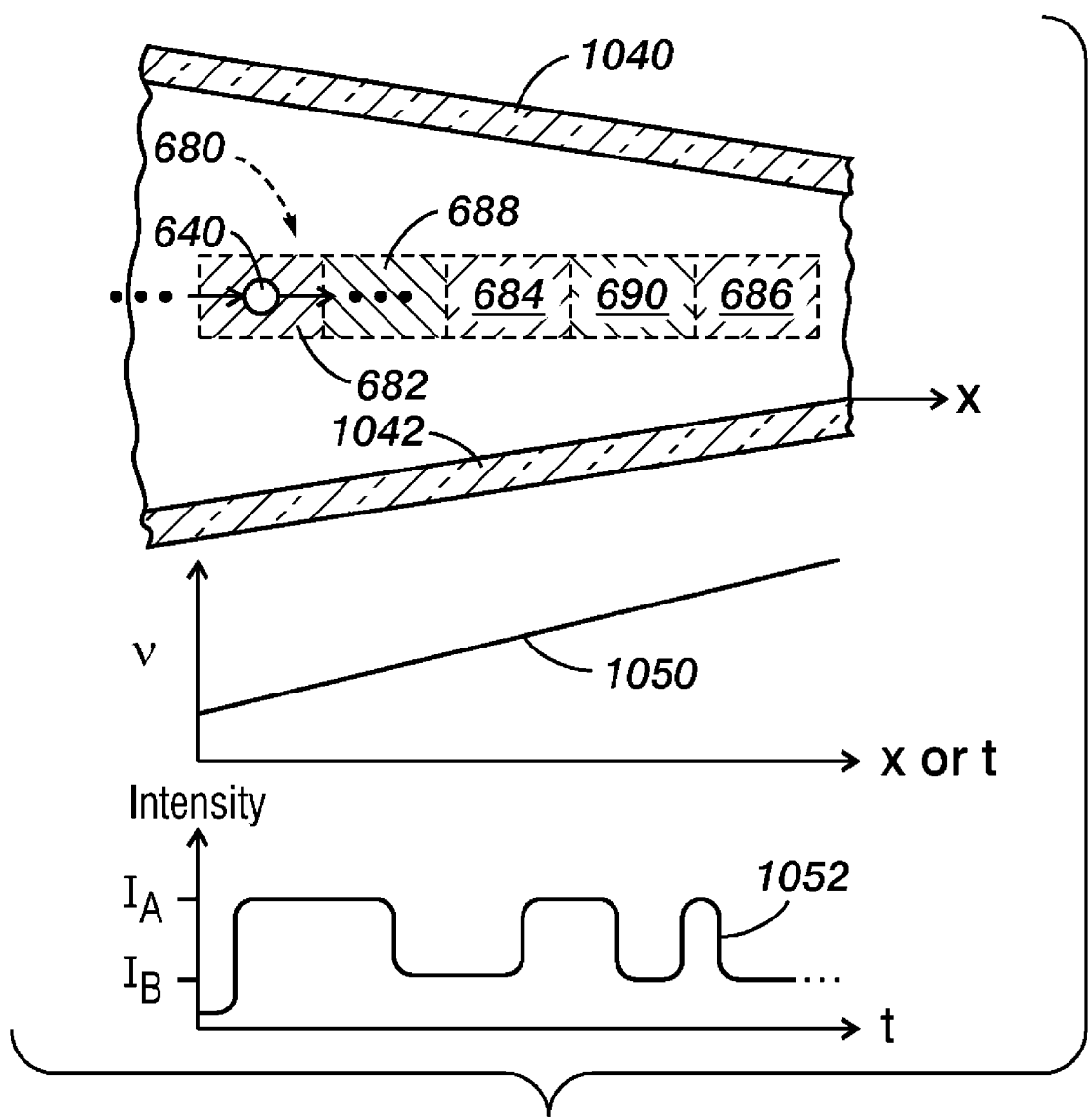
FIG. 25 is another partially schematic cross-sectional view showing a displacement control arrangement that includes shaped boundaries, together with graphs showing velocity of an object and also showing intensity of emanating light as a function of time.

FIG. 25, taken along a line similar to that of FIGS. 23 and 24, shows wall-like parts 1040 and 1042 with linearly decreasing distance between them. As a result, as object 640 passes through interdigitated two-color excitation pattern 680, its velocity increases linearly as indicated by curve 1050, either as a function of position or of time. Therefore, rather than a periodic time-varying signal as illustrated in FIG. 13, the resulting time-varying signal is chirped, meaning that the periods decrease linearly due to change in velocity of object 640 resulting from change in flow speed of fluid in the channel as channel dimensions change. Curve 1052 illustrates the resulting chirped signal, which has intensity I(A) during regions 682, 684, and 686, and intensity I(B) during regions 688 and 690. As can be seen, the duration of the signal during each successive region is shorter than the preceding region, resulting in the chirped pattern.

The technique in FIG. 25 is only one of a variety of ways of producing a chirped time-varying signal, and various other techniques could be used. For example, a non-planar mirror such as a spherical mirror could be used to produce a chirped interference pattern analogous to the excitation pattern in FIG. 23, in which case an object would pass through a chirped excitation pattern. Also, more complex flow speed distributions could be obtained by modifying the channel walls in other ways or by providing devices that change the flow speed or flow pattern within the channel, any of which would produce more complex time-varying signals from different objects. In addition, as mentioned above, multicolor interdigitated interference patterns could be used, or excitation patterns could be created with holographic techniques.

Figure 26:
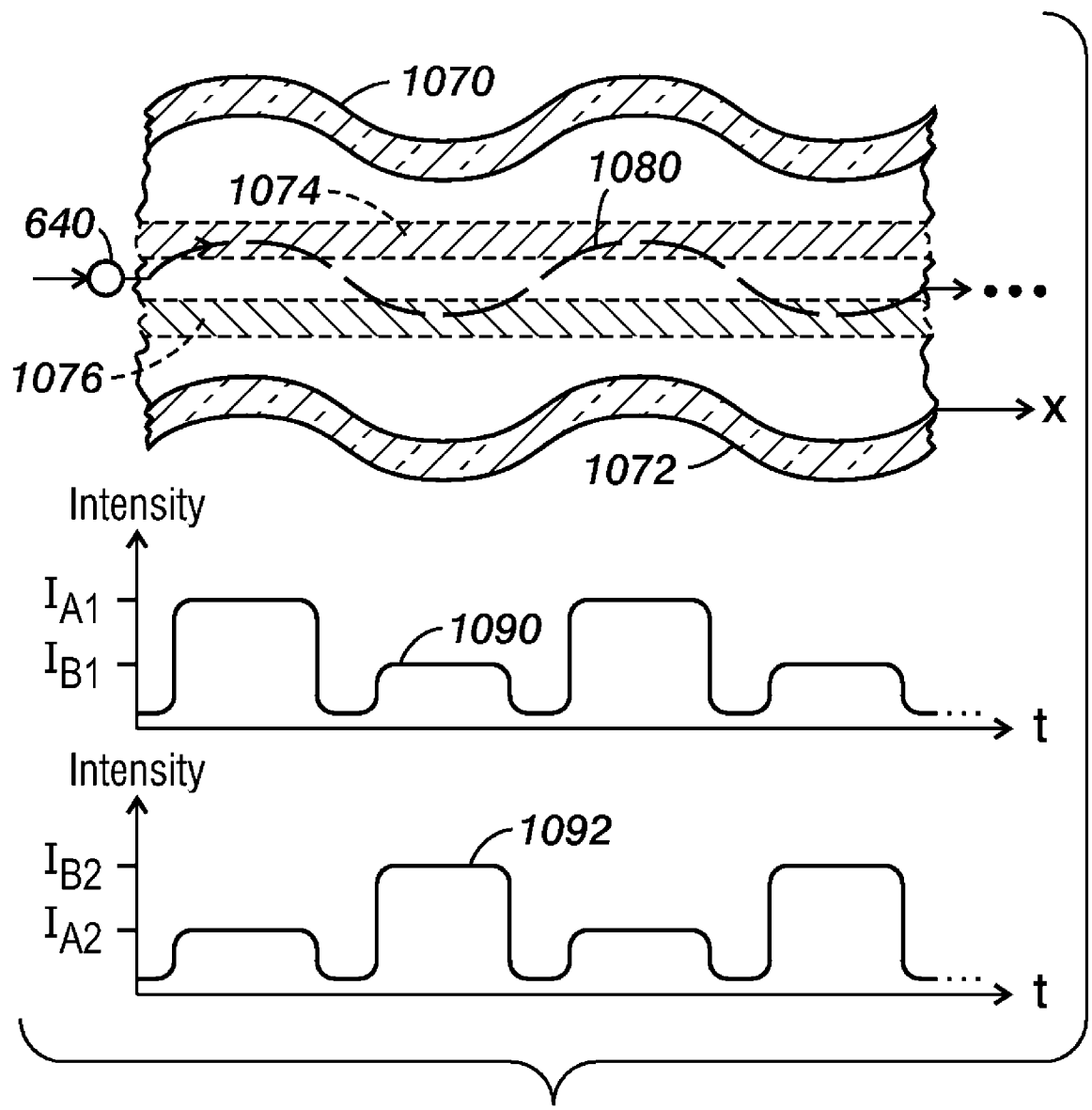
FIG. 26 is a cross-sectional view of another displacement control arrangement that can be included in an encoding component as in FIG. 2, together with graphs showing intensity of emanating light for exemplary types of objects.
Figure 27:
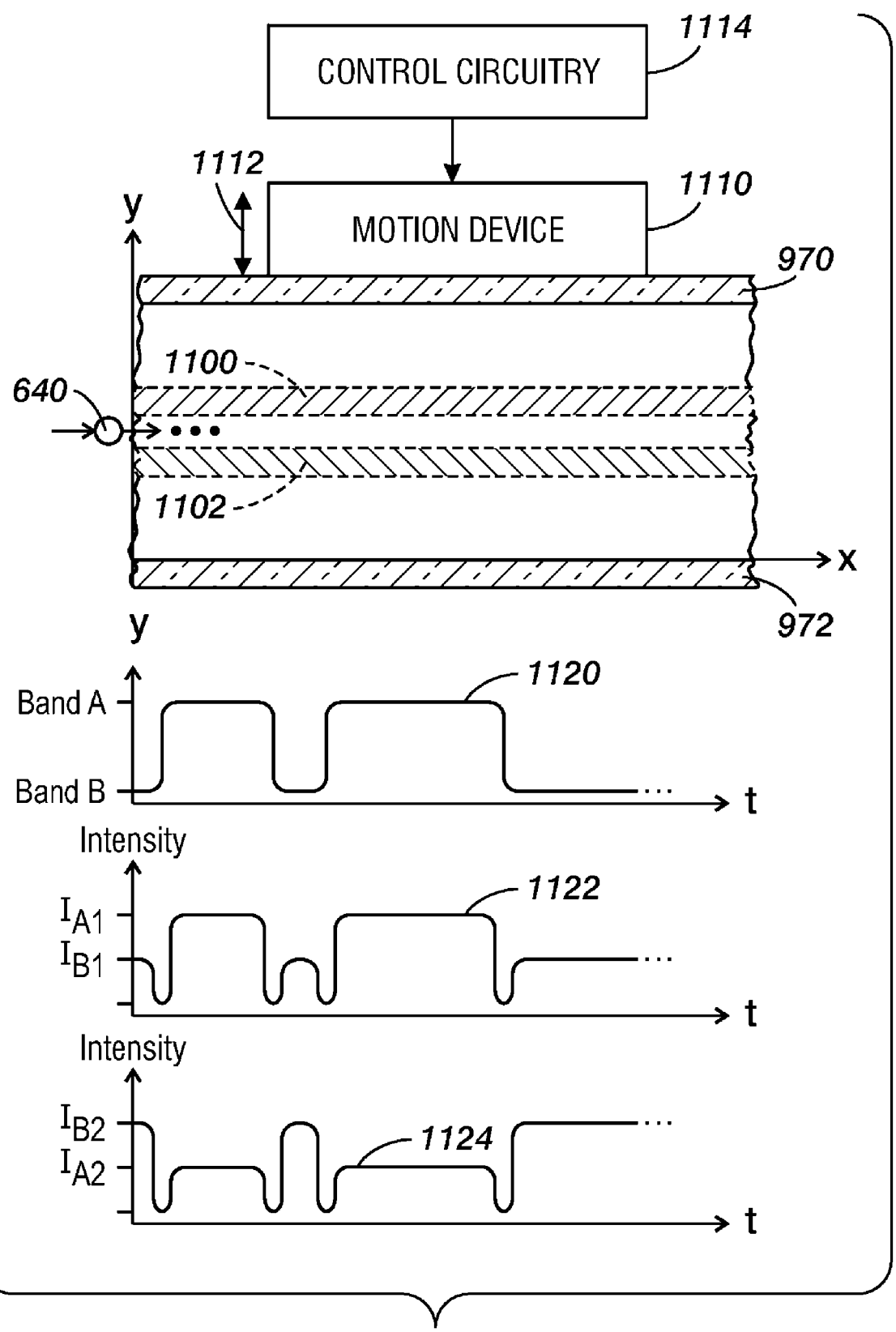
FIG. 27 is a partially schematic cross-sectional view of another displacement control arrangement that can be included in an encoding component as in FIG. 2, together with a graph showing displacement as a function of time and graphs showing intensity of emanating light as a function of time for exemplary types of objects.

FIG. 26 illustrates, on the other hand, how relatively simple time-varying signals could be produced using more complicated techniques. In general, such techniques assume that geometry of a channel directs flow of object 640 in a defined manner such as periodic, chirped, or random, through a sequence of excitation regions. If laminar flow is maintained, as described above, the excitation regions remain undisturbed by channel walls, and can therefore remain homogeneous. This allows redirection of particle flow past a simpler filter assembly geometry, and may be advantageous in cases where it is easier to redirect particle flow to produce a desired time-variation of emanating light than it would be to produce a filter assembly to produce the same time variation; for example, it might be easier to change channel wall shapes than to produce a desired filter assembly. In other cases, on the other hand, it might be advantageous to obtain more abrupt or rapid signal transitions with a well-defined filter assembly. In addition to the techniques described below, which involve shaping or moving walls, an object's flow within a channel could also be redirected by other techniques; an electrically charged object such as a particle, for example, could be redirected by electrical field variations. In general, however, the Reynolds numbers in typical microfluidic and nanofluidic implementations are so small that laminar flow conditions are, as a practical matter, always present.

In the example in FIG. 26, wall-like parts 1070 and 1072 are parallel, but each of them is shaped like a sinusoidal wave, resulting in a sinusoidal flow pattern in the channel between them. Excitation regions 1074 and 1076 are homogeneous of two different colors, illustratively labeled "A" and "B". As object 640 follows sinusoidal path 1080, it moves back and forth between regions 1074 and 1076, passing through a small gap between them twice during each period. Curves 1090 and 1092 illustrate exemplary time-varying signals that could result from an object traveling along path 1080. Curve 1090 illustrates an example of an object of a type that responds strongly to color A but only weakly to color B, while curve 1092 illustrates an example of an object of a type that responds strongly to color B and weakly to color A. As a result, the curves are somewhat complementary, although each curve goes to approximately 0 while path 1080 is crossing the gap between regions 1074 and 1076.

Wall-like parts 970 and 972 in FIG. 27 are substantially straight and parallel, as, for example, in FIG. 23. Between them are homogeneous excitation regions 1100 and 1102, similar to regions 1074 and 1076 in FIG. 26. Motion device 1110, which could be an electrically controlled device such as a solenoid or motor-driven piston, produces relative movement between the path of object 640 and stripe-like regions 1100 and 1102, as indicated by bi-directional arrow 1112. Control circuitry 1114 provides signals to control operation of motion device 1110; the resulting motion need not be periodic, but could take any appropriate pattern, resulting in arbitrary time-varying signals with features indicating different types of objects. An alternative would be to move the light sources or other components that control positions of regions 1110 and 1112; more generally, any combination of relative movements between walls 970 and 972 on the one hand and regions 1100 and 1102 on the other could produce movement as indicated by bi-directional arrow 1112. Furthermore, additional variations could be produced by changing fluid flow within the channel so that the speed or other displacement of object 640 changes as a function of time relative to the other movements. Motion device 1110 could be set up to produce variations in response to trigger signals indicating incoming objects.

Curve 1120 illustrates movement of object 640 in the y-direction between region 1100, labeled "Band A", and region 1102, labeled "Band B". As illustrated, object 640 spends different lengths of time in each region and can spend a random amount of time in each region, resulting in a random excitation pattern. Curves 1122 and 1124 illustrate exemplary time-varying signals that could be produced by the technique of FIG. 27. One type of object responds more strongly to color A in region 1100, as illustrated by curve 1122, while the other responds more strongly to the color B in region 1102, as illustrated by curve 1124. As each object travels between regions 1100 and 1102, it passes through the gap between them, resulting in a brief interruption of the emanating light, so that each curve goes briefly to 0. In curve 1122, the intensity in region 1100 is I(A1), while the intensity in region 1102 is I(B1), a lower value. Conversely, curve 1124 illustrates that the intensity is higher in region 1102, at intensity I(B2), and lower in region 1100, at intensity I(A2). The two curves are, in general, complementary, except for times when they are passing through the gap between regions 1100 and 1102; object 640 can be moved instantaneously between Band A and Band B, moving very quickly across the gap between regions 1100 and 1102, so that the time in which it is passing through the gap are very brief.

Figure 28:
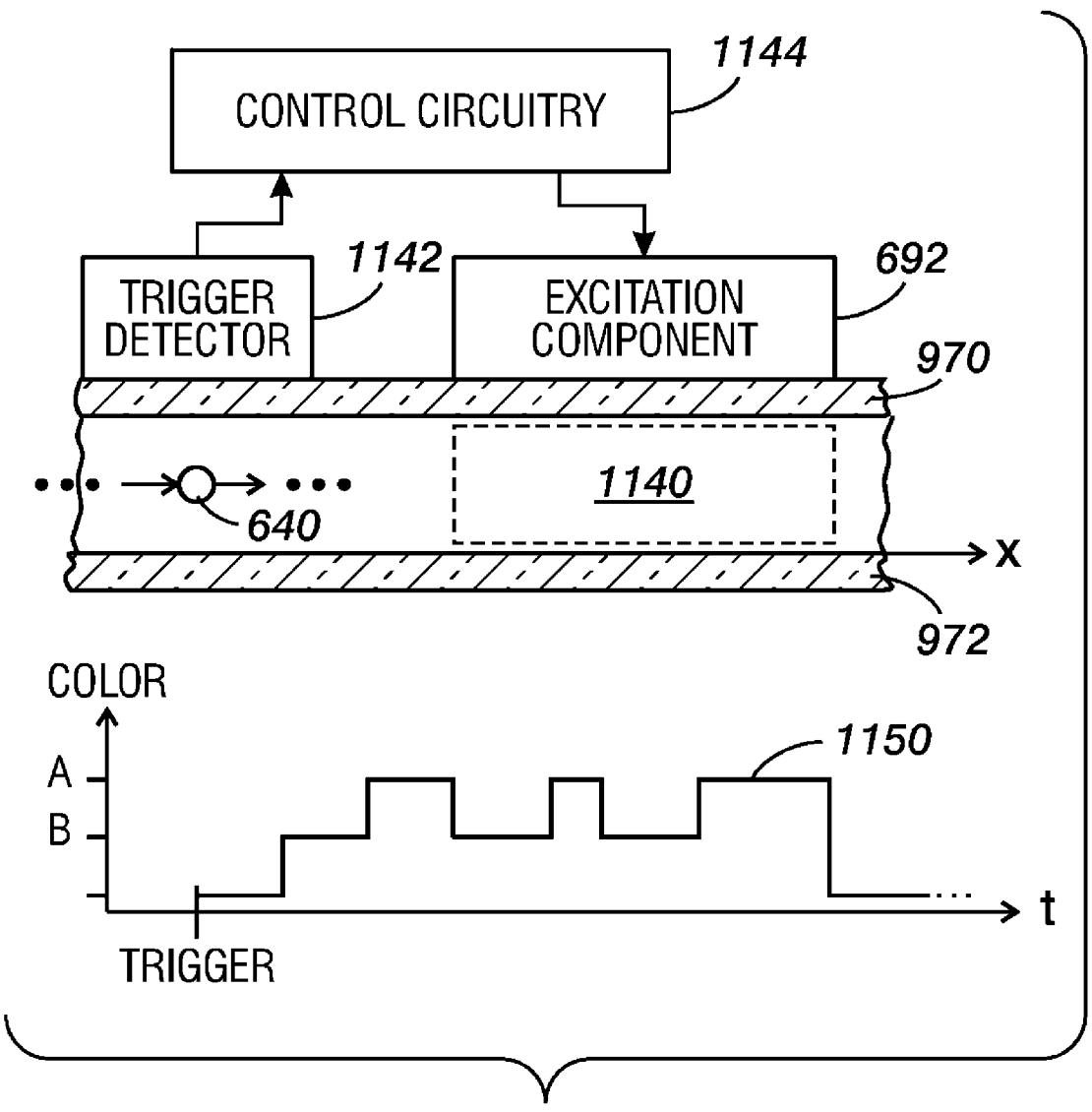
FIG. 28 is a partially schematic cross-sectional view of another excitation arrangement that can be included in the encoding component as in FIG. 2, together with a graph showing color of excitation as a function of time.

FIG. 28 illustrates a technique in which time-varying signals resulting from different excitation colors can be produced with a single excitation region in which color varies over time. As object 640 travels by laminar flow through the channel between wall-like parts 970 and 972, excitation component 692 is able to produce a sequence of different colors in excitation region 1140. As object 640 passes trigger detector 1142, detector 1142 provides a trigger signal to control circuitry 1144, which can then provide appropriate control signals to excitation component 692. Trigger detector 1142 could be implemented, for example, as described in co-pending U.S. patent application Ser. No. 11/315,992, entitled "Sensing Photons From Objects in Channels", incorporated herein by reference in its entirety.

Curve 1150 in FIG. 28 illustrates one example of how the color of excitation in region 1140 could vary over time, analogous to techniques for varying illumination in a recreational setting such as a dance hall. As shown, excitation of colors A and B alternates, and is provided for random durations, although it could be provided in a periodic or chirp pattern rather than in a random pattern as shown. In general, accuracy of the technique of FIG. 28 depends on obtaining accurate trigger signals, such as from a Coulter counter or from a backward- or forward-scattered signal, so that time variations are correlated to object positions to produce excitation equivalent to a particular excitation pattern; accuracy also depends on the presence of only one object in region 1140 at any given time. The trigger signal from detector 1142 can provide additional information about object 640, such as particle size, and this information can be used by control circuitry 1144 to select a specific excitation sequence or to scale or otherwise modify a given excitation sequence, such as to optimize information encoded in emanating light; for example, control circuitry 1144 could scale the excitation pattern to have a minimum feature size comparable to the dimension of object 640.

Figure 29:
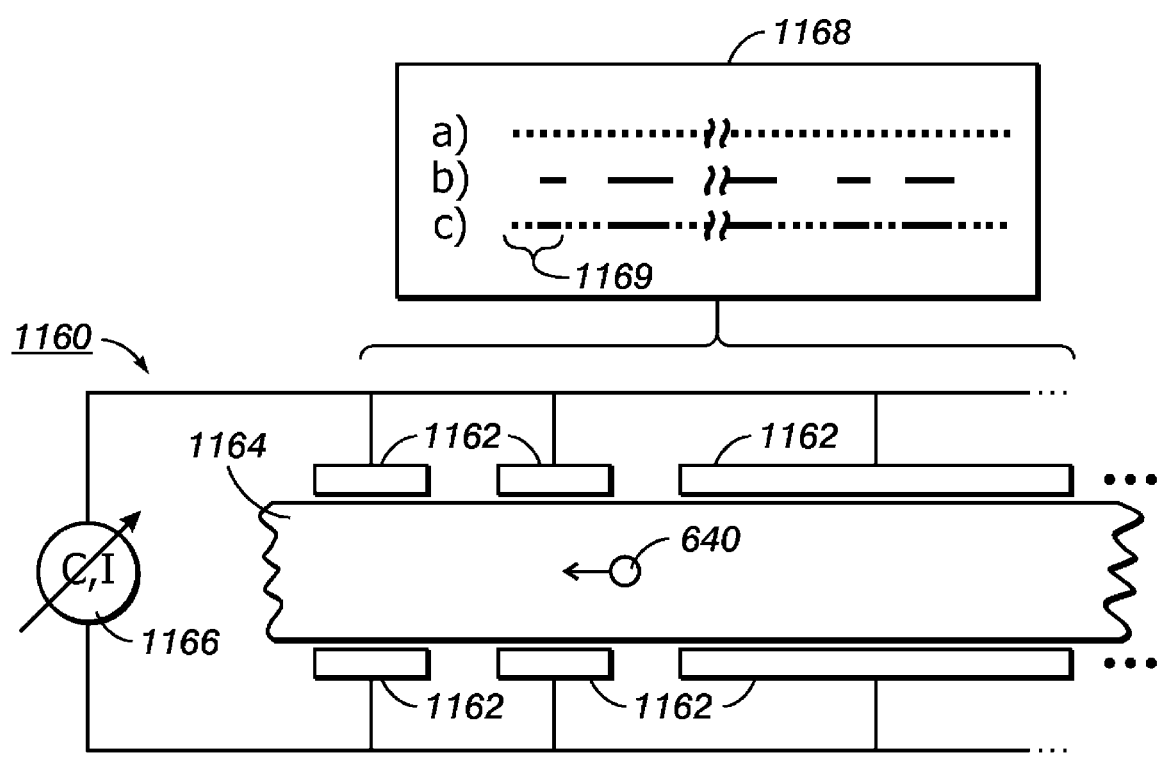
FIG. 29 is a partially schematic cross-sectional view of an encoding/sensing arrangement that includes features as in FIG. 1 with an impedance-based sensor.

FIG. 29 shows an example of a non-optical technique that can be used to obtain sensed time-varying signals in which information about an object is encoded. The technique illustrated in FIG. 29 is similar to a technique described in co-pending U.S. patent application Ser. No. 11/698,409, entitled "Method and System Implementing Spatially Modulated Excitation or Emission for Particle Characterization with Enhanced Sensitivity", incorporated herein by reference in its entirety. Impedance spectroscopy flow cytometry is further described in Cheung, K., Gawad, S., and Renaud, P., "Impedance Spectroscopy Flow Cytometry: On-Chip Label-Free Cell Differentiation", Cytometry Part A, Vol. 65A, 2005, pp. 124-132, also incorporated herein by reference.

Encoding/sensing component 1160 in FIG. 29 includes an array of electrodes 1162 along walls of channel 1164, within which object 640 can travel, such as by being carried by a fluid. Electrodes 1162 are connected to measurement device 1166, which could be implemented as described in the Cheung, et al. article cited above. As suggested, device 1166 could record a time dependent signal such as a measure of capacitance or current, or any other impedance-related electrical characteristic that can vary between electrodes on opposite sides of channel 1164. As object 640 travels through channel 1164 between electrodes 1162 on either side, in other words, device 1166 obtains a sensed time-varying wave form indicating a characteristic of object 640. Although capacitance and conductance are illustratively shown, a wide variety of different electrical characteristics could be measured, providing information about a variety of characteristics such as, for a biological cell, cell size, membrane capacity, cytoplasm conductivity, cytoplasm permittivity, and so forth. Furthermore, device 1166 can provide an electrical wobble frequency to electrodes 1162 to determine frequency at which a given characteristic is measured by encoding the time-varying wave form.

Electrodes 1162 form a pattern that can be understood from the binary signals in box 1168. The upper signal, labeled "a)", is a simple periodic binary signal; the middle signal, labeled "b)", is a random binary signal, with varying ON and OFF durations; and the lower signal, labeled "c)" can be obtained by logically combining signals like a) and b) in an alignment similar to that shown—in the illustrated example, the logical combination is an OR operation, so that a given point of signal c) is ON (black) when one or both of the aligned points of a) and b) is ON, but is OFF (white) whenever neither of the aligned points of a) and b) is ON. The positions and lengths of electrodes 1162 are proportional to the lengths of ON segments of the binary signal c), and therefore concurrently encode the sensed time-varying wave form both periodically according to signal a) and randomly according to signal b); the proportionality of ON segments of c) with electrodes 1162 can be seen by comparing lengths of the first three ON segments of signal c), reference number 1169, with lengths of the three upper electrodes 1162. As a result of the concurrent encoding described above, techniques as described in greater detail below can be used to extract information about object 640 from the sensed time-varying wave form, such as about position, speed, and other characteristics.

The arrangement of electrodes 1162 in FIG. 29 is merely illustrative, and could be varied in many ways. For example, electrodes 1162 could form a similar pattern along only one side of channel 1164 with no electrodes on the other side or with a single, large unpatterned electrode on the other side. Similarly, rather than only being opposite each other, electrodes could be positioned around a channel. Furthermore, different materials could be used for different electrodes and electrodes could be spaced at different distances from the walls of channel 1164 in order to obtain more complicated patterns and therefore encode additional information. Also, simpler binary signals as in box 1168 could be combined in any appropriate logical combination other than the OR combination, as appropriate in a given application.

The general technique illustrated in FIG. 29 could also be applied in other contexts. For example, rather than electrodes 1162, a pattern as illustrated in box 1168 could be obtained with an array of photosensitive cells of different lengths along channel 1164. Also, of course, a filter arrangement could be implemented with a similar pattern in an optical implementation, providing a simpler alternative to some of the filter arrangements described above.

Figure 30:
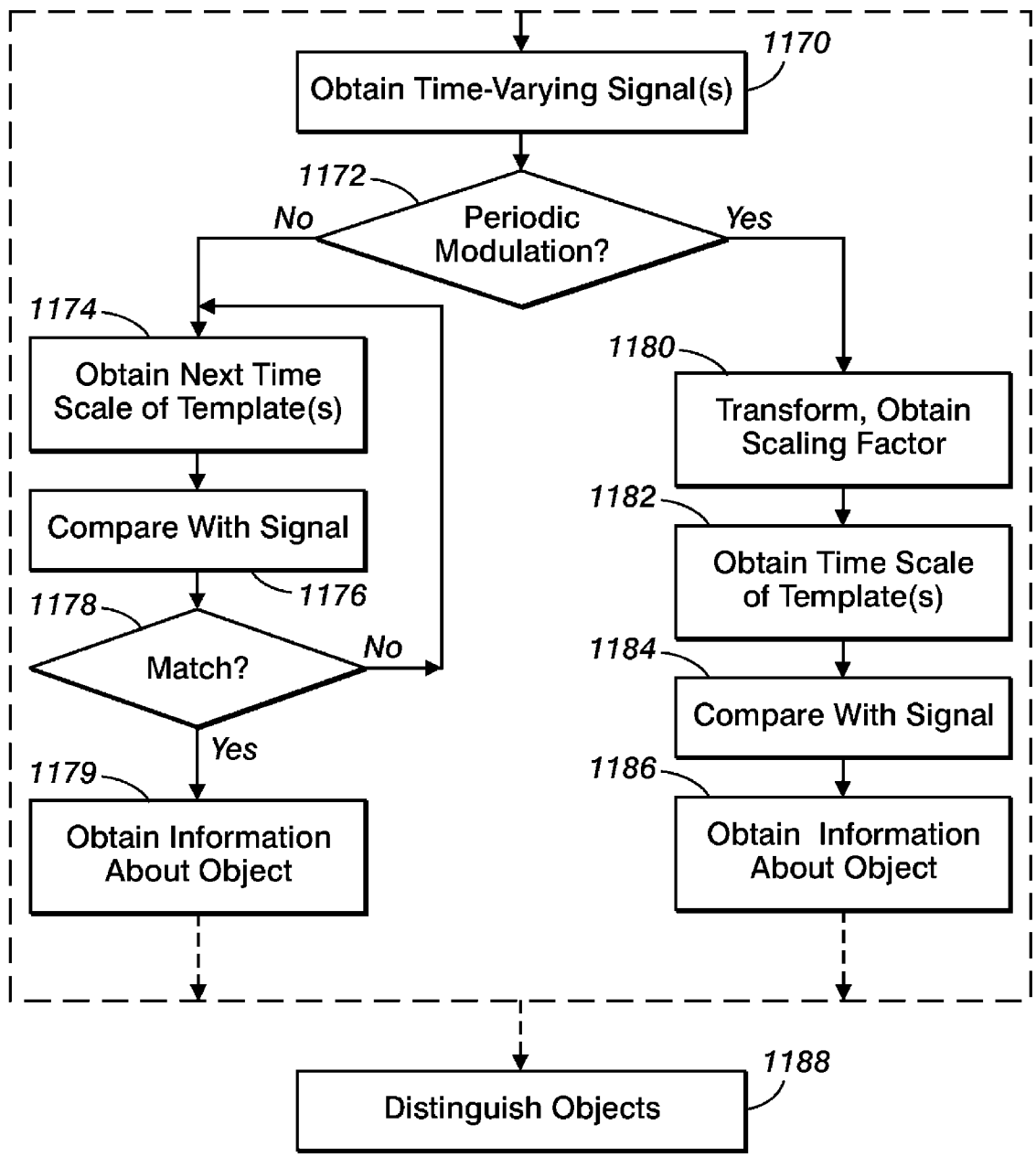
FIG. 30 is a flow chart showing operations in techniques that include time-scaling of time-varying wave forms and comparison of such wave forms.

The flow chart in FIG. 30 illustrates ways in which data indicating information about objects, such as information about speed or other displacement rate, position, and type, can be obtained by CPU 402 (FIG. 6). FIG. 30 also suggests ways in which routines 440, 442, and 444 (FIGS. 6 and 7) could be implemented.

The operation in box 1170 obtains one or more time-varying signals from one or more photosensors as one or more objects travel along respective paths past the photosensors. The objects can, for example, travel through a channel as described above in relation to FIGS. 8-13 and the time-varying signals can be obtained in many different ways. In general, however, at least one of the time-varying signals results from emanating light being encoded with one of the various types of non-periodic filters or non-periodic excitation arrangements described above. Emanating light could concurrently be encoded with a periodic modulation by passing a periodic excitation arrangement or filter arrangement, such as, for example, a stack of filters that includes a non-periodic filter and a periodic filter; an equivalent filter as in FIG. 20 or FIG. 21; a random multi-color filter with a periodic filter on it as in FIG. 22; a pair of filters with respective photosensors on opposite sides of a channel as in FIG. 17 but with one periodic and one non-periodic; a periodic excitation arrangement and a non-periodic filter arrangement or vice versa; and so forth. The operation in box 1170 could also obtain time-varying signals resulting from other types of excitation, such as from thermal or acoustic excitation or excitation by an electric or magnetic field, or even time-varying signals of other types, such as from electrical sensing similar to that in FIG. 29, such as based on resistance, capacitance, inductance, or other electrical impedance or other effects of objects due to characteristics such as charge, polarization, internal structure, spin, magnetic effects, and so forth.

The operation in box 1172 branches on whether the time-varying signals from box 1170 include periodic modulation, either within a signal that is also non-periodically encoded or in a separately sensed signal that is sensed concurrently with a non-periodically encoded signal, as would be the case in an implementation like that in FIG. 17. As explained in greater detail below, the use of periodic modulation can significantly increase efficiency, compared with a brute-force technique that considers many different time scales of a template and is therefore much more computationally intensive and time consuming. Since it may not be practical to implement a system that performs both a brute-force technique and also uses periodic modulation, the operation in box 1172 might have been performed at the time of manufacture or programming of a system, or it might be determined by an operator who switches between two modes of operation of the system, with each mode performing one of the approaches rather than the other.

Several different cases could be identified, including the following three: First, implementations in which there is no periodic modulation, so that only the brute-force technique is possible; second, implementations in which a first sensor provides a non-periodically modulated signal and a separate second sensor concurrently provides a periodically modulated signal, so that one or both techniques could be used, and the periodic modulation technique can be used without extracting both motion-dependent and motion-independent information from a single time-varying signal; and third, implementations in which a single sensor provides a time-varying signal that includes both periodic and non-periodic modulation, so that one or both techniques could be used, but the periodic modulation technique requires extraction of both motion-dependent and motion-independent information from a single time-varying signal.

If both approaches could be implemented in a single machine, it might be possible to implement a coarse-fine technique for the second and third cases identified above, in which the periodic modulation approach is used first and, if its comparison results do not meet an appropriate precision criterion, the brute-force approach is then used across a range of expected time scales to find an adequately precise result. An example might be where two particles concurrently and with almost the same speed (rate of displacement) pass a photosensor with different phase such that their periodic modulations partially cancel each other out.

If no periodic modulation is available or if appropriate for other reasons, the operations in boxes 1174, 1176, 1178, and 1179 can implement the brute-force approach or a similar approach. The brute-force approach performs a series of iterations, making an exhaustive sweep of all expected time scales of template signals; each iteration has a respective time scale and attempts to correlate time-scaled versions of one or more template signals with a time-varying signal from box 1170. The brute-force approach can be based on a range of time scales estimated by analyzing conditions that might have caused time scaling; also, a suitable increment between time scales can be determined based on factors such as signal sampling rate and rate of signal modulation. To reduce the computational intensity of the brute-force approach, statistical distributions of time scale shifts of a signal can be measured in advance, and only the most probable shifts can then be applied before comparing it with template signals; this approach is advantageous if the measurement requires less effort than the saved computation time, but it is problematic if time scale can change while signals are being obtained. In any case, these approaches are more computationally expensive when implemented for real-time signal analysis.

Each template signal is related to the non-periodic filter arrangement used to encode emanating light. More specifically, each template signal is a signal that produces a sharp peak in a correlation result with a time-varying signal encoded by a specific non-periodic filter assembly in response to light emanating from a type of object; template signals may also be adjusted due to blurring or smearing that can occur with objects smaller than a pattern's MFS in order to facilitate comparison with sensed time-varying signals. Because, however, the time scale of signals from box 1170 depends on an emanating object's speed or another displacement rate, correlation with the template would not produce such a peak if the template had been obtained at a different speed or displacement rate.

In order to match the time scale of the template to the time scale of the signal from box 1170, the operation in box 1174 obtains, in each iteration, a respective scaled version of the template. The operation in box 1174 could, for example, begin with an unscaled version of the template, and then attempt scaled versions for higher and lower speeds in subsequent iterations, or it could begin with a high speed or a low speed version and then try successively smaller or larger speeds, respectively. If more than one type of object is being detected, the respective template signals of all the types could be scaled in the same way during each iteration of the operation in box 1174. In general, "time scaling" refers to any operation that modifies a time-varying signal of total duration T1 to produce a time-scaled version that has a different total duration T2 within which each part that corresponds to a part of the unscaled signal has approximately the same value (or an equivalent value) as the corresponding unscaled part but has a duration T(scaled) that is approximately T2/T1 times the corresponding unscaled part's duration T(unscaled). Time scaling could be performed in a wide variety of ways and, more specifically, in any way appropriate for the types of signals being compared, such as whether digital or analog and whether high, intermediate, or low resolution, and also appropriate for the direction of scaling, whether increasing or decreasing. For example, with time-varying analog signals, frequency scaling could be performed, while various time-scaling techniques can be applied to time-varying digital signals.

The operation in box 1176 then performs a comparing operation, such as a correlation operation, on the time-varying signal from box 1170 and the time-scaled version of each template from box 1174. A correlation operation in box 1176 can be implemented, for example, as described in co-pending U.S. patent application Ser. No. 11/698,338, entitled "Method and System for Evaluation of Signals Received from Spatially Modulated Excitation and Emission to Accurately Determine Particle Positions and Distances", incorporated herein by reference in its entirety. Other possible comparing operations that might be used in box 1176 include convolution-related operations, digital approximations of correlation and other such operations, digital sum-of-difference techniques such as with normalization or other intensity or magnitude scaling, and counterpart analog techniques such as integration over comparator or differential amplifier output, and so forth. The result of the comparing operation in box 1176 is then used in box 1178 to determine whether the time-varying signal matches any of the time-scaled templates.

The operation in box 1178 could be implemented with any appropriate matching criteria, such as by comparing correlation results with an appropriate threshold to determine whether the correlation results include a sharp peak, either upward or inverted, indicating a match by correlation or anti-correlation, respectively. Various other matching criteria could be used in box 1178 to evaluate comparison results, depending on the type of comparing operation performed in box 1176. If a match is not detected in box 1178, the method returns to obtain the next time-scaled versions of templates in box 1174.

When the operation in box 1178 finds a match, the operation in box 1179 obtains information about the matching object, such as data indicating its speed or other displacement rate, position, and type. For example, the time scaling at which the match was found indicates the speed of the object. Similarly, the position of the peak in correlation results indicates the object's position in the x-direction, which can be obtained using techniques described in co-pending U.S. patent application Ser. No. 11/698,338, incorporated by reference above; accurately determining an object's position in real time is especially valuable for applications in which objects are sorted in real time. As explained in greater detail below, correlation results can also provide information about the object's type, such as about its emanation spectrum.

On the other hand, if periodic modulation is present, the operation in box 1180 can perform an appropriate operation to obtain a periodicity value such as a frequency or wavelength. For example, the operation can obtain a transform, such as a fast Fourier transform (FFT) or other approximation of an FFT, to obtain a spectrum of frequencies present in the time-varying signal from box 1170. If the signal is periodically modulated at a frequency that depends on an object's speed or other rate of displacement, this spectrum will include a sharp peak at the modulation frequency, which can be detected similarly to the technique for detecting a match in box 1178. The modulation frequency (or an equivalent wavelength) can then be used to obtain an appropriate scaling factor, such as based on previous calibration of speeds with modulation frequencies and scaling factors. In addition, the modulation frequency and/or the counterpart scaling factor can be used as displacement data, because they indicate the object's speed or other displacement rate.

The mathematical basis of this technique can be outlined as follows: A generated time-varying signal S(t) contains a template signal T(t) and a periodic signal P(t), i.e. S(t)=T(t)+P(t). The resulting observed signal X(t) may, however, be a time-scaled version of the generated signal with noise N(t) added, where a Is the time-scaling factor, i.e. X(t)=T(a*t)+P(a*t)+N(t). P(t) can be designed so that F(P(t)) is essentially a delta function centered at frequency ω0, where F(P) is the Fourier transform of P. Then F(P(a*t)) is a delta function centered at frequency a*ω0. As long as the index of max(F(X(t)) is also a*ω0 (which can be assured by multiplying P by a large enough scalar), then a can be calculated from the ratio of the index of max(F(X(t)) to the known frequency ω0. This scaling factor a can then be applied to the template signal T(t) before comparing with the observed signal X(t) (or alternatively to X(t) before comparing with T(t), but this would usually be computationally impractical).

The operation in box 1182 can then use the scaling factor from box 1180 to obtain a time-scaled version of the template. This operation can be implemented similarly to box 1174. Also, the operation in box 1184, which compares the time-scaled version of the template with the time-varying signal from box 1170, can similarly be implemented like the operation in box 1176.

If box 1184 is implemented with correlation, the correlation results should include a sharp peak, and the operation in box 1186 can find the sharp peak, such as in the way described above in relation to box 1179; this would confirm that the scaling factor correctly indicates the speed or other displacement rate of the object. The position and other characteristics of the sharp peak can then be used to obtain the object's position in the x-direction and other information about the object, similarly to the operation in box 1179.

After the operation in box 1179 or the operation in box 1186 obtains information about an object, further operations can be performed for other objects, beginning again with box 1170, as suggested by the dashed lines from boxes 1179 and 1186 to box 1170. Either after obtaining such data for one object or for a collection of objects, the operation in box 1188 can be performed to distinguish objects, such as with operations as described above in relation to FIG. 7. Other useful ways to distinguish objects include counting objects of different types and obtaining ratios between counts of different types. As suggested in boxes 1174 and 1182, the time scaling and comparing operations can be performed for two or more templates, each for a respective type of object, so that the correlation results obtained with the templates also indicate an object's type, such as its emanation spectrum.

Figure 31:
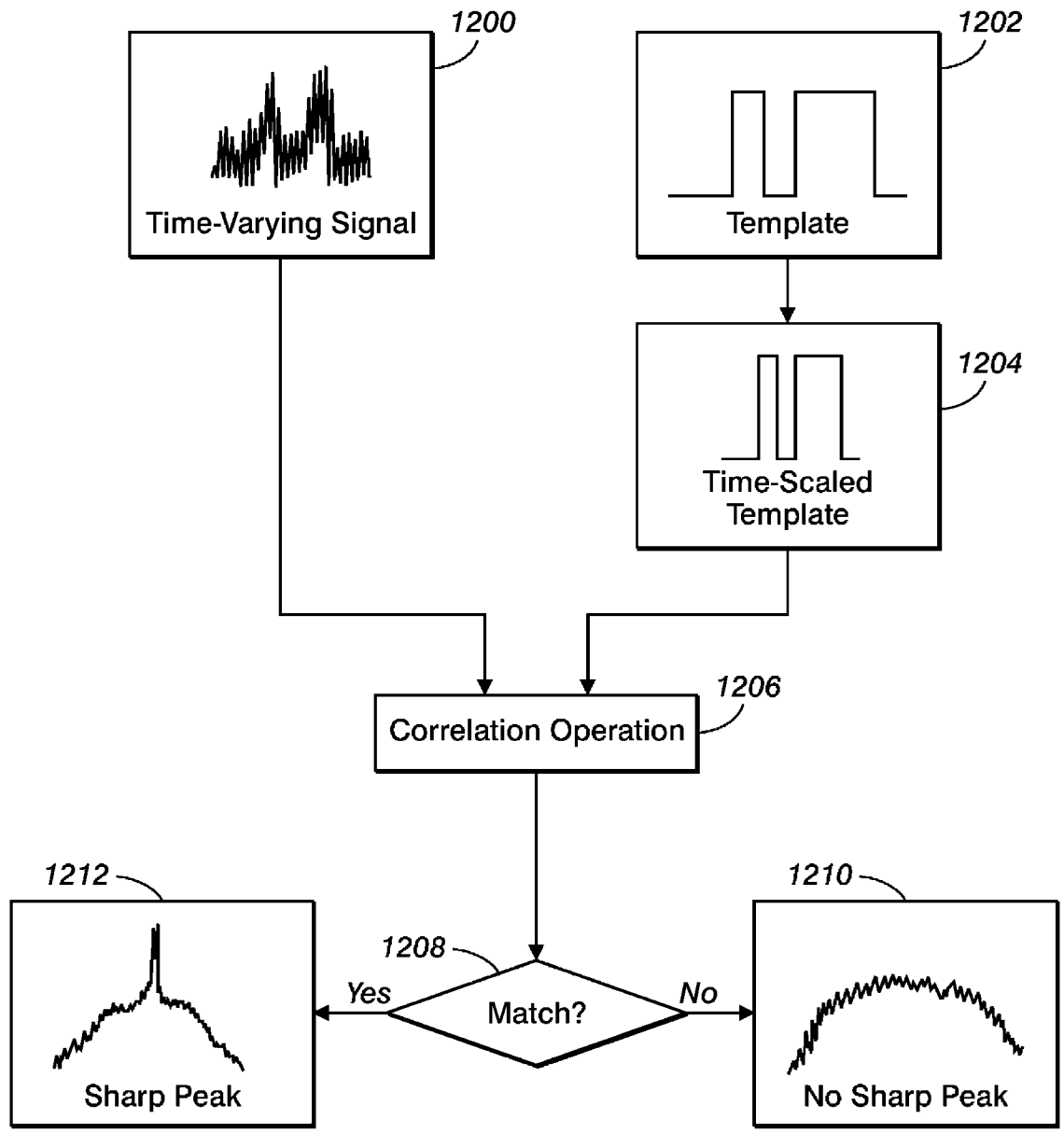
FIG. 31 is a schematic flow diagram illustrating how operations that perform time-scaling and comparison can be performed as in the technique of FIG. 30.

FIG. 31 illustrates schematically how time-scaling and correlation could be performed, such as in boxes 1174, 1176, 1178, 1182, and 1184 in FIG. 30. The signal in box 1200 is an example of a time-varying signal that could be obtained in box 1170. The illustrated signal results at least in part from a non-periodic encoding, such as from a random or chirp pattern. The signal in box 1202 is a template obtained from the same encoding that results in a sharp peak in a correlation result for a given type of object. In order to test the signal in box 1200, the signal in box 1202 is first time scaled, with an example of a reduced time-scaled template shown in box 1204.

After time-scaling, a correlation operation is performed in box 1206 on the time-varying signal in box 1200 and the time-scaled template signal in box 1204. As suggested in box 1208, the result from the correlation operation can indicate either a match, either by correlation or anti-correlation, or no match. If it indicates no match, the correlation results can be a waveform without any sharp peak, as shown in box 1210. If, on the other hand, it shows a match, the waveform from the correlation result has a sharp peak, either upward for correlation as shown in box 1212 or an inverted peak for anti-correlation (not shown), and the sharp peak can be detected with an appropriate operation, such as by taking a derivative as described below or by other techniques as described, for example, in co-pending U.S. patent application Ser. No. 11/698,338, entitled "Method and System for Evaluation of Signals Received from Spatially Modulated Excitation and Emission to Accurately Determine Particle Positions and Distances", incorporated herein by reference in its entirety. In addition to indicating that an object is of a type corresponding to the template signal in box 1202, the correlation results also indicate the object's position, because the position of the sharp peak corresponds to the object's position. Furthermore, the time scaling at which the sharp peak occurred indicates the speed or other displacement rate of the object.

The width of the peak in a correlation result, as in box 1212, is a measure of accuracy. In other words, the narrower the peak, the more precisely the position of the object can be determined. In general, the width of the peak depends on the relation between an object's size and the MFS of the encoding pattern; for objects of larger size, spatial resolution is limited to a fraction of object size. Furthermore, for implementations in which more than one object's time-varying signal is concurrently sensed, it may be impossible to distinguish the peaks of two particles if they are less than twice the MFS apart. If their speeds also differ, however, they may be distinguishable because their correlation peaks will occur at different time scales. In other words, two different time scalings of template signals could produce matches, such as in box 1178 in FIG. 30. In general, then, two objects may be distinguished if they have a spacing that is greater than a minimum distance and/or if they have a speed difference greater than a minimum speed difference; below those minimums, the objects may not be distinguishable.

Figure 32:
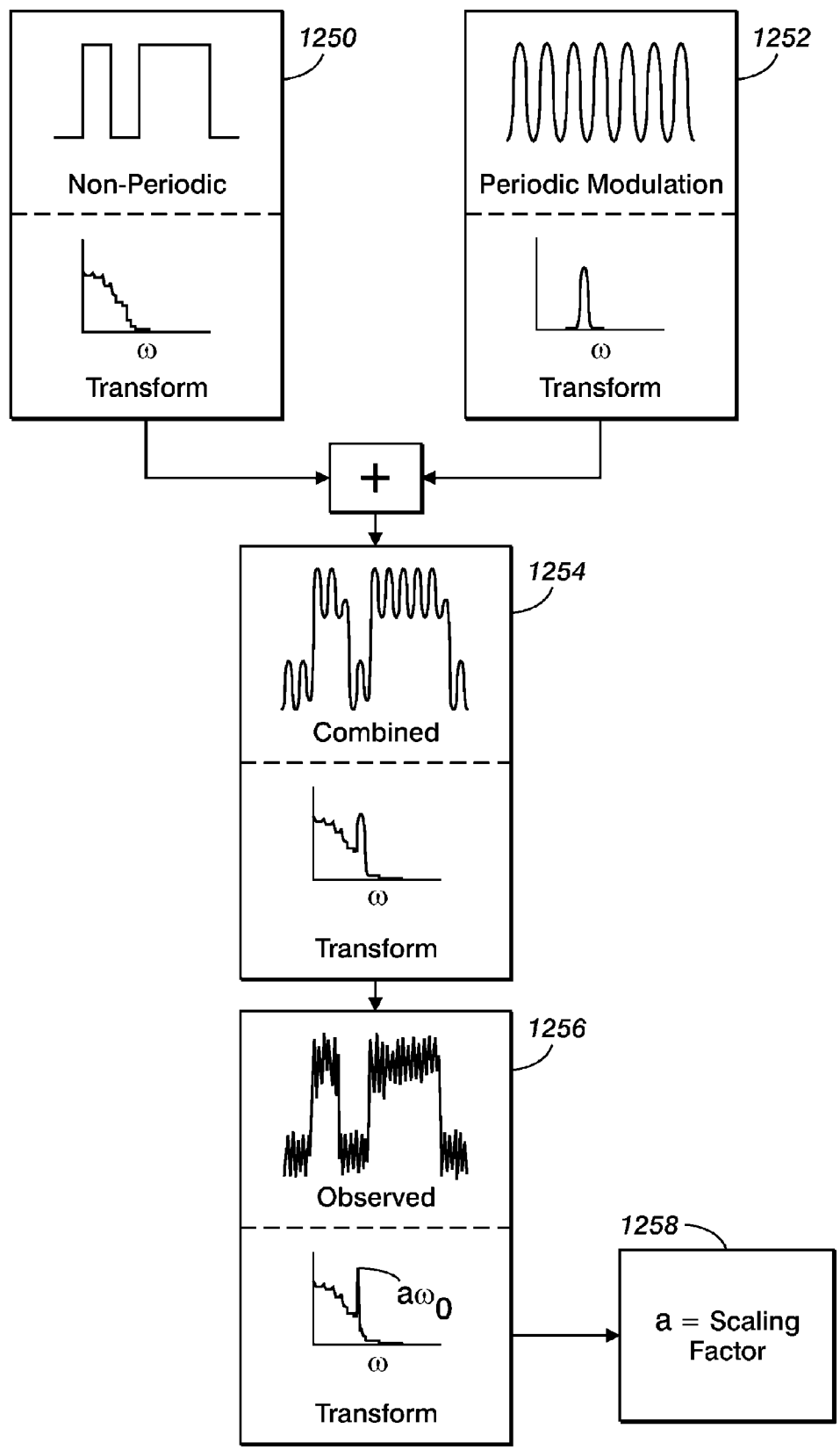
FIG. 32 is another schematic flow diagram showing how a scaling factor can be obtained as in the technique of FIG. 30.

FIG. 32 illustrates graphically how the operation in box 1180 could be implemented. Box 1250 includes a non-periodic part of a time-varying signal received in box 1170 together with its transform into a frequency domain. Box 1252, on the other hand, includes a periodically modulated part of the signal or another signal resulting from the same emanating light but periodically encoded, together with its transform into a frequency domain. As can be seen, the transform in box 1250 covers a band of frequencies and gradually tapers off near a maximum, while the transform in box 1252 has a single sharp peak at the frequency of modulation.

If the two signal parts in boxes 1250 and 1252 are combined, they result in the waveform shown in box 1254 together with its transform. As can be seen, the transform is essentially a sum of the two transforms in boxes 1250 and 1252.

Due to introduction of noise, delays, or other modifying influences, the actual wave signal received in box 1170 appears more like the observed signal in box 1256, shown with a frequency transform obtained with, for example, an FFT. Using techniques similar to those described above for detecting a sharp peak in correlation results, the sharp peak for the periodic signal can be located in the transform and used to obtain the modulating frequency. Of course, if the periodically modulated signal in box 1252 is separately received, it can be similarly transformed to obtain its modulating frequency.

When the modulating frequency is known, it can be used to obtain a scaling factor a, such as by computations as outlined above, and a also indicates the speed of the object that produced the time-varying signal, as the speed is related to the ratio of the peak frequency in the transform and a reference modulation frequency obtained at a known reference speed. Therefore, as indicated in box 1258, scaling factor a can be obtained from the transform and used to perform time-scaling, such as in box 1182.

Techniques as in FIGS. 30-32 can be modified and extended in various ways to handle a variety of situations. Such situations can, for example, involve sensing multiple objects and sensing without correlation to rapidly obtain object position.

Where a stream of objects is passing a photosensor, and the objects are sufficiently spaced, each object's time-varying signal can be isolated from those of preceding and following objects, such as by a trigger and gate mechanism. Such a mechanism records portions of the object's emanation intensity that is greater than a threshold magnitude, then applies a window function to this finite signal. Then a Fourier transform can be obtained and the result can be used to obtain a scaling factor, as above.

If two or more objects are traveling past a photosensor at the same time but at different speeds, a triggering mechanism as described above might blindly record the overlapping signal generated by the objects as if generated by one object. To avoid analyzing by correlating at only one time scale, the Fourier transform can be analyzed to find subpeaks that have high probability of resulting from periodic signals from multiple objects traveling at different speeds. Each subpeak's scaling factor can be obtained as described above, and correlation can be performed with each scaling factor to obtain correlation results for each object. Even if an error is made, by identifying a spurious subpeak, the correlation results can be analyzed to determine whether a signal emanating from an object moving at the counterpart speed was sensed.

The technique of FIG. 32 can also be used in contexts in which correlation is not necessary, but it is desired to correct for arbitrary time-scaling of chirp or other non-periodic signals, such as with a Fourier transform rather than correlation. For example, the non-periodic waveform in box 1250 could be a chirp waveform or another type of scaled periodic waveform rather than a random waveform. Correction of time-scaling of such signals can be useful because it may be desired to use an excitation or emission pattern of that type to spatially modulate light emanating from a fluorescent particle or other object as it travels along a path.

One way to implement this Fourier correction technique would be with a stack-equivalent reflective filter assembly like that described above in relation to FIG. 21 or a stacked filter as in FIG. 22 but with a periodic filter on a chirp filter. A sliding Fourier transform would be performed on a time-varying signal encoded with such a filter assembly, and the resulting transform would be analyzed to find peaks: A fixed frequency peak $\omega 0$ would correspond to the signal generated from the periodic modulation in the filter assembly, indicating particle speed; a moving frequency peak $\omega(t)$ would indicate, by its position within its frequency range, the portion of the signal from the chirp modulation that is currently being received.

The peaks from the transform could then be used to find the object's position and, more generally, to determine, within a limit resulting from Fourier transform window size, what part of the signal, e.g. start, middle, or end, is being observed at the current time. With currently available computational techniques, it is practical to make such determinations in real time, transforming a finite signal that includes both chirp and periodic modulation and is arbitrarily scaled in time before observation. Although the two frequencies $\omega 0$ and $\omega(t)$ might differ from expected values due to the arbitrary time-scaling, they will differ by the same multiplicative factor, so that the ratio $\omega(T)/\omega 0$ provides "phase information", i.e. information about an object's relative position within a non-periodic modulation such as a random or a chirp pattern, at time T and $\omega 0$ provides speed information; the phase information could, for example, indicate position of an object within a channel or the percentage of a chirp signal being sensed. In contrast, if the filter assembly provided only chirp modulation, it would be impossible to determine phase information such as the part of the signal being observed, i.e. start, middle, or end, in the presence of arbitrary time-scaling because all known frequencies would have been scaled arbitrarily.

Figure 33:
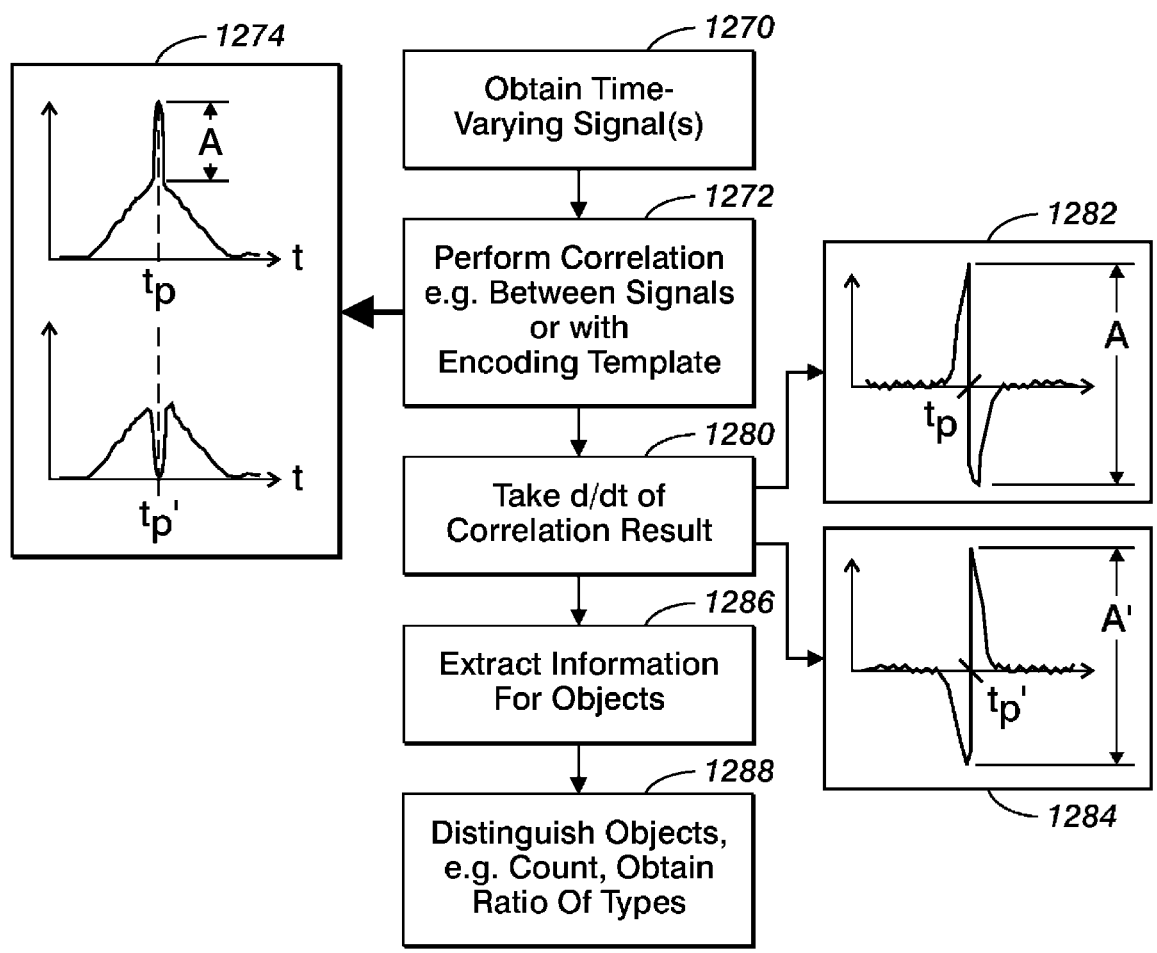
FIG. 33 is a flow chart with graphs illustrating an implementation in which information about objects is obtained from sensed time-varying signals.

The flow chart in FIG. 33 illustrates ways in which information about objects can be obtained and used by CPU 402 (FIG. 6); the technique of FIG. 33 illustratively extracts information such as a type, a position, or a spectral difference, and uses such information to distinguish objects. FIG. 33 also suggests ways in which routines 440, 442, and 444 (FIGS. 6 and 7) could be implemented. Although suitable for CPU 402, operations in FIG. 33 could be implemented with a wide variety of different types of circuitry with or without a CPU. Furthermore, although described in terms of time-varying signals from photosensors, the technique of FIG. 33 could be applied to any time-varying sensed signals, including, for example, capacitively sensed signals from charged particles with encoded information due to shapes, sizes, and positions of electrodes as in FIG. 29.

The operation in box 1270 obtains one or more encoded time-varying signals from a photosensor arrangement as one or more objects travel along respective paths past a filter arrangement and/or an excitation arrangement. The technique could be implemented with a single photosensor along the paths, but it might also be possible to implement with two photosensors on opposite sides of the paths or with other photosensor arrangements. The objects can, for example, travel through a channel as described above in relation to FIGS. 8-13 and 23-28 and the time-varying signals can be encoded in any of a wide variety of ways using filter arrangements and/or excitation arrangements, including one or more of those described above, with or without displacement control. For example, if one of the filter arrangements or excitation arrangements is at least partially non-periodic or if displacement control or excitation control is at least partially non-periodic, a respective template of the resulting non-periodic pattern for each of a number of types of objects can be used to perform a correlation operation; in other implementations, two differently encoded time-varying signals can be obtained in box 1270 and correlated with each other. Note, however, that two types could be distinguished based on a single template, especially if their time-varying signals are sufficiently complementary that one results in correlation and the other in anti-correlation with the template.

The operation in box 1270 can include providing any appropriate control signals to other components of the system, including signals to read out sensing results of photosensors. The control signals could be implemented as in routines 440 and 442 (FIG. 6), with CPU 402 providing signals through device I/O 420 to one or more of devices 422 through 424. For example, fluid flow speed could be adjusted, channel wall movement could be controlled, and, in response to trigger signals, excitation components could be controlled as described above in relation to FIG. 28. In order to obtain the time-varying signals, CPU 402 could provide signals through IC I/O 410 to obtain photosensed quantities from ICs 412 through 414.

The operation in box 1272 performs a correlation or other comparing operation on one or more time-varying signals from box 1270, such as comparing two encoded signals with each other or comparing one encoded signal with a respective template of a non-periodic encoding pattern for each distinguishable type of object. The correlation operation can produce correlation results for each pair of waveforms that is compared. For example, if box 1272 compares an encoded time-varying signal from box 1270 with each of N templates for N types of objects, N correlation results are produced.

The graphed curves in box 1274 illustrate two types of correlation results: The upper curve illustrates a correlation result where two time-varying waveforms are correlated, i.e. highly similar at the time alignment designated $t_p$; the lower curve illustrates a correlation result where two time-varying waveforms are anti-correlated, i.e. highly dissimilar at the time alignment designated $t_p'$. In each case there is a peak, with the peak in the correlated case marked to show its amplitude A and with the anti-correlated case having an inverted peak of similar amplitude. If correlation is performed on a continuous basis, correlation results could similarly be continuously obtained for each template with which comparison is made, with each object's travel past the filter arrangement producing a peak, an inverted peak, or a feature in between the two for each template.

The operation in box 1280 obtains a time-varying waveform that equals or approximates the time derivative d/dt of each correlation result from box 1272. For the correlated case, a derivative waveform like the graphed curve in box 1282 is obtained, with a positive peak followed by a negative peak, with a zero crossing at $t_p$, and with the contrast or differential quantity between the peaks again being the amplitude A. For the anti-correlated case, a derivative waveform like the graphed curve in box 1284 is obtained, with a negative peak followed by a positive peak, with a zero crossing at $t_p'$, and with the contrast or differential quantity between the peaks being amplitude A', the amplitude of the inverted peak in the lower graph in box 1274. The amplitudes obtained in this manner are, in general, free of offsets, allowing direct comparison.

The operation in box 1286 uses derivative waveforms from box 1280 to extract information for objects passing the photosensor. The extracted information could, for example, be a type based on whether an object resulted in correlation, anti-correlation, or neither with a given template; position based on the time at which a zero crossing occurs in correlation or anti-correlation; and spectral difference, e.g. a difference of emission, absorption, or scattering spectrum, based on the amplitude or contrast between positive and negative peaks from correlation and anti-correlation, respectively. Features of a derivative waveform could be found and measured using various techniques. The operation in box 1288 can then be performed to distinguish objects using information extracted in box 1286, such as by obtaining counts of different types of objects or ratios between such counts, or with other operations as described above in relation to FIG. 7.

The operations in boxes 1272, 1280, and 1286 could be implemented, for example, as parts of one or both of routines 442 and 444 (FIG. 6). The operation in box 1288 could be implemented as part of routine 444. In general, these operations could be implemented to handle signals from each object separately or to handle a signal received concurrently or in series from a number of objects, in which case minimum differences, such as in positions or speeds, may be necessary to allow separation of signals from different objects. Any appropriate combination of serial and parallel operations could be implemented in any appropriate circuitry. Data streams or other data structures defining waveforms such as templates could be stored and retrieved as needed by routines 442 and 444, such as in memory 408 (FIG. 6). Similarly, intermediate and final results of operations in boxes 1272, 1280, 1286, and 1288 could similarly be stored and retrieved as needed.

Comparison techniques other than correlation could be employed, but correlation techniques can be advantageous because they are typically not sensitive to noise, such as an AC power frequency. For example, preliminary smoothing or other preprocessing of waveforms is typically unnecessary for correlation, and available techniques for computing correlations can produce useful results even with S/N ratios significantly less than 1.0. It is, however, necessary to satisfy minimum sampling requirements if waveforms are digitized for correlation; in accordance with the Nyquist frequency, each waveform should be sampled at least twice during the time duration of its minimum feature size.

Some techniques as described above have been successfully applied to simulated time-varying waveforms. In particular, time scaling techniques have been found to improve S/N ratio of a simulated observed signal that contains both an encoding based on a template and also additive noise, and where the observed signal has an unknown time scaling that occurs before it is observed; S/N ratio of 0.5 has been obtained and 0.1 appears achievable. These results could be obtained with particle speeds up to 0.5 m/sec and higher speeds up to a few m/sec appear to be feasible, with particles having effective sizes down to 0.6 μm, and with particle separations down to a given implementation's MFS. A demonstration included counting CD4 in a whole blood sample; single tag detection was shown to be feasible.

Where a simulated observed signal includes or is accompanied by a simulated concurrent periodically modulated signal, time scaling of a template waveform based on a scaling factor from the periodically modulated signal has successfully produced matching correlation results, indicating correlation or anti-correlation as appropriate and making spectral information available, in effect allowing concurrent detection of multiple colors with a single detector such as a large-area photosensor. Particle position can be precisely determined from fine structure of correlation results. As noted above, simulation results show that spatial resolution of less than 1.0 µm is possible, and single fluorescence markers can be detected, making detection possible with smaller amounts of consumables such as markers. The techniques appear appropriate for native fluorescence, allowing agent-less detection.

Implementations as described above in relation to FIGS. 1-33 could be advantageously applied in a wide variety of sensing applications, possibly including, for example, fluorescence- or impedance-based flow cytometry or other biodetector applications that seek a signature of a particle of unknown velocity; such biodetectors often use microfluidic channels with inhomogeneous flow profiles, causing variation in particle velocity. The techniques can be used to count or obtain ratios between fluorescing objects of different types, such as different types of tagged cells, particles, tagged DNA, and so forth. In such an application, calibration can be performed using known objects, e.g. tagged beads, with known velocities to obtain template waveforms that include deviations caused by fabrication tolerances but can then be compared with sensed waveforms to obtain information about unknown objects. To improve S/N, known and sensed waveforms can be correlated, such as after time scaling of each known waveform. If a sensed waveform includes or is accompanied by periodic modulation, a periodicity value such as a frequency can be used to obtain a scaling factor for time scaling before correlation, allowing more rapid correlation than if a brute force technique is used to find a satisfactory time scaling.

Implementations described above may be advantageous in biodetector applications that require compact, low-cost components without critical optics and with high sensing efficiency. Such applications might include point-of-care flow cytometry (such as with an integrated flow cytometer), DNA analysis, proteomics, and so forth.

Also, implementations described above could be applied in scanning of bio-chips or documents where objects have different emanation spectra, and so forth. The techniques may also be applicable in various low S/N ratio systems in which a known signal is bounced off an object traveling at an unknown velocity, such as where object velocity is on the order of signal propagation velocity, as in SONAR. The techniques may be especially advantageous where precise information about position, speed, or type of objects is sought.

Exemplary implementations described above employ photosensors or impedance-based sensors with specific features, but a wide variety of sensors could be used to obtain sensing results indicating values of various parameters other than emanating light intensity, parameters that can have time variation that indicates information about objects. Similarly, implementations described above involve sensing information about objects that are moving in fluidic channels or that are moving relative to a sensor such as in scanning, but various other types of fluidic implementations or other implementations in which objects move in various other ways could be sensed to obtain sensing results suitable for techniques described above.

Components of exemplary implementations as described above could have various shapes, dimensions, or other numerical or qualitative characteristics other than those illustrated and described above. Similarly, although the exemplary implementations generally involve sensing from a single fluidic channel, implementations could readily include multiple parallel channels, allowing parallel sensing and readout and larger scale sensing.

Some of the above exemplary implementations involve specific types of fluidic components, filter components, light source components, displacement control components, sensors, and so forth, but the invention could be implemented with a wide variety of other types of components. For example, some implementations use specific types of spatial modulation based on one or more of an excitation pattern, a filter assembly, and/or displacement control, but various other types of spatial modulation could be used, including any appropriate combination of color, gray scale, and black and white patterning and including other patterning techniques such as patterned sensing; for example, in a fluidic implementation, a patterned photosensor could be printed or otherwise produced on an inward wall or other boundary of a channel or in another appropriate location. Also, some exemplary implementations use specific types of processing, such as digital signals obtained after converting sensed analog values. In general, however, the invention could be implemented with any suitable signal processing techniques, including any appropriate combination of analog and digital processing; either or both of two compared waveforms could be obtained in analog or digital form, and any combination of time scaling could be performed before comparison. Further, some exemplary implementations use large area photosensors, but various ICs with photosensing arrays might be used.

Some of the above exemplary implementations involve specific types of emanating light, e.g. fluorescence, and specific types of excitation and filtering suitable to fluorescent light, but these are merely exemplary. The invention could be implemented in relation to various other types of optical signals in various other ranges of photon energies or with any other appropriate sensed stimuli.

Some of the above exemplary implementations involve specific materials, such as in fluidic structures with light-transmissive components or in filtering arrangements with reflective material or light blocking material such as amorphous silicon, but the invention could be implemented with a wide variety of materials and with layered structures with various combinations of sublayers. Thicknesses of layers may vary across any suitable range.

The exemplary implementation in FIG. 6 employs a CPU, which could be a microprocessor or any other appropriate component. Furthermore, as noted above, operations could be performed digitally or with analog signals, and could be done either on the same IC as a photosensor array, on other components, or on a combination of the two, with any appropriate combination of software or hardware.

The above exemplary implementations generally involve use of encoding/sensing arrangements, sensors, photosensors, excitation arrangements, filter arrangements, displacement control arrangements, and so forth following particular operations, but different operations could be performed, the order of the operations could be modified, and additional operations could be added within the scope of the invention. For example, readout of sensed quantities from a sensor to obtain a sensed time-varying waveform could be performed serially or in parallel, and, with an array, could be performed cell-by-cell or in a streaming operation.

While the invention has been described in conjunction with specific exemplary implementations, it is evident to those skilled in the art that many alternatives, modifications, and variations will be apparent in light of the foregoing description. Accordingly, the invention is intended to embrace all other such alternatives, modifications, and variations that fall within the spirit and scope of the appended claims.

What is claimed is:

1. A method of using a sensor, the method comprising:
while an object travels past the sensor, operating the sensor to obtain sensing results, the sensing results indicating one or more sensed time-varying waveforms with time variation that includes information about the object; and
using the sensing results in a comparing operation on a set of time-varying waveforms to obtain comparison results indicating motion-independent information about the object; the set of time-varying waveforms including at least one of the sensed time-varying waveforms;
the act of using the sensing results in a comparing operation including:
performing time scaling on at least one of the set of time-varying waveforms.

2. The method of claim 1 in which the comparing operation includes a correlation operation; the act of performing time scaling being performed before the correlation operation.

3. The method of claim 1 in which the object is a biological cell and the motion-independent information indicates the cell's type.

4. The method of claim 1 in which the object is a colored spot on a medium and the motion-independent information indicates the spot's color.

5. The method of claim 1 in which the set of time-varying waveforms further includes a reference time-varying waveform, the act of performing time scaling including:
time scaling the reference time-varying waveform.

6. The method of claim 5 in which the reference time-varying waveform is a template waveform.

7. A method of using encoding/sensing arrangements, the method comprising:
operating an encoding/sensing arrangement to obtain sensing results for an object moving relative to the encoding/sensing arrangement, the sensing results indicating one or more sensed time-varying waveforms with time variation as a result of the object's moving relative to the encoding/sensing arrangement; the act of operating the encoding/sensing arrangement to obtain sensing results including:
operating the encoding/sensing arrangement to encode the time variation in accordance with a set of one or more patterns, the set including at least one of:
an excitation pattern;
a pattern in a filter arrangement;
a pattern relative to which the object is displaced;
a patterned sensing arrangement;
a periodic pattern;
a chirp pattern;
a random pattern;
a pattern in space; and
a pattern in time;
the act of operating the encoding/sensing arrangement to obtain sensing results further including at least one of:
photosensing light emanating from the object; and
performing impedance-based sensing; and
performing a comparing operation on a set of time-varying waveforms to obtain comparison results; the set of time-varying waveforms including at least one of the sensed time-varying waveforms and also including a reference time-varying waveform, the reference time-varying waveform being related to at least one of the set of patterns.

8. The method of claim 7 in which the comparison results indicate motion-independent information about the object; the encoding/sensing arrangement including a photosensor; the act of operating the encoding/sensing arrangement to obtain sensing results further comprising:
operating the photosensor to photosense light emanating from the object, the light emanating from the object having time variation that includes the motion-independent information about the object; the sensing results including the motion-independent information.

9. The method of claim 8, further comprising:
using the sensing results to obtain motion-dependent information about the object; the emanating light's time variation further including the motion-dependent information; the sensing results further indicating the motion-dependent information.

10. The method of claim 9 in which the motion-dependent information indicates a displacement rate of the object, the act of performing a comparing operation comprising:
performing time scaling on at least one of the set of time-varying waveforms;
the act of performing time scaling comprising:
time scaling in accordance with the displacement rate of the object indicated by the motion-dependent information.

11. The method of claim 9 in which the sensing results indicate a single time-varying waveform with time variation that includes both the motion-dependent information and the motion-independent information.

12. The method of claim 7 in which the comparison results indicate motion-independent information about the object; the encoding/sensing arrangement including an impedance-based sensor; the act of operating the encoding/sensing arrangement to obtain sensing results further comprising:
operating the impedance-based sensor to provide a time-varying signal that includes the motion-independent information about the object; the sensing results including the time-varying signal.

13. The method of claim 7 in which the comparing operation is a correlation operation and the reference time-varying waveform produces a sharp peak in a correlation result with a time-varying waveform encoded by one of the set of patterns in response to a type of object.

14. The method of claim 7 in which the method uses the encoding/sensing arrangement in one of:
flow cytometry;
biodetection of particles;
analyte detection;
DNA analysis;
proteomics;
bio-chip readout;
scanning of documents; and
scanning of arrays of objects.

15. The method of claim 7 in which the reference time-varying waveform is a template waveform.

16. The method of claim 7 in which the act of performing a comparing operation includes:
time scaling at least one of the set of time-varying waveforms.

17. The method of claim 16 in which one of the set of time-varying waveforms includes periodic modulation, the act of time scaling including:

obtaining a modulation periodicity value from the periodic modulation of the one time-varying waveform; and time scaling at least one of the set of time-varying waveforms based on the modulation periodicity value.

18. The method of claim 16 in which the act of performing a comparing operation includes two or more iterations, the act of time scaling including:

time scaling one of the set of time-varying waveforms for first and second iterations of the comparing operation, the one of the time-varying waveforms being time-scaled at first and second scales for the first and second iterations, respectively.

19. The method of claim 16 in which the act of time scaling at least one of the set of time-varying waveforms includes:

time scaling the reference time-varying waveform.

20. The method of claim 19 in which the comparing operation includes a correlation operation; the act of time scaling the reference time-varying waveform being performed before the correlation operation; the correlation operation being performed on the one sensed time-varying waveform and the time-scaled reference time-varying waveform.

21. The method of claim 20 in which the comparison results indicate motion-independent information about the object and the correlation operation produces correlation results that include a peak; the method further comprising:

using the correlation results to obtain data indicating part of the motion-independent information about the object from a feature of the peak.

22. The method of claim 21 in which the data indicate at least one of:

a position of the object; and a feature of an emanation spectrum of the object.

23. A method of using a sensor, the method comprising:

while objects travel past the sensor, operating the sensor to obtain sensing results, the sensing results indicating one or more sensed time-varying waveforms with time variation that includes information about the objects; and using the sensing results in a comparing operation on a set of time-varying waveforms to obtain comparison results indicating motion-independent information about the objects; the set of time-varying waveforms including at least one of the sensed time-varying waveforms;

the act of using the sensing results in a comparing operation including:

performing time scaling on at least one of the set of time-varying waveforms.

24. The method of claim 23 in which the objects are in a series, the method further comprising:

using the motion-independent information to distinguish objects in the series.

25. The method of claim 24 in which the motion-independent information indicates, for each of a set of the objects, one of a number of object types; the act of using the motion-independent information includes at least one of:

counting objects for which the motion-independent information indicates a first one of the object types; and for a pair of the object types, obtaining a ratio between quantity of objects for which the motion-independent information indicates one of the pair and quantity of objects for which the motion-independent information indicates the other of the pair.

26. The method of claim 23 in which the set of time-varying waveforms further includes a reference time-varying waveform, the act of performing time scaling including:

time scaling the reference time-varying waveform.

27. Apparatus comprising:

a fluidic structure that includes a channel through which objects can travel during operation of the apparatus;

along the channel, a sensor arrangement that can obtain sensing results indicating one or more sensed time-varying waveforms; and circuitry that can receive sensing results from the sensor arrangement and can, in response, obtain information about the objects; the circuitry being structured to use the sensing results from the sensor arrangement in a comparing operation on a set of time-varying waveforms to obtain comparison results indicating motion-independent information about the objects; the set of time-varying waveforms including at least one of the sensed time-varying waveforms;

in using the sensing results in the comparing operation, the circuitry performing time scaling on at least one of the set of time-varying waveforms.

28. The apparatus of claim 27 in which the objects emanate light; the sensor arrangement including:

two or more photosensing components along a part of the channel, the photosensing components concurrently photosensing the emanating light and providing the sensing results.

29. The apparatus of claim 27 in which the sensor arrangement includes:

an impedance-based sensor with a pattern of electrodes; the pattern of electrodes including a combination of a periodic pattern and a non-periodic pattern.

30. The apparatus of claim 27 in which the set of time-varying waveforms further includes a reference time-varying waveform; in using the sensing results in the comparing operation, the circuitry performing time scaling on the reference time-varying waveform.

31. A method of using a sensor, the method comprising:

while an object travels, operating the sensor to obtain sensing results, the sensing results indicating one or more sensed time-varying waveforms that include periodic modulation; and using the sensing results to obtain information about the object; the act of using the sensing results including:

obtaining a modulation periodicity value from the periodic modulation of at least one of the sensed time-varying waveforms; and obtaining information about the object using the modulation periodicity value and one or more of the sensed time-varying waveforms, the act of obtaining information about the object including:

time scaling a first set of one or more time-varying waveforms based on the modulation periodicity value, the first set including at least one of:

one or more of the sensed time-varying waveforms; and a reference time-varying waveform; and comparing a second set of two or more time-varying waveforms; the second set including at least one of the sensed time-varying waveforms; the second set including at least one of the first set of time-scaled time-varying waveforms.

32. The method of claim 31 in which the modulation periodicity value indicates the object's speed.

33. The method of claim 32 in which the act of time scaling includes:

time scaling the reference time-varying waveform based on the modulation periodicity value;

the act of comparing including:
    performing a correlation operation on one of the sensed time-varying waveforms and the time-scaled reference waveform.

34. The method of claim 31 in which the act of comparing a second set of two or more time-varying waveforms comprises one of:
    comparing two of the sensed time-varying waveforms; and
    comparing a sensed time-varying waveform and a reference time-varying waveform.

35. The method of claim 31 in which the first and second sets of time-varying waveforms both include the reference time-varying waveform.

36. A method of using sensors, the method comprising:
    while an object travels, operating a sensor to obtain sensing results, the sensing results indicating one or more sensed time-varying waveforms that include periodic modulation and chirp modulation; and
    using the sensing results to obtain information about the object; the act of using the sensing results including:
        obtaining a modulation periodicity value from the periodic modulation of at least one of the sensed time-varying waveforms;
        obtaining a chirp periodicity value from the chirp modulation of at least one of the sensed time-varying waveforms, the chirp periodicity value indicating chirp periodicity at a respective time; and
    using the modulation and chirp periodicity values to obtain the information about the object at the respective time.

37. The method of claim 36 in which the act of using the modulation and chirp periodicity values comprises:
    obtaining a ratio between the modulation and chirp periodicity values.

38. The method of claim 36 in which the method is performed without using a reference time-varying waveform.

* * * * *